US012713686B2

(12) United States Patent
Rosenstein et al.

(10) Patent No.: US 12,713,686 B2
(45) Date of Patent: Aug. 18, 2026

(54) HYBRID BIOFILM SEMICONDUCTOR INFORMATION SYSTEMS

(71) Applicants: Brown University, Providence, RI (US); Trustees of Boston University, Boston, MA (US)

(72) Inventors: Jacob K. Rosenstein, Providence, RI (US); Kangping Hu, Providence, RI (US); Joseph W. Larkin, Dorchester, MA (US)

(73) Assignees: Brown University, Providence, RI (US); Trustees of Boston University, Boston, MA (US)

(*) Notice: Subject to any disclaimer, the term of this patent is extended or adjusted under 35 U.S.C. 154(b) by 503 days.

(21) Appl. No.: 18/300,278

(22) Filed: Apr. 13, 2023

(65) Prior Publication Data

US 2023/0335445 A1 Oct. 19, 2023

Related U.S. Application Data

(60) Provisional application No. 63/330,644, filed on Apr. 13, 2022.

(51) Int. Cl.
*H10D 84/01* (2026.01)
*C12M 1/12* (2006.01)
(Continued)

(52) U.S. Cl.
CPC ...... *H10D 84/0165* (2025.01); *C12M 1/3407* (2013.01); *C12M 25/14* (2013.01);
(Continued)

(58) Field of Classification Search
CPC ..... C12M 1/3407; C12M 25/14; H01L 22/30; H10D 84/01; H10D 84/0165;
(Continued)

(56) References Cited

U.S. PATENT DOCUMENTS

| | | | |
|---|---|---|---|
| 4,879,517 | A | 11/1989 | Connery et al. |
| 7,500,379 | B2 | 3/2009 | Hines |

(Continued)

FOREIGN PATENT DOCUMENTS

| | | | |
|---|---|---|---|
| CN | 101669026 | B | 5/2014 |
| CN | 104677967 | A | 6/2015 |

(Continued)

OTHER PUBLICATIONS

Arcadia , et al., "CMOS electrochemical imaging arrays for the detection and classification of microorganisms", IEEE International Symposium on Circuits and Systems, 2021, 5 pages.

(Continued)

*Primary Examiner* — Cheung Lee
(74) *Attorney, Agent, or Firm* — Banner & Witcoff, Ltd.

(57) ABSTRACT

Described herein are devices that relate to sensor, data, and interactive interfaces between micro or nano electronics and biofilms, which optionally include an added extracellular matrix. Biofilms in the interfaces can include adherent cells or microorganisms, for example, fungi, bacteria, and the biofilms may include viruses. Computational capability, circuitry, and methods are provided for interactive measurements/processing between the electronics and biofilms.

20 Claims, 34 Drawing Sheets

Trap cells and grow biofilm

(51) Int. Cl.

| | |
|---|---|
| ***C12M 1/34*** | (2006.01) |
| ***H10D 84/03*** | (2025.01) |
| ***H10D 84/85*** | (2025.01) |
| ***H10D 86/01*** | (2025.01) |
| ***H10F 39/00*** | (2025.01) |

(52) U.S. Cl.
CPC ........... *H10D 84/038* (2025.01); *H10D 84/85* (2025.01); *H10D 86/01* (2025.01); *H10F 39/802* (2025.01)

(58) Field of Classification Search
CPC ............. H10D 84/038; H10D 84/8311; H10D 84/8312; H10D 84/83135; H10D 84/83138; H10D 84/8314; H10D 84/8316; H10D 84/85; H10D 84/851–852; H10D 84/907; H10D 86/01; H10F 39/80; H10F 39/802–8027
See application file for complete search history.

(56) References Cited

U.S. PATENT DOCUMENTS

| | | | |
|---|---|---|---|
| 8,293,082 | B2 | 10/2012 | Rothberg et al. |
| 9,001,848 | B2 | 4/2015 | Tzeng et al. |
| 9,360,509 | B2 | 6/2016 | Naughton et al. |
| 9,839,367 | B2 | 12/2017 | Litt et al. |
| 10,126,289 | B2 | 11/2018 | Wang et al. |
| 10,325,951 | B2 | 6/2019 | Graff et al. |
| 2002/0005580 | A1 | 1/2002 | Goodman et al. |
| 2004/0132204 | A1 | 7/2004 | Chou et al. |
| 2005/0221594 | A1 | 10/2005 | Chou et al. |
| 2005/0247559 | A1 | 11/2005 | Frey et al. |
| 2007/0084721 | A1 | 4/2007 | Hsung et al. |
| 2008/0067081 | A1 | 3/2008 | Chou et al. |
| 2010/0140079 | A1 | 6/2010 | Chou et al. |
| 2010/0221846 | A1 | 9/2010 | Widdershoven |
| 2012/0032235 | A1 * | 2/2012 | Bikumandla .......... H10D 99/00 257/253 |
| 2014/0087954 | A1 | 3/2014 | Seligmann et al. |
| 2014/0318958 | A1 | 10/2014 | Hassibi et al. |
| 2014/0326600 | A1 | 11/2014 | Li et al. |
| 2014/0346058 | A1 | 11/2014 | Robitzki et al. |
| 2015/0330941 | A1 | 11/2015 | Smith et al. |
| 2016/0033449 | A1 | 2/2016 | Fife |
| 2016/0245788 | A1 | 8/2016 | Wang et al. |
| 2017/0067890 | A1 | 3/2017 | Lin et al. |
| 2017/0261457 | A1 | 9/2017 | Suy et al. |
| 2017/0272277 | A1 | 9/2017 | Hines et al. |
| 2018/0204036 | A1 | 7/2018 | Akhavan Fomani et al. |
| 2019/0117083 | A1 | 4/2019 | Wang et al. |
| 2019/0204204 | A1 | 7/2019 | Sarioglu |
| 2019/0257829 | A1 | 8/2019 | Ludwig et al. |
| 2019/0369044 | A1 | 12/2019 | Chang et al. |
| 2020/0271620 | A1 | 8/2020 | Cheng et al. |
| 2020/0359921 | A1 | 11/2020 | Manoli et al. |
| 2021/0199619 | A1 | 7/2021 | Sekine |

FOREIGN PATENT DOCUMENTS

| | | | |
|---|---|---|---|
| CN | 109307701 | A | 2/2019 |
| EP | 2342552 | A1 | 7/2011 |
| EP | 2807478 | A1 | 12/2014 |
| EP | 2939185 | A1 | 11/2015 |

OTHER PUBLICATIONS

Chen , et al., "Column-Parallel Digital Correlated Multiple Sampling for Low-Noise CMOS Image Sensors", IEEE Sensors Journal, vol. 12, No. 4, 2012, pp. 793-799.

Cong , et al., "A 3600 x 3600 Large-scale ISFET Sensor Array for High-throughput pH Sensing", IEEE 12th International Conference on ASIC, 2017, pp. 957-960.

Cossettini , et al., "Space and frequency dependence of nanocapacitor array sensors response to microparticles in electrolyte", IEEE Sensors Journal, vol. 21, No. 4, 2020, pp. 4696-4704.

Dubois , et al., "A 10 000 fps CMOS Sensor With Massively Parallel Image Processing", IEEE Journal of Solid-state Circuits, vol. 43, No. 3, 2008, pp. 706-717.

Hassibi , et al., "A Programmable 0.18-μm CMOS Electrochemical Sensor Microarray for Biomolecular Detection", IEEE Sensors Journal, vol. 6, No. 6, Dec. 6, 2006, pp. 1380-1388.

Hu , et al., "A 13.1 mm2 512 x 256 Multimodal CMOS Array for Spatiochemical Imaging of Bacterial Biofilms", 2022 IEEE Custom Integrated Circuits Conference (CICC), 2022, 9 pages.

Hu , et al., "A Fringe Field Shaping CMOS Capacitive Imaging Array", IEEE Sensors,, 2021, pp. 1-4.

Hu , et al., "A Large-Scale Multimodal CMOS Biosensor Array With 131,072 Pixels and Code-Division Multiplexed Readout", IEEE Solid-State Circuits Letters, vol. 4, 2021, 4 pages.

Hu , et al., "High Frequency Dielectric Spectroscopy Array with Code Division Multiplexing for Biological Imaging", IEEE Biomedical Circuits and Systems Conference (BioCAS), 2019, pp. 1-4.

Hu , et al., "Low Noise CMOS ISFETs Using In-Pixel Chopping", IEEE Biomedical Circuits and Systems Conference, 2021, pp. 1-4.

Hu , et al., "Super-Resolution Electrochemical Impedance Imaging with a 100X100 CMOS Sensor Array", IEEE Biomedical Circuits and Systems Conference (BioCAS), 2021, pp. 1-4.

Jainwal , et al., "1/f Noise Reduction using In-Pixel Chopping in CMOS Image Sensor", Journal Of Latex Class Files, vol. 13, No. 9, Jan. 2016, 5 pages.

Jainwal, Kapil , "Low-Frequency Noise Reduction Using In-Pixel Chopping To Enhance The Dynamic Range of a CMOS Image Sensor", Journal Of Latex Class Files, vol. 13, No. 9, Jan. 2016, 11 pages.

Jung , et al., "A 21952-pixel multi-modal CMOS cellular sensor array with 1568-pixel parallel recording and 4-point impedance sensing", Symposium on VLSI Circuits, 2019, pp. C62-C63.

Jung , et al., "A CMOS 21 952-pixel multi-modal cell-based biosensor with four-point impedance sensing for holistic cellular characterization", IEEE Journal of Solid-State Circuits, vol. 56, No. 8, Aug. 2021, pp. 2438-2451.

Linderholm , et al., "Cell Culture Imaging Using Microimpedance Tomography", IEEE Transactions on Biomedical Engineering, vol. 55, 2008, pp. 138-146.

Manickam , et al., "A CMOS Electrochemical Impedance Spectroscopy Biosensor Array for Label-Free Biomolecular Detection", IEEE International Solid-State Circuits Conference, Session 6, Displays & Biomedical Devices, 6.9, Feb. 8, 2010, 3 pages.

Moser , et al., "A Scalable ISFET Sensing and Memory Array With Sensor Auto-Calibration for On-Chip Real-Time DNA Detection", IEEE Transactions on Biomedical Circuits and Systems, vol. 12, No. 2, 2018, pp. 390-401.

Nakazato, Kazuo , "An Integrated ISFET Sensor Array", Sensor, vol. 9, No. 11, Nov. 4, 2009, pp. 8831-8851.

Park , et al., "Biopsy needle integrated with multi-modal physical/chemical sensor array", Biosensors & Bioelectronics, vol. 148, 2020, 11 pages.

Viswam , et al., "Impedance Spectroscopy and Electrophysiological Imaging of Cells With a High-Density CMOS Microelectrode Array System", IEEE Trans Biomed Circuits System, vol. 12, No. 6, 2018, pp. 1356-1368.

Widdershoven , et al., "A CMOS Pixelated Nanocapacitor Biosensor Platform for High-Frequency Impedance Spectroscopy and Imaging", IEEE Transactions on Biomedical Circuits and Systems, vol. 12, No. 6, 2008, pp. 138-146.

* cited by examiner

Communication between biofilms

| Biofilm location, size, growth | radio-frequency impedance |
|---|---|
| local metabolism | ISFET (pH) |
| electrical signaling | extracellular potential & ISFET (pK) |
| electrical signaling | programmable electrical stimulation |
| gene expression | fluorescence imaging (external) |

After 3.6 V stimulation

20 μm

| | This Work | TBCAS, 2018 J. Park | SSCL, 2021 K. Hu | TBME, 2015 X. Huang | TBCAS, 2018 F. Widdershoven |
|---|---|---|---|---|---|
| **Modality** | Impedance + Temperature + pH +Heating + Current/Voltage stimulation | Voltage + Optical + Impedance + Current Stimulation | Impedance + pH + Optical | pH + Optical | Impedance |
| **Electrical Capacitance Tomography** | Yes | No | No | No | No |
| **# of pixels** | 131,072 | 1,024 | 131,072 | 4,096 | 65,536 |
| **Field of View** | 2.56 x 5.12 (13.1 $mm^2$) | 1.85 x 1.85 (3.4 $mm^2$) | 2.43 x 5.89 (14.3 $mm^2$) | 0.64 x 0.64 (0.4 $mm^2$) | 0.25 x 0.175 (0.04 $mm^2$) |
| **Pixel Size** | 10 x 10 $\mu m^2$ | 58 x 58 $\mu m^2$ | 9.5 x 11.5 $\mu m^2$ | 10 x 10 $\mu m^2$ | 0.6 x 0.89 $\mu m^2$ |
| **Max. Impedance Frequency** | 100 MHz | 1 MHz | 100 MHz | N/A | 70 MHz |
| **Impedance Resolution** | 0.13 attofarads | N/A | 0.7 attofarads | N/A | 0.5 ~ 1 attofarads |
| **Electrode Material** | $TiN$ | $Au$ | $TiN$ | $Si_3N_4$ | $Au - Cu$ |
| **ISFET Sensitivity** | 27.2mV/pH | N/A | 27.7 mV/pH | 26.2 mV/pH | N/A |
| **# of Channels** | 8 | 4 | 1 | 1 | 8 |
| **Experimental Demonstration** | *B. subtilis* | Rat cardiomyocyte | *S.epidermidis* | *E. coli* | Nanoparticles |
| **CMOS Technology Node** | 180nm | 130nm | 180nm | 180nm | 90nm |

FIG. 20

HYBRID BIOFILM SEMICONDUCTOR INFORMATION SYSTEMS

CROSS REFERENCE TO RELATED APPLICATIONS

This application claims benefit from U.S. Provisional Patent Application Ser. No. 63/330,644, filed Apr. 13, 2022, which is incorporated by reference herein in its entirety.

STATEMENT REGARDING FEDERALLY SPONSORED RESEARCH OR DEVELOPMENT

This invention was made with government support under grant number 2027108 awarded by the National Science Foundation. The government has certain rights in the invention.

FIELD OF THE INVENTION

The embodiments of the present invention relate to sensor, data, and interactive interfaces between micro or nano electronics and biofilms, which optionally include an added extracellular matrix. Biofilms in the interfaces can include adherent cells or microorganisms, for example, fungi, bacteria, and the biofilms may include viruses.

BACKGROUND OF THE INVENTION

A biofilm is an assemblage of surface-associated microbial cells that can include an extracellular matrix. Along with bacteria, biofilms can be initiated and produced by eukaryotic microbes. The extracellular matrix can include an added polymeric substance or can be excreted from the biofilm. Biofilms may form on living or non-living surfaces and can be prevalent in natural, industrial, and hospital settings[1]. A biofilm may constitute a microbiome or be a portion of it. In the most common settings, biofilms can form on the teeth of most animals as dental plaque, where they may cause tooth decay and gum disease. In nature, biofilms can form on rocks, reefs, and moist environments. A typical biofilm can begin to form when a free-swimming bacterium attaches to a surface.

A biofilm can be considered a hydrogel, which is a complex polymer that contains many times its dry weight in water. Biofilms are not just microbial or bacterial slime layers but biological systems; the microbes can organize themselves into a coordinated functional community or microbiome. Biofilms may include a single species or a diverse group of microorganisms. Subpopulations of cells within the biofilm differentiate to perform various activities for motility, matrix production, and sporulation, supporting the overall success of the biofilm[2]. The biofilm microbes or bacteria can share nutrients and are sheltered from harmful factors in the environment, such as desiccation, antibiotics, and a host body's immune system. However, this could potentially be overcome by the development of more predictive in vitro models.

While biofilms can be problematic in industries such as the food industry and aquaculture, the study of biofilms is critical for understanding the development of infections and microbiomes (including the human microbiome). Optical imaging (e.g., microscopic images) of biofilms is tedious and limited, even when image analysis is automated. Meanwhile, biofilms offer an unexplored opportunity for processing. Accordingly, there is a need for the development of accurate information systems and interfaces between biofilms and semiconductors.

BRIEF SUMMARY OF THE INVENTION

There are few recent technology trends which have been as consistent and as consequential as the exponential improvement of semiconductor technology. Moore's Law has been in effect for longer than many of today's scientists and engineers have been alive. Yet there are still important information-processing functions in which biology outperforms modern semiconductors. Some of the most useful examples are at the smallest scales: single-celled bacteria are able to sense their surroundings, harvest energy, move, and reproduce, while fitting all of the necessary components within sub-micron volumes. Individual bacteria living in communities are known to coordinate through electrochemical signaling strategies. If we can integrate communities of bacteria with traditional microelectronics, perhaps we could produce new hybrid computational systems which combine the impressive energy efficiency, environmental resilience, and multifunctional chemical sensing of bacterial biofilms, with the flexibility and real-time programmability of modern semiconductors.

The technology disclosed herein can provide an interface between living cells/organisms and electronics. In various examples, the present innovation can contemplate biofilms, biological computing, CMOS (complementary metal-oxide semiconductor), bacteria, bioelectronics, molecular computing, and molecular information.

The present invention, in one of its broadest embodiments, provides a CMOS (complementary metal-oxide semiconductor) chip comprising: an array of pixels, each pixel comprising a circuit operative to measure from and/or to apply an electrical charge and/or impedance to at least a portion of a live biofilm disposed on the array; the living biofilm disposed on the array, wherein a portion of the biofilm is in discrete electrical communication with each pixel; and a circuit in electrical communication with the array, said circuit operative to provide at least one signal for each pixel.

In some embodiments, the CMOS chip can be configured as any semiconductor chip. In some embodiments, the chip can be configured wherein each pixel comprises at least one circuit operative to perform a function selected from stimulate, heat, impedance image, measure pH, ion imaging/measurement, temperature measurement, stimulation, measure an amperometry, measure a voltage, measure a resistance, and measure an impedance tomography, of a portion of a biofilm.

According to some aspects, the (CMOS) chip can further comprise a reference electrode and a hydrogel disposed over the biofilm.

In some embodiments, the (CMOS) chip can be configured wherein the biofilm includes at least two biofilms, each of the at least two biofilms in communication with another of the at least two biofilms, wherein the communication comprises a signaling and/or a coupling between biofilms. According to some aspects, the biofilm can comprise a genetically modified cell, a combination of cells, and/or a genetically modified strain of bacteria.

In some embodiments, the (CMOS) can further comprise (or be in further electrical communication with) a processor, memory, programming instructions, and/or display operative to read, store, and display at least one measurement, charge, and/or impedance from the array.

In some embodiments, the (CMOS) chip can be configured wherein the chip is operative to apply an electrical stimulation to a pixel including the biofilm disposed on the pixel, the electrical stimulation comprising at least a bit of information provided in a current/voltage stimulation, and said biofilm is operative to store the bit for a period of time. In this example, the bit of information can be read from the biofilm by applying at least an impedance measurement, a resistance measurement, an amperometry measurement, a current/voltage stimulation, or a combination thereof to the pixel; and wherein the biofilm is capable of changing at least one bit by a cell-to-cell and/or a biofilm-to-biofilm interaction. The change can be a computation using the living biofilm as a processor or computer.

In some embodiments, the chip is configured as an imaging chip capable of imaging the biofilm including computed tomography and/or impedance imaging of the biofilm, and wherein each pixel represents an imaging pixel.

According to some aspects, a method for measuring at least one aspect of a biofilm is disclosed herein, the method comprising the steps of:

(1) obtaining a CMOS (complementary metal-oxide semiconductor) chip comprising:

an array of pixels, each pixel comprising a circuit operative to measure from and/or to apply an electrical charge and/or impedance to at least a portion of a biofilm;

a biofilm disposed on the array, a portion of the biofilm in electrical communication with each pixel; and a circuit in electrical communication with the array, said circuit operative to provide at least one signal for each pixel;

(2) applying a current and/or voltage to a biofilm directly disposed on a pixel, whereby the current and/or voltage is in electrical communication with at least a portion of the biofilm and provides a signal indicative of a condition of at least the portion; and (3) transmitting the signal via an electrical conductor from the pixel to an additional circuitry operative to move the signal from the chip.

The method disclosed above can, in some embodiments, further comprise circuitry in communication with the chip, said circuitry in communication with the chip operative to provide the signal to a processor, memory, field-programmable gate array, DDR3 (RAM/SDRAM), a USB 3.0 output, an analog to digital convertor (ADC), or a combination thereof.

According to some aspects, the method can be performed wherein the (2) applying a current and/or voltage to a pixel is operative to store at least a bit of information in the biofilm. In this example, the at least a bit of information in the biofilm is capable of being read back by a repeating of step (2) and step (3) in any order. The method can be repeated in steps (2) and (3) to different pixels, whereby a plurality of bits of information is applied to discrete areas of the biofilm.

In some embodiments, the method disclosed above changes patterns of a cellular gene expression, intracellular and/or extracellular electrical responses, and/or communication between/among at least one biofilm.

In some embodiments, the biofilm comprises cells/microbes of fungal, bacterial, and/or eukaryotic origin, optionally wherein the cells are derived from *Staphylococcus aureus, Escherichia coli, Streptococcus pneumoniae, Pseudomonas aeruginosa, Bacillus subtilis*, skin (epidermal/dermal) cells, or the archaeal species *H. volcanii*, transfected cells, recombinant cells, genetically engineered cells, normal eukaryotic cells, immune cells such as macrophages, eosinophils, or a combination thereof. According to some aspects, the biofilm includes viruses, culture medium, pharmaceutical agents, prions, oligonucleotides, antibodies, additives, or a combination thereof.

In some embodiments, the technology disclosed herein provides a method for computing within a living biofilm, the method comprising the steps of:

(1) obtaining a CMOS (complementary metal-oxide semiconductor) chip comprising:

an array of pixels, each pixel comprising a circuit operative to measure from and/or to apply an electrical charge and/or impedance to at least a portion of a biofilm;

a biofilm disposed on the array, a portion of the biofilm in electrical communication with each pixel; and a circuit in electrical communication with the array, said circuit operative to provide at least one signal for each pixel;

(2) applying a current and/or voltage to a biofilm directly disposed on a pixel, whereby the current and/or voltage is in electrical communication with at least a portion of the biofilm and stores a signal indicative of a bit of information in the at least the portion of the biofilm;

(3) repeating step (2) such that a plurality of different bits of information are stored in discrete pixels of the biofilm; and (4) waiting a period of time for an interaction between pixels of the biofilm; whereby said interaction is a computation within the living biofilm.

In some embodiments, the method for computing includes an interaction within the biofilm that is a function.

In some embodiments, the plurality of different bits of information is representative of a problem selected from a 2D lattice model, Ising model, an analog model, and an XY model; and wherein the period of time is sufficient for the living biofilm to change at least one of the bits of information.

The method(s) of computing within a living biofilm, according to some aspects, can further comprise the step of:

(5) repeatedly applying a current and/or voltage to a biofilm directly disposed on a pixel, while changing the position of the pixel, whereby a change in at least one bit caused by the biofilm is detected and such change is representative of a computation performed within the biofilm.

In some embodiments, a screening method for therapeutic agents or a method for evaluating the efficacy or toxicity of a therapeutic agent candidate substance acting on cells or biofilms comprising the methods disclosed above is provided, for example, by flowing or applying various agents and/or additives to the biofilm.

In some embodiments, a method of culturing cells, or tissues, comprising the methods disclosed herein is provided, with the proviso that the methods can be performed with or without including a test condition.

In some embodiments, the methods can be wherein biofilms include cells comprising or derived from *Staphylococcus aureus, Escherichia coli, Streptococcus pneumoniae, Pseudomonas aeruginosa, Bacillus subtilis*, skin cells, or the archaeal species *H. volcanii*, transfected cells, recombinant cells, genetically engineered cells, normal eukaryotic cells, immune cells such as macrophages, eosinophils, or a combination thereof. Biofilms can include viruses, pharmaceutical agents, prions, oligonucleotides, antibodies, additives, or a combination thereof. In some embodiments, the culture medium comprises spheroids including cells, monodispersed cells, or a combination thereof.

Other implementations are also described and recited herein.

BRIEF DESCRIPTION OF THE DRAWINGS

For the purpose of illustration, certain embodiments of the present invention are shown in the drawings described below. It should be understood, however, that the invention is not limited to the precise arrangements, methods, dimensions, and instruments shown. In the drawings:

FIG. 1 provides a schematic example of electrical signaling at the cellular and biofilm level.

FIG. 2 provides images and data of biofilm signaling (e.g., electrical signaling).

In FIG. 9, localized electrical stimulation will induce semi-permanent changes to some cells in the biofilm. This can be considered 'writing' data into the biofilm. The data can be 'read' by probing locally to identify the original stimulation pattern, or we can 'compute' on the data by probing for new collective responses from the biofilm.

FIG. 11 provides an example of genetic engineering of electrical signaling.

FIG. 16 illustrates a *Bacillus subtilis* biofilm in contact with the sensor (FIG. 16A, bottom).

FIG. 18 illustrates how electrical capacitance tomography can be used to estimate out-of-plane sample permittivity.

FIG. 20 provides a summary table of some experimental demonstrations of the presently disclosed work.

DETAILED DESCRIPTION OF THE INVENTION

Figure 1A:
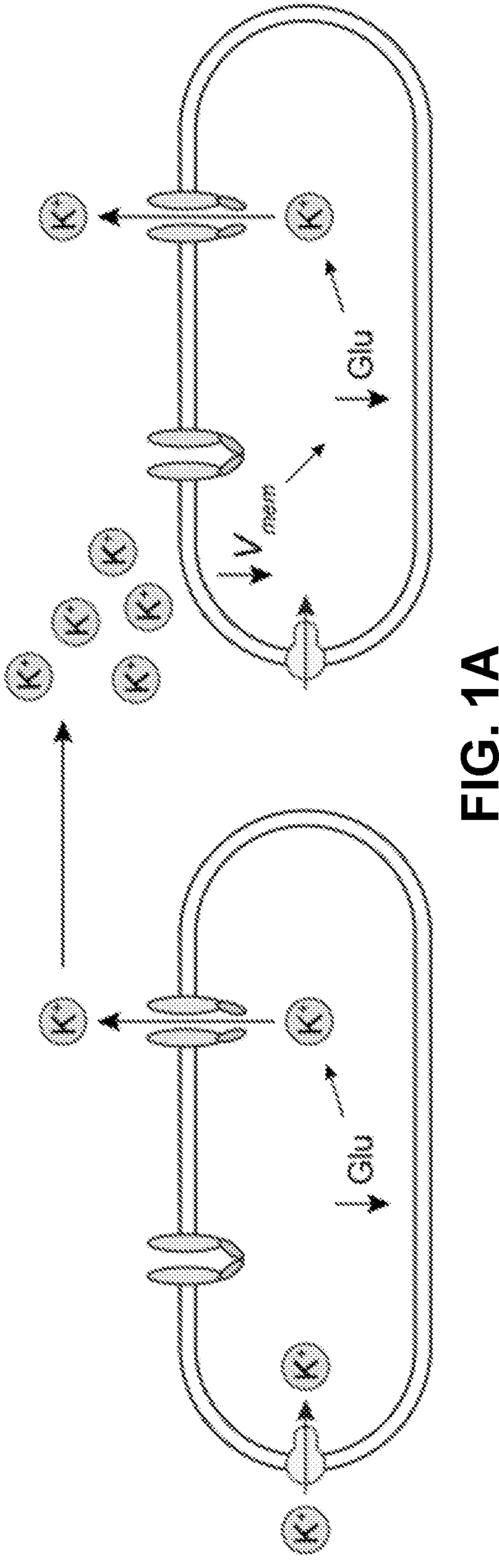
FIG. 1A illustrates at far left how cells maintain high cytoplasmic K+ by pumping in ions. When they are starved of glutamate, K+ channels open, releasing ions, which can depolarize neighbors. Depolarization interrupts glutamate import, causing neighbors to become starved and reinitiate (right) the electrical signal.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention. It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment but can optionally be used to exclude additional elements. The term permits the presence of additional elements that do not materially affect the basic and novel or functional characteristic(s) of that embodiment of the invention. As such, the term "consisting essentially of" can be used in the claimed invention as a proviso, for example, "with the proviso that the device/method does not comprise . . . ". In this example, the term "consisting essentially of" optionally can be utilized in the claims along with a proviso.

The term "statistically significant" or "significantly" refers to statistical significance and generally means a two-standard deviation (2SD) or greater difference.

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the terms "effective amount" and "therapeutically effective amount" include an amount sufficient to prevent or ameliorate a manifestation of disease or medical condition, such as cancer. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment.

The terms: "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the term "CMOS" chip can be interchanged with any semiconductor chip known in the art. As used herein, the term "bit" refers to a binary digit (0 or 1), which is the smallest unit of data that a computer can process and store. A bit is always in one of two physical states, similar to an on/off light switch. The state is represented by a single binary value, usually a 0 or 1. However, the state might also be represented by yes/no, on/off or true/false.

A used herein, the term "computing" refers to a change in a bit on either a processor (CPU) or in a living biofilm. In computing within a living biofilm, the change can occur in the examples depicted in any of the figures herein.

Other terms are defined herein within the description of the various aspects of the invention.

Hybrid Biofilm Semiconductor Information Systems

The innovation disclosed herein provides hybrid information systems using bacterial biofilms integrated with semiconductor technology. Bacterial biofilms are known to be highly complex systems with emergent order, which can survive in widely varying environments. It was recently observed that *Bacillus subtilis* cells in biofilms use ion channels to propagate electrical potential waves among populations of thousands of individual bacteria. Thanks to signal regeneration by downstream cells, these electrical signaling modes have the potential to travel farther than by diffusion alone, and they offer a unique opportunity for new modes of interfacing electronics and biology. Our first milestone is the design of a hardware platform which incorporates living biofilms on active semiconductor chips, which can both sense and actuate signaling within the biofilms. The second milestone or goal is to study the underlying mechanisms of electrical signaling and oscillations within single biofilms, as well as signaling between multiple nearby biofilms. The third is to utilize the electrical properties of the biofilm to encode abstract information written using addressable electrical stimulation, and to perform hybrid computations using programmable networks of coupled bacterial biofilm oscillators.

The technology can be applied to bioelectronics and computing. Given the interdisciplinary nature of hybrid semiconductor-bacteria plat forms, the technology enables investigation of frontiers at the intersection of electronics, computing, and biology.

1 Intellectual Merit

Many analogies exist between biological networks and electronic computers, including the recent rise of bioinspired neural network algorithms. Yet mammalian cells are not the only living networks which coordinate among many cells and perform collective computations using information from their environment. Bacteria can form complex biofilms which serve both to protect the colony from the surrounding environment, and to facilitate chemical and electrical communication among the thousands of cells which comprise it[3,4,5]. The partially amorphous structure of a biofilm allows it to operate with individual cells which are physically smaller, genetically simpler, and more robust than many mammalian cells. The overarching objective of this technology is to create hybrid bioelectronic systems which use the emergent complexity of bacterial biofilms to encode information and perform computational tasks. Similar to neurons and other excitable cells, bacteria can use differential concentrations of dissolved ions to create and respond to electrical signals. We utilize newly discovered electrical signaling modes among communities of *Bacillus subtilis*, paired with modern microelectronic circuits. These cooperative electrical signals share some themes with traditional quorum sensing, though they are a distinct area of research. To achieve our objectives, we propose three miles or goals:

1. A new platform for CMOS-biofilm bidirectional communication: We design a multimodal integrated circuit which can electrically stimulate biofilms in complex spatial and temporal patterns, while sensing the similarly complex electrochemical response from the biofilms. Biofilms will be cultured on the surface of a complementary metal oxide semiconductor (CMOS) integrated circuit, allowing measurements of spatially resolved pH and impedance of the biofilm. The sensor will make use of radio frequency dielectric imaging which overcomes Debye screening. When appropriate, we perform simultaneous electrical and optical imaging of the biofilms.

2. Exploring information exchange among communities of bacteria in biofilms: It is well known that bacteria use 'quorum sensing' to coordinate actions among the many independent cells that make up a biofilm. However, relying on diffusion-based communication has an inherently limited length scale. Herein we elucidate mechanisms of electrical coupling between *B. subtilis* bacteria, using the custom non-optical CMOS sensor array as well as more established fluorescent dyes sensitive to membrane potential. We characterize electrochemical signal propagation within single biofilms, as well as information transfer between multiple biofilms which share a common environment. By applying electrical stimulation through CMOS microelectrode arrays, we also show the response of biofilms to spatiotemporally complex electrical stimuli.

3. Evaluating information storage and in-biofilm computation using electrical activity: Electrical stimulation of biofilms can have long-term effects on the structure and behavior of the bacteria. Herein we evaluate the speed, density, precision, and retention time of information written into biofilms via localized electrical stimulation. This information may be retrieved either by electrically probing for a response from the biofilm, or by interpreting the community's self-sustaining metabolic oscillations. We further explore models of in-biofilm computation, where logical operations are performed on the information written into the biofilm, based on the fact that neighboring cells (or neighboring biofilms) may be electrochemically coupled.

Much bioelectronic system development has focused on electronic interfaces with excitable eukaryotic cells such as neurons and cardiomyocytes. However, there has been comparatively little exploration of how semiconductor technology can interface with bacterial biofilms. When it comes to bacteria, there are many tools for genetically engineering microorganisms for molecular biology and newer synthetic biology functions. There is also, of course, much research towards antibiotics to eliminate biofilms. Yet relatively few examples exist which attempt to use the emergent properties of biofilms for productive applications.

Biofilms have valuable properties for hybrid bioelectronic devices. In contrast to many excitable mammalian cells, biofilms are environmentally robust, and can survive across a wide variety of temperatures and chemical conditions. Biofilms often self-organize naturally on surfaces[6], and can live in contact with foreign objects with varied mechanical and chemical properties[7].

Although bacterial ion channels have been studied at a molecular level for many years, there have been relatively few studies of electrical signaling within biofilms. The few measurements thus far have often relied on fluorescent dyes[8]. To avoid phototoxicity, fluorescent potential measurements may only be made every few minutes[9], and electrical oscillations have only been studied at fairly slow timescales. These slow measurements contrast with the fact that ion channels frequently have kinetics and transient response with millisecond timescales. We study electrical biofilm signaling at these faster timescales with our semiconductor imaging system.

This project provides new types of bioelectronic interfaces, in directions not explored currently in the literature. These new strategies for electrically coupling semiconductors to biofilms will be useful for other hybrid bioelectronic systems, for example interfacing with bacteria which are also genetically engineered for sensing applications. We expect that research at the intersection of computing, microbiology, and chemistry will lead to new technological and scientific discoveries. Furthermore, we anticipate that our research will be of direct relevance to many semiconductor, computing, and biotechnology companies, and we plan to develop relationships with industrial partners in these areas during the project.

2 Microbes—Biofilms Background

The majority of microbes on earth do not live as solitary cells. Instead, they form biofilms, communities of cells stuck together by a self-produced extracellular polymeric matrix[10]. By engaging in remarkable group strategies and emergent behaviors[11], these microbial communities are able to thrive in nearly every environment from the bottom of the ocean to deep soil to the gut[12]. When they are living in biofilms, bacteria exhibit significantly greater resistance to antibiotics than free-living cells, and this resistance is not merely attributable to the inability of antibiotics to penetrate the biofilm matrix[13]. An intriguing hypothesis is that the resilience of biofilms arises from cell-to-cell communication strategies, such as quorum sensing[14] and electrical communication[3,4]. The latter phenomenon is a very recent discovery that has significant potential for engineering biological information processing systems.

Bacterial biofilms of the species *Bacillus subtilis* can transmit electrochemical signals within their population. These signals propagate via a process of ion channels opening and closing in response to nitrogen starvation[8,15]. The example mechanism of signal propagation is shown schematically in FIG. 1A. Cells become starved of glutamate, causing potassium channels to open, ions to leave cells, and cell membranes to hyperpolarize. Released ions can enter neighboring cells, depolarizing their membranes, and interfering with the uptake of amino acids[16]. These cells then become starved themselves, reinitiating the electrical dynamics and propagating the signal to other nearby cells. The dynamics of this excitable wave are very much like that of a neuronal action potential, but roughly five orders of magnitude slower[8,9].

Figures 2A, 2B:
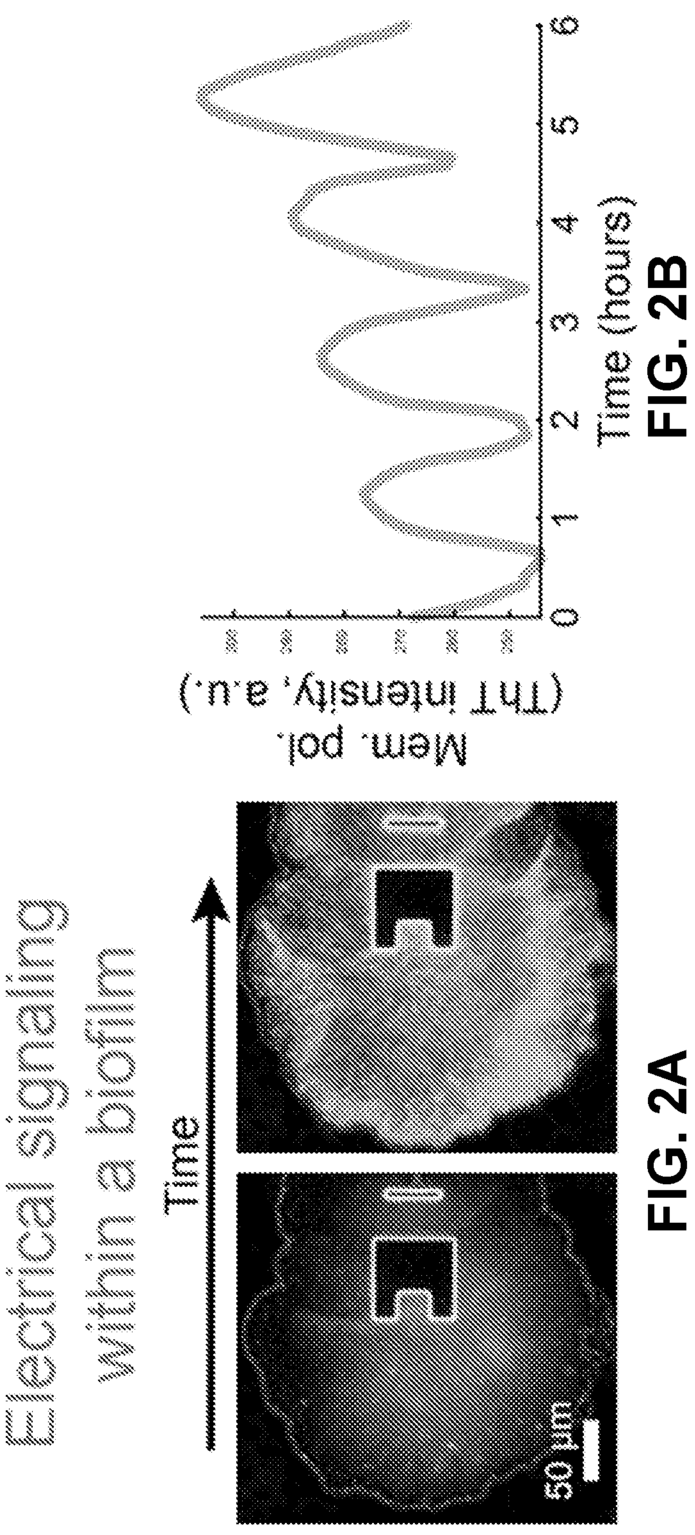
FIG. 2A shows images of how a biofilm propagates an electrical signal within its population as observed with fluorescent voltage indicators (lighter grey image areas).
FIG. 2B shows a plot of the voltage indicator signal (the biofilm edge) showing oscillatory electrical activity.

Up to this point, we have measured membrane potential during these signals with fluorescent voltage reporters (FIG. 2A, 2B, lighter grey). These are positively charged dyes that can enter cells. Their uptake is membrane potential dependent such that a negatively polarized cell takes in more of the dye than an unpolarized cell and exhibits higher fluorescence intensity. If the membrane potential changes on a time scale that is slower than the reorganization time of the dye, then this change can be measured qualitatively as a change in fluorescence[17]. These dyes have several major drawbacks: they are only useful for measurements of slow electrical activity, measurements on large biofilms are difficult due to high background fluorescence, and repeated fluorescence measurements impart significant phototoxicity.

Figure 1B:
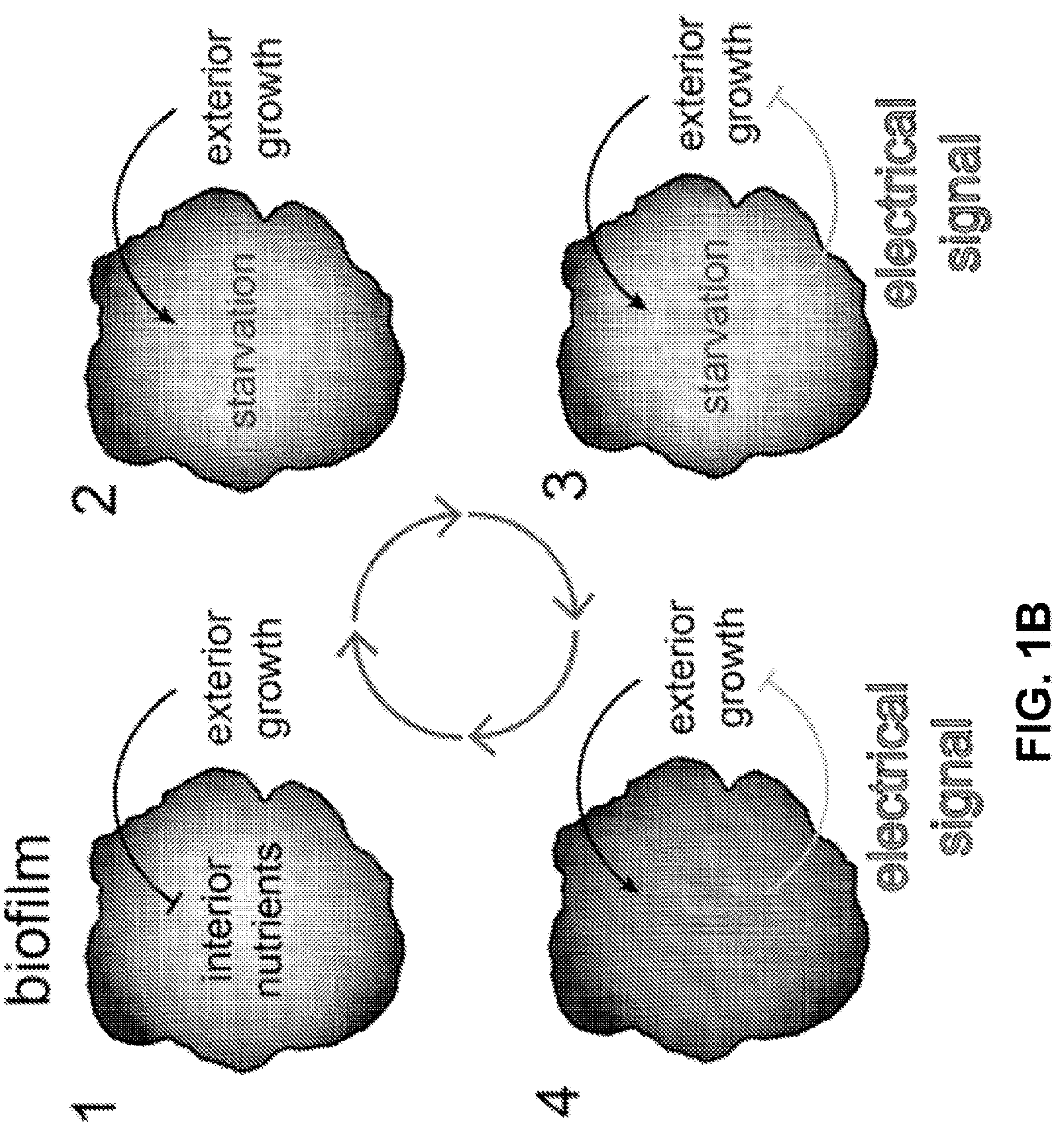
FIG. 1B illustrates how exterior biofilm growth (1) leads to nutrient starvation at the interior (2). This causes an electrical signal originating from the interior (3), which forces starvation on the exterior, leading to less consumption and more nutrients for the interior (4). Nutrient access is illustrated by the scale at left.

The major function of electrical signaling within biofilms is to coordinate metabolism across large distances[15]. Once biofilms become sufficiently large, nutrient consumption by exterior cells outpaces diffusion to the biofilm interior. Cells on the interior then become starved, and can no longer provide essential secondary metabolites to the whole community[15]. This starvation initiates the electrical signal, which then propagates to the exterior. Once the signal reaches the exterior, it interrupts the ability of cells to take in nutrients because cells rely on a consistent membrane potential to import amino acids[16]. Exterior cells that have easy access to nutrients now consume less, so more nutrients are available to the interior, and interior cells do not die. In this way, electrical signaling arises out of a spatially extended feedback loop between growth and metabolism of interior and exterior biofilm cells (FIG. 1B). The feedback results in oscillations, where signals are propagated from the interior to the exterior at regular intervals (FIG. 2B).

Figure 3A:
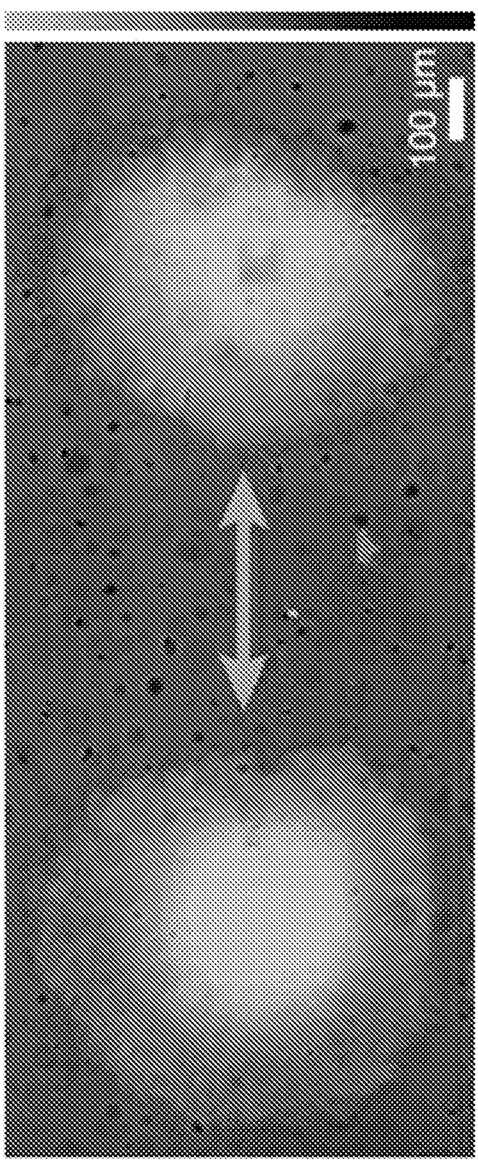
FIG. 3A shows a microscopic image of biofilm-to-biofilm coupling with two biofilms growing in the same environments. Coupling data demonstrates two biofilms growing in the same environment can synchronize their electrical oscillations as shown in the example of FIG. 3B (high coupling) or, if nutrient conditions are low, antisynchronize their electrical oscillations as shown in the example of FIG. 3C (low coupling).
Figure 3B:
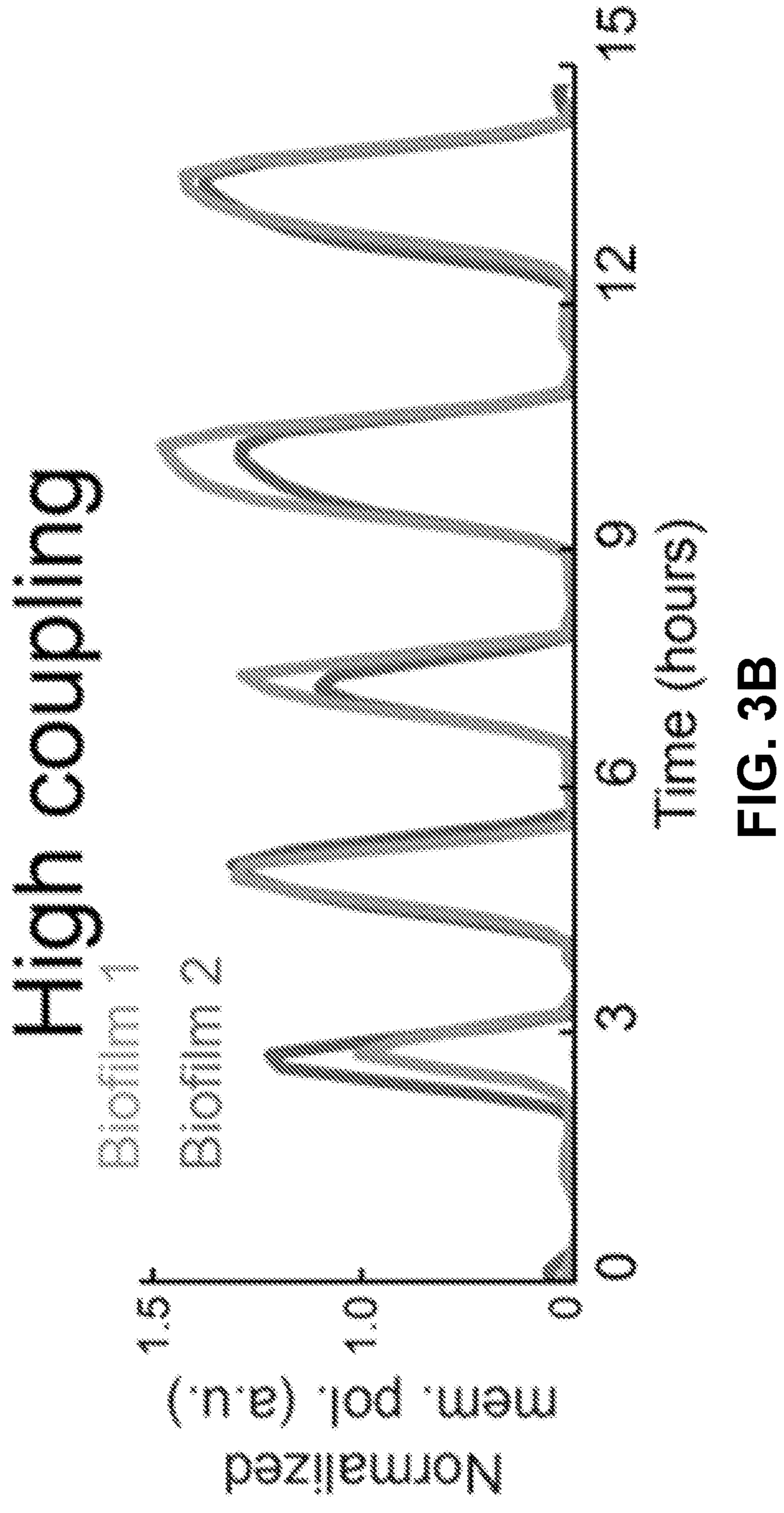
FIG. 3 provides images and data showing biofilm-to-biofilm coupling (e.g., communication between biofilms).
Figure 3C:
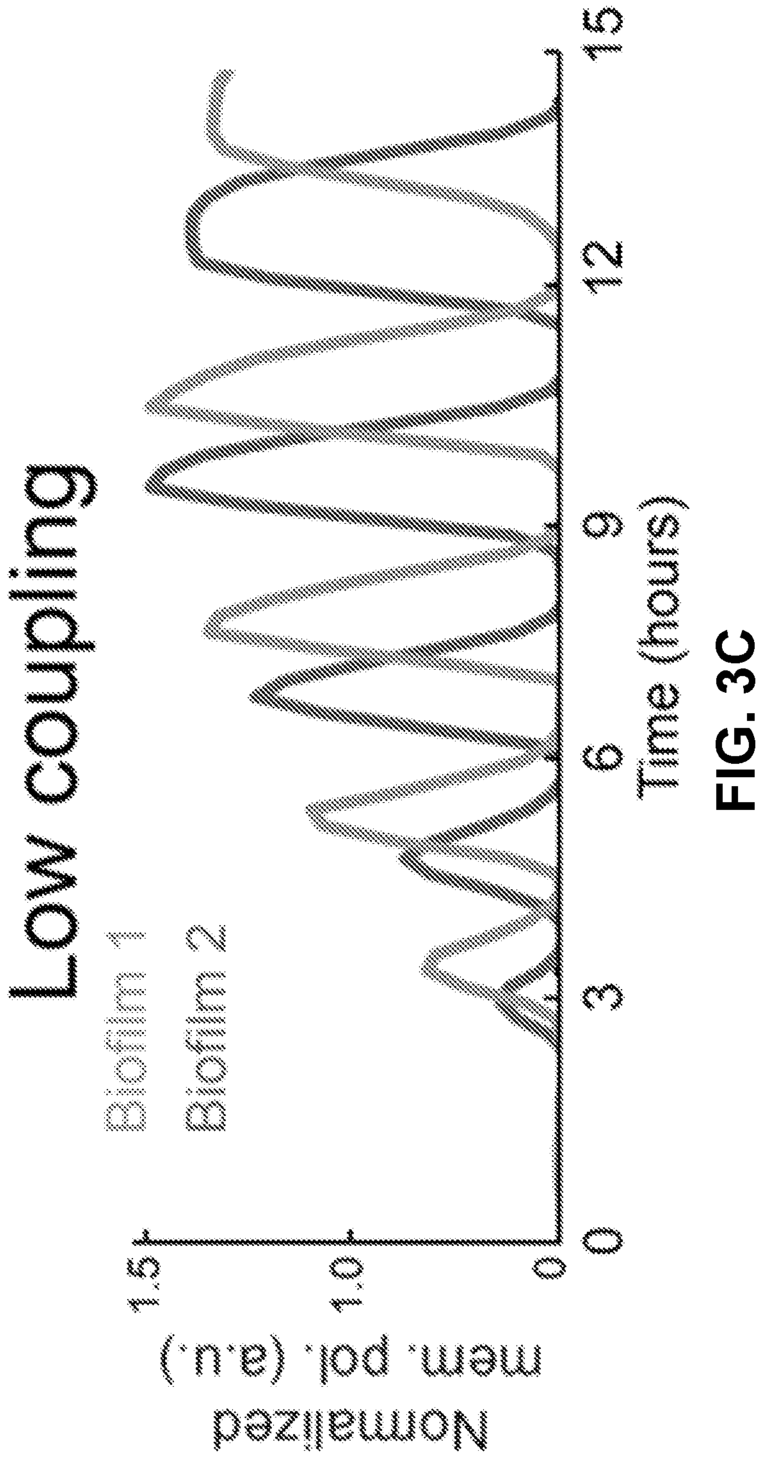
Figure 4:
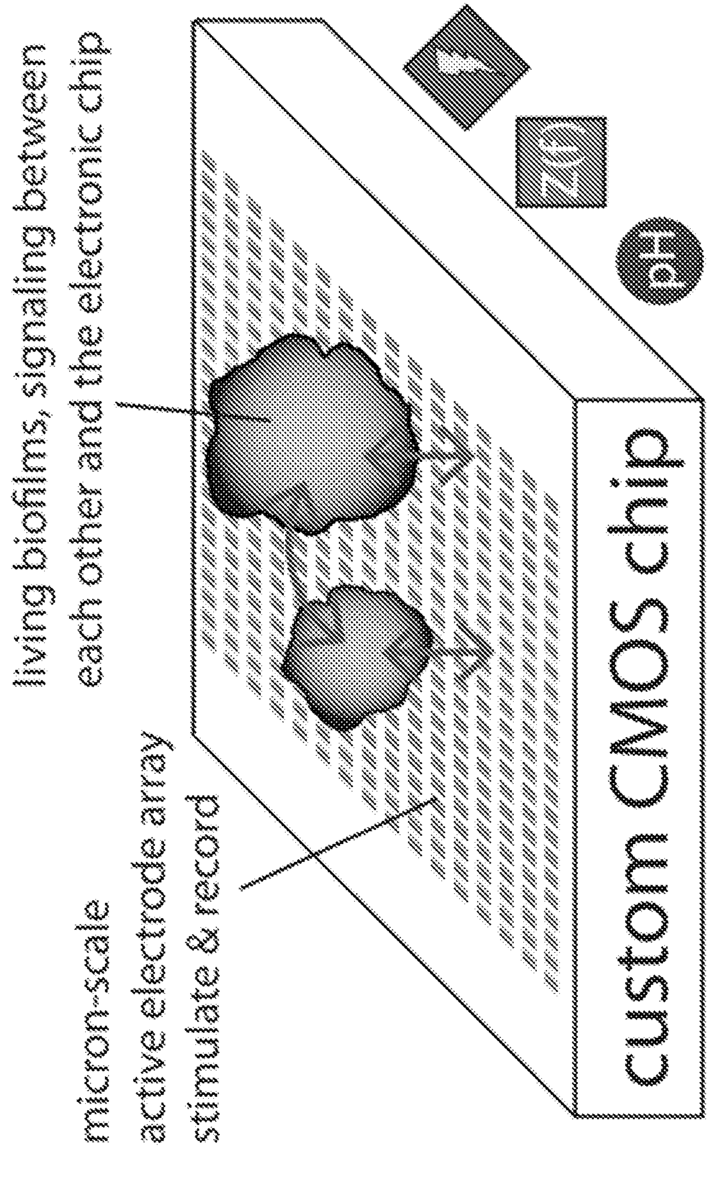
FIG. 4 provides an example protocol of culturing of *B. subtilis* biofilms on custom active microelectrode arrays, and electrical exchange of information between the microelectronics and living biofilms.

Biofilm electrical signals can also facilitate inter-community information exchange. When two biofilms that engage in signaling live in close proximity to each other, they can synchronize or desynchronize their signaling dynamics depending on nutrient conditions[18] (FIG. 3A, 3B, 3C). This desynchronization (e.g., FIG. 3C) allows further nutrient sharing: desynchronizing electrical pulses prevents adjacent biofilms from growing at the same time and having to take a smaller share of available nutrients. The biophysical mechanism of this biofilm-to-biofilm signal is still unknown.

The biofilm electrical signaling process represents two remarkable computations performed by bacterial communities at two different scales: (1) biofilms take nutrient levels as input, and generate an electrical signal when levels become low in the interior and (2) separate communities take collective nutrient levels as input and decide whether or not to synchronize their activity. By studying and manipulating these signaling processes, we can create flexible new tools for biological information processing and bioelectronic interfaces.

There are many examples of using custom CMOS chips for advanced bioelectronics. Applications in neuroscience can achieve high channel count and small physical size[19,20,21,22,23,24,25,26,27,28,29]. These arrays often combine stimulation and recording features[27,30] Many newer DNA sequencing systems also incorporate custom CMOS designs, especially for sequencing strategies which are electrochemical rather than optical[31,32,33,34,35]. There are of course many applications of high-performance imaging sensors, and there have been a number of intriguing systems designed for multi-modal cell culture monitoring[36,37,38,39,40,41].

Requirements for biofilm electrophysiology lie somewhere in between the needs of neural recording and cell culture. Bacteria cells are quite small, on the order of one micron, and thus far, extracellular electrical waves observed in biofilms are much slower than well-known neural signals. Single-unit 'spike' recordings in bacterial biofilms are unlikely, and instead we aim to measure extracellular signals that change on the scale of several seconds. This is a mixed blessing, as it pushes questions about signal fidelity into much lower bandwidths than neural applications, emphasizing low drift rather than low thermal noise. Important parameters to measure as a function of time will include the positions and outlines of each colony, extra-cellular ion concentrations, potential gradients, and local pH. Fine spatial resolution will be important for both stimulation and recording, but the measurable electrochemical signals are extracellular, and represent a collective response of multiple nearby cells. When necessary, monitoring intracellular response is still better matched for fluorescence microscopy.

3.1 CMOS-Biofilm Platform

Our first goal is creating new embedded systems which support electrical information exchange with living biofilms. We design circuits using commercial CMOS semiconductor technology which can electrically stimulate biofilms, image the growth and response of the biofilms, and record transient electrochemical biofilm signaling. The chip will be combined with microfluidic chambers to control the environmental conditions for biofilm growth, and we correlate our measurements against fluorescence imaging where possible. Our goal is to establish spatially resolved bidirectional electrical sensing and stimulation of living biofilms, at faster timescales and at lower cost than would be possible with optical microscopy.

Sub-aim 1.A. Multi-modal sensor circuit design: We design active electrode arrays on CMOS which achieve several goals: (1) spatially resolved images of growing bacterial biofilms, (2) real-time programmable densely patterned electrical stimulation, and (3) spatially resolved mapping of electrochemical potential fluctuations, pH, and ion gradients. A first active array will target 100,000 pixels at approximately 10 μm pitch, and a second-generation array will target 1 million pixels.

Electrical imaging of growing biofilms will be achieved with radio-frequency dielectric imaging. A biofilm's dense community of cells and extracellular matrix contrast with the surrounding media, and can be detected by their dielectric properties. Electrochemical impedance spectroscopy (EIS)[42,43] has previously been used to detect[44] and image cells, although at traditional kHz frequencies EIS faces challenges from ion screening effects which limit the accessible sensing distance. We use radio-frequency spectroscopy with switched capacitor sensing electrodes, which we have shown to be effective at resolving colonies of bacteria (see Preliminary Results). At high frequencies (≈100 MHz), dissolved ions are too slow to effectively screen the electrode charge, and as a result the electric field penetrates deeper into the sample, resolving objects farther from the surface.

Figure 5A:
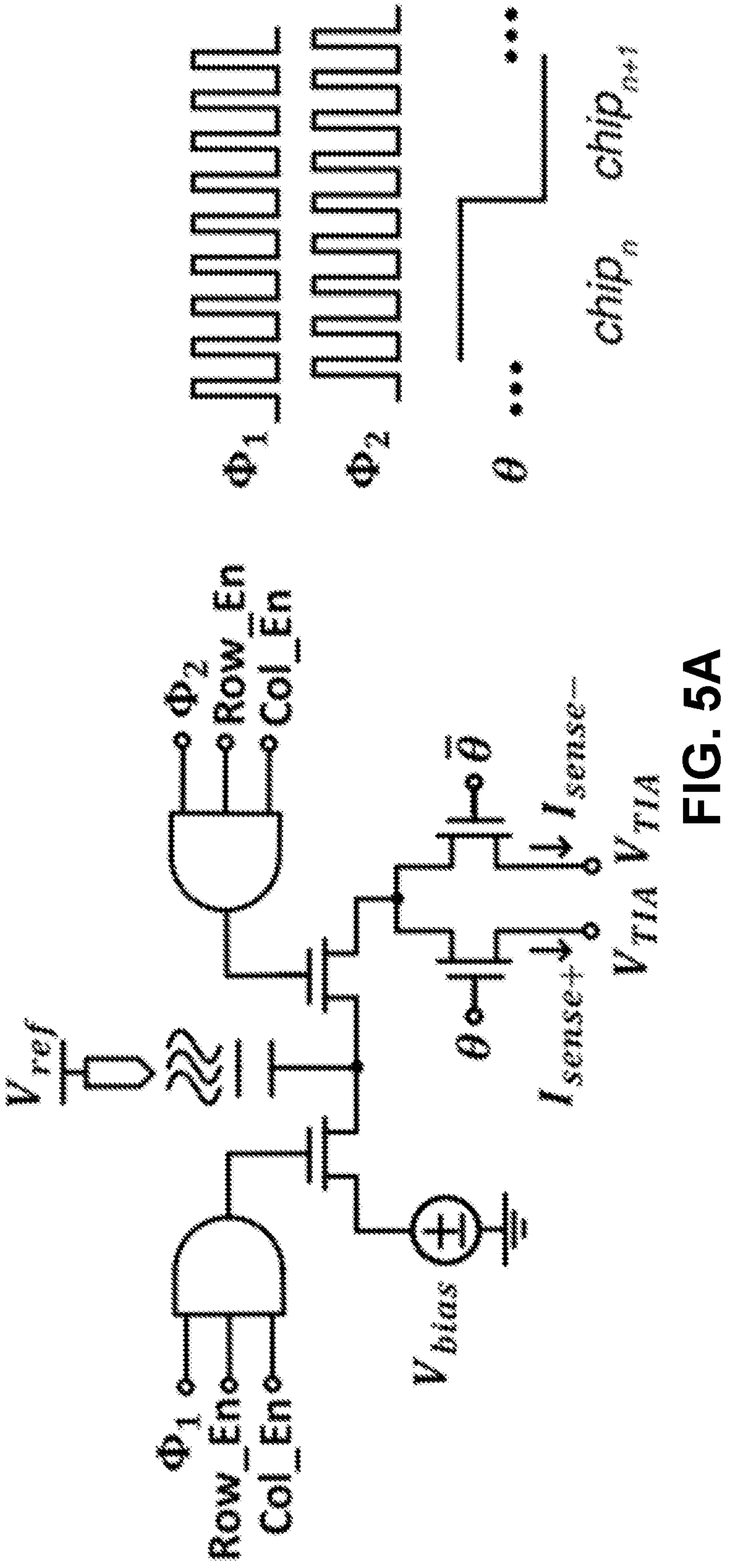
In FIG. 5A illustrates how a radio frequency switched capacitor circuit produces a net current related to the local dielectric properties of the media, cells, and extracellular matrix, for example, when the circuit is included in the example array of FIG. 5B. Code division multiplexing (FIG. 5C) is used to readout many rows concurrently, improving sensitivity without reducing the frame rate.
Figures 5B, 5C:
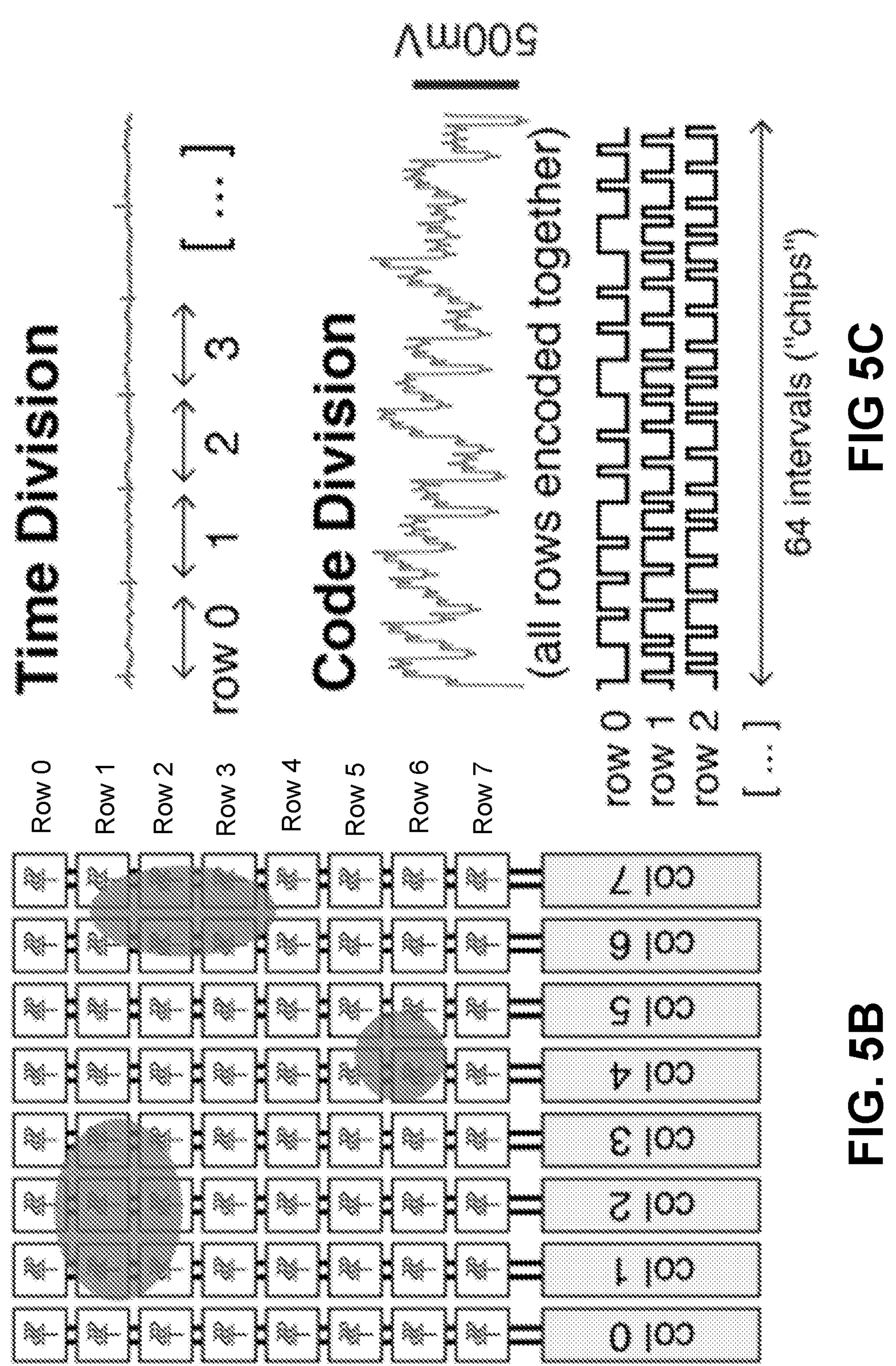
FIG. 5 provides an example circuit, array, and code division multiplexing protocol.
Figure 6:
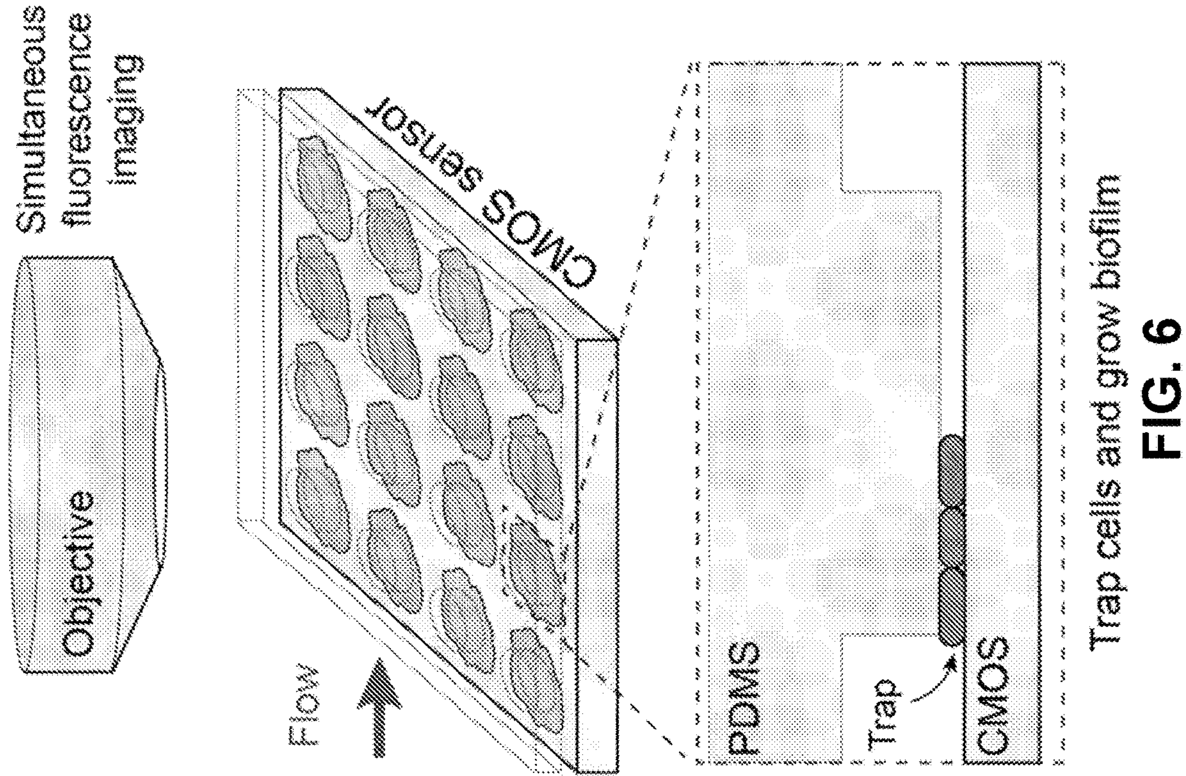
FIG. 6 provides an example protocol showing how biofilm formation can be directed in specific locations on a sensor array by initially trapping a few cells in thin microfluidic pathways. At the top, optional simultaneous fluorescence imaging is illustrated.
Figure 7:
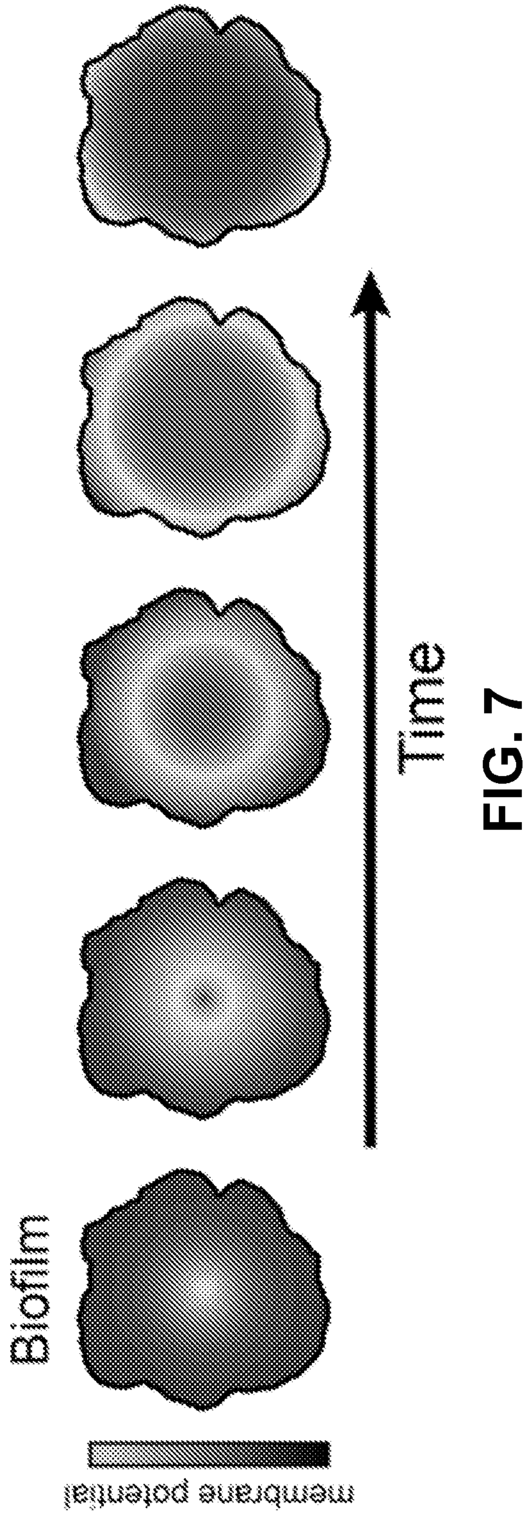
FIG. 7 provides an example of capturing spatial and temporal propagation of electrical potential waves in biofilms. Time is illustrated on the X-axis, and membrane potential is shown by the bar at left.

We combine the RF dielectric spectroscopy with new approaches for code division multiplexed (CDM) readout of large electrode arrays (FIG. 5A, FIG. 5B, FIG. 5C). CDM is a widely used technique in telecommunications[45]. By assigning a unique orthogonal spreading code to each user, CDM enables multiple users to access one channel simultaneously. This concept can also be applied to sensor arrays, enabling concurrent readout of multiple pixels, and overlapping pixel integration times for improved sensitivity[46,47]. We have used CDM multiplexing to read 64 rows simultaneously[46], and this technique will be able to scale up to hundreds of concurrent readout channels.

The CMOS sensing will also support ion imaging, with ion sensitive field effect transistors (ISFETs), whose surface charge depends on local pH and ion concentrations. ISFETs are commonly fabricated in commercial semiconductor processes either by post-processing the chip to deposit a sensing layer such as tantalum pentoxide, or by using the default $SiO_2$ or SiN passivation materials. We create ISFETs by etching away the aluminum top metal, expositing the titanium nitride (TiN) diffusion barrier found underneath the top aluminum metallization in some CMOS processes[48]. Titanium nitride is a robust and non-reactive conductive ceramic with very good pH sensitivity[48,49]. In addition, we also are able to use the same electrodes for low-noise recordings of transient potential fluctuations.

Titanium nitride is also an excellent material for electrical stimulation within biological tissue[50]. We design our electrode array so that pixels can be reconfigured for stimulation or recording. A small, embedded RISC-V microcontroller (PicoRV32[51]) will allow flexible stimulation patterns and real-time feedback between stimuli and measured responses.

Sub-Aim 1.B. Physical Integration of Microelectronics, Biofilms, and Environmental Control:

In order to achieve the goals, we need to (1) grow biofilms at defined locations on the chip and (2) precisely control their ambient conditions. These two capabilities are necessary to determine the electrical signaling mechanisms in detail and ultimately control the signaling process to engineer it for information storage, communication, and computation.

Previous work has used millimeter-scale fluidic chambers to grow, image and perturb bacterial biofilms. We use photolithography to create molds for similarly large chambers, and form PDMS channels from the molds. The PDMS chambers can then be directly bonded to the CMOS array. These devices will have millimeter-scale lateral dimensions but shallow micrometer-scale z-dimensions, in order to create high aspect ratio biofilms, which exhibit stronger electrical activity[9]. To prevent these chambers from collapsing, we make them out of stiff PDMS. The microfluidic chambers will have multiple media inlets for changing ambient conditions during experiments, a cell-loading inlet, and a waste channel. To grow biofilms on the chip, we make several traps in our PMDS chamber. These traps will be pillars inside the chamber whose bases are very close to the chamber floor (i.e., the CMOS array). To load cells, we flow liquid bacterial culture through the system at high pressure. Almost all bacterial cells will flow through the chamber into the waste channel. Some cells, however, will become stuck underneath the pillars. After some time, many cells will have become trapped under the pillars. At that point we release the high pressure, and flow fresh growth media through the chamber to wash out the excess cells. The cells that were trapped underneath the pillars will remain there and begin to grow. After some time, we switch the flow to biofilm-forming media[15]. The initial colonies will then form biofilms with cells stuck together by extracellular matrix and we are ready to begin experiments and switching media between the different inlets using a syringe pump system.

We integrate our semiconductor system with fluorescence imaging, using an upright 'macroscope' imaging system to simultaneously image fluorescent probes in biofilms while they are on the CMOS sensor. Macroscopes combine large fields of view with high fluorescence sensitivity and are used to image gene expression in whole tissues or organisms. With this system, we are able to monitor gene expression in *B. subtilis* biofilms with fluorescent reporters while measuring electrical activity and pH with our sensor chip.

3.2 Studying Electrical Information Exchange Among Communities of Bacteria In Biofilms Our second goal is to use active microelectrode array to understand the underlying mechanisms and dynamics of biofilm electrical signaling. We grow *B. subtilis* biofilms directly on our semiconductor chips. With this system, we probe biofilm information exchange in multiple key ways: we stimulate electrical activity by applying addressable voltage or current-mode excitation through the microelectrode array; we spatially measure biofilm growth with on-chip dielectric imaging (FIG. 14A, 14B, 14C), and we measure metabolic state by measuring pH, which has a significant influence on bacterial metabolism. Using simultaneous fluorescence imaging while bacterial communities are growing on the sensor (see Aim 1B), we monitor gene expression in *B. subtilis* biofilms with fluorescent reporters while measuring electrical activity and pH with our chip. This will allow us to spatially correlate electrical and metabolic activity with cell types that naturally arise during biofilm development[52,53]. Electrical signals may, for example, alter patterns of cellular gene expression by activating ion-responsive kinases[54]. We measure these patterns of gene expression across both space and time. If we find genes that are regulated by electrical biofilm signaling, this will not only change the way we think about biofilm development, but it could also inspire new mechanisms for electrically programming living bacteria. We are also able to measure dynamic intracellular and extracellular electrical responses to electrode stimulation using fluorescent membrane potential reporters.

Sub-Aim 2.A. Elucidate Intra-Biofilm Electrical Signaling:

We use our system to probe electrical activity within biofilms on fast time scales. Up to this point, we have only measured electrical signaling with fluorescence. Due to phototoxic effects, we can only take one fluorescence image every few minutes. The semiconductor sensor will be able to measure extracellular electrical signaling on much faster time scales, limited only by the measurement noise floor. Similar to the generation of local field potentials (LFP) in neural systems, when biofilm cells depolarize and hyperpolarize to propagate electrical signals, ionic currents flow between the cells and the extracellular environment. It is not known exactly how fast biofilm extracellular potentials may change, but our CMOS sensor platform will have the capability to measure localized changes in extracellular potential on millisecond time scales.

Our first experiments focus on measuring intra-biofilm electrical signals. We grow biofilms under conditions that promote electrical signaling and kick off the signaling process with chemical perturbations. Specifically, we flow a pulse of high potassium concentration, which depolarizes the entire biofilm and initiates an electrical pulse. We then monitor the extracellular potential with the CMOS microelectrode array. With these experiments, we hope to observe some of the faster localized dynamics of cellular depolarization-hyperpolarization that underlie slow biofilm-level oscillations. We repeat these experiments with mutant strains that exhibit different electrical properties, for example, strains lacking potassium pumps or ion channel gating domains[9]. These experiments will isolate mechanisms that govern electrical communication. Moreover, we are then able to probe electrical dynamics on the natural timescales of ion channel gating and potassium pumping efficiency.

Next, we demonstrate how electrical signaling emerges from nutrient starvation, which we know from previous work is deeply connected to bacterial electrical activity. Ion channels enable fast changes in cellular physiology by opening and closing on millisecond timescales. If nutrient concentration drops rapidly, biofilms may use ion channels to react quickly and engage a different physiology to quickly adapt to the new conditions. To demonstrate this, we grow biofilms in the microfluidic device, and rapidly switch between normal growth media and nutrient poor media. We monitor electrical activity through the electrode array during these switches, and correlate sudden nutrient shifts to the latency and magnitude of electrical activity. To identify the electrical signaling mechanisms at work in this process, we then perform the same experiment with mutant strains that are deficient in electrical activity. These experiments are essential to understand and model this signaling process, and they can only be performed with our new system.

Figure 8:
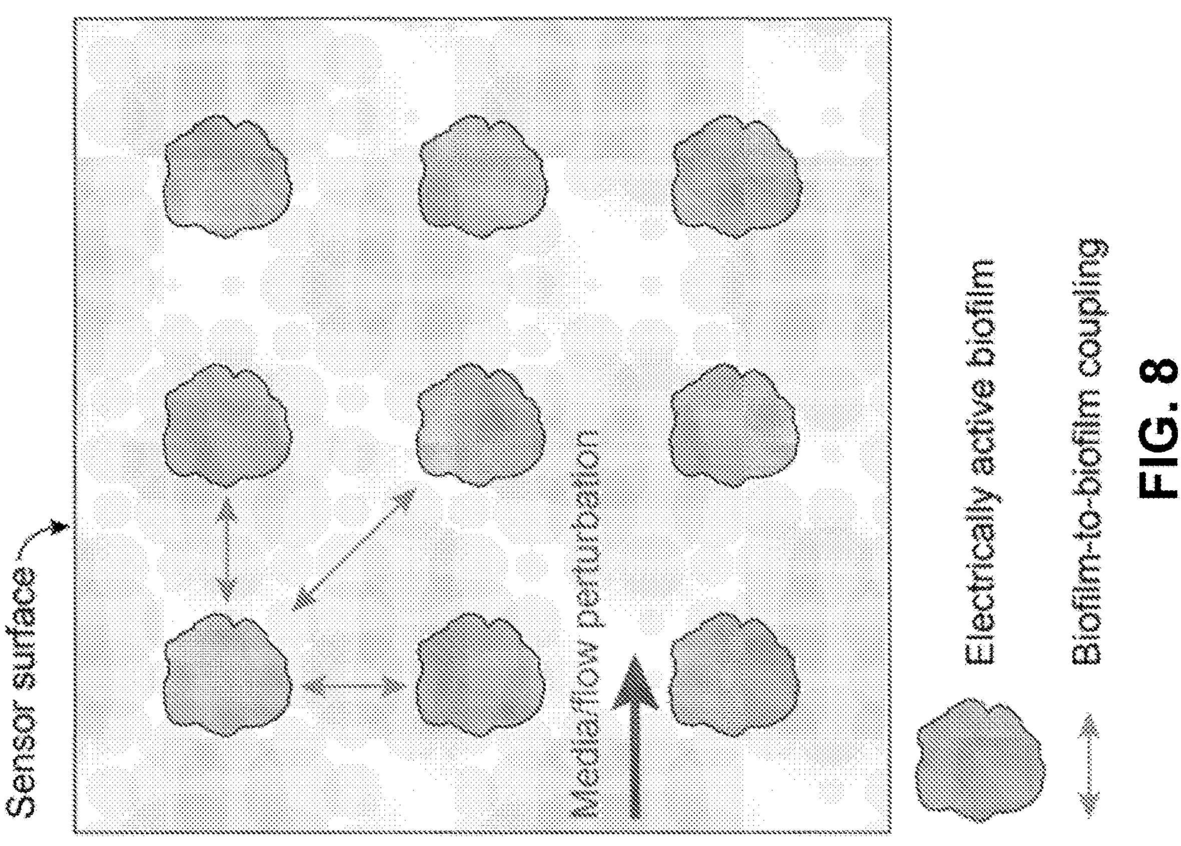
FIG. 8 provides an example of multiple biofilm-to-biofilm coupling (double arrows).
Figure 9:
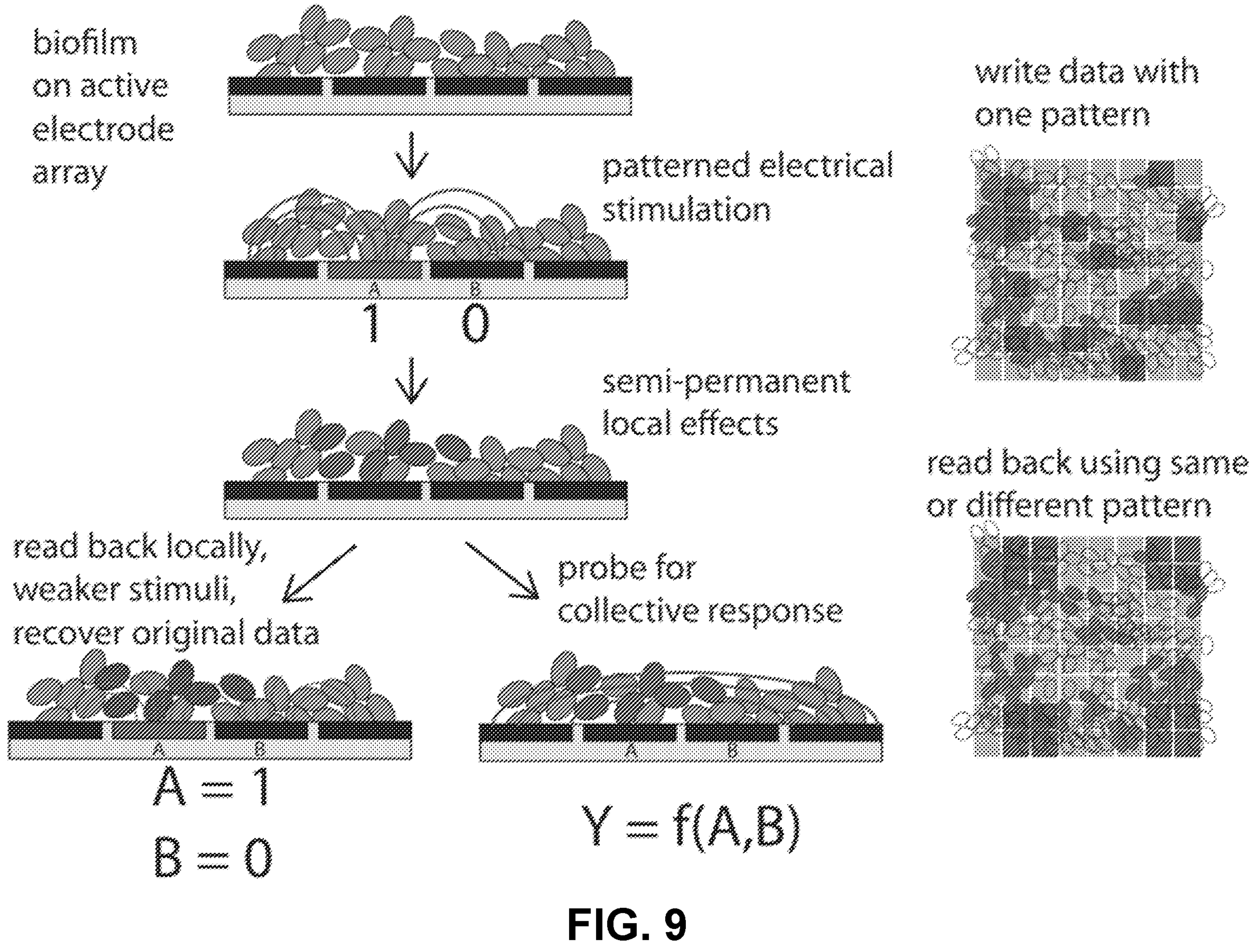
FIG. 9 provides an example method of data read/write capability including biofilms as supported by the preliminary results including FIG. 12C and FIG. 12D.

Sub-Aim 2.B. Coupling of Multiple Biofilms:

A sensor area of 25 $mm^2$ is large enough to grow many biofilms at once. This offers a new opportunity to measure biofilm-to-biofilm coupling. When biofilms are grown within the same chamber and allowed to electrically oscillate, they will either synchronize or anti-synchronize their oscillations depending on nutrient conditions[18] (FIG. 3A, 3B, 3C). We use our semiconductor system to electrically probe this phenomenon. First, we grow multiple biofilms in the same chamber at specific locations that we can control with microfluidics. We grow these biofilms under conditions where they will electrically oscillate and synchronize. We then switch to media that promotes anti-synchronization (e.g., FIG. 8). We measure the fast electrical activity underlying desynchronization, and the rate at which activity becomes desynchronized between biofilms.

We also measure the relative phases when there are more than two oscillating biofilms in the device. If two biofilms become anti-synchronized in order to share scarce nutrients, more than two biofilms may react in similar ways. We elucidate the effects of the distances between biofilms, their relative sizes, and their metabolic states. The complex network of equations resulting from multiple coupled metabolic oscillators has connections to some mathematical questions in statistical physics, which will be discussed in Aim 3.

Sub-Aim 2.C. Electrically Stimulated Biofilm Activity

Our CMOS system will have more than 100,000 active microelectrodes, supporting programmable electrical stimulation with complex spatial and temporal profiles. Related techniques have been used to probe neurons, for example to measure the speed of action potentials in nerve cell networks[55]. Extracellular voltage pulses can depolarize cells and initiate electrical activity. This gives us an opportunity to explore how bacterial electrical waves propagate, with a long-term goal of achieving the same level of understanding that we have of neuron electrophysiology. We apply voltage or current waveforms to electrodes and measure the response from biofilms both electrically and with fluorescent voltage reporters. The electrode measurements will reveal fast dynamic response to electrical stimuli, while fluorescence measurements will show the long-time scale membrane potential response. We first use this system to measure the minimal number of cells that must be stimulated to generate a collective traveling wave. We can perform this unique experiment in our system because each biofilm will align with hundreds or thousands of microscale electrodes. Each microelectrode will primarily stimulate only the small handful of cells adjacent to it. By observing the stimulation response of biofilm segments of increasing sizes, we find how large an area must be stimulated to trigger a traveling pulse.

Next, we use our stimulate-and-measure system to study the relationship between metabolic state and susceptibility to electrical excitation. Spontaneous biofilm electrical oscillations arise from starvation in the biofilm interior, suggesting that cells are more electrically excitable when they are in a state of nutrient limitation. We use the stimulation and pH-measurement capabilities of our device to empirically test this hypothesis. Electrical communication in *B. subtilis* biofilms begins after biofilms have reached a critical size and interior cells have ceased growth[56], a transition thought to arise from metabolic reactions altering environmental pH[57]. We use our system to spatially measure these metabolic pH transitions as biofilms grow. As pH shifts begin in the interior of biofilms, we apply stimulation pulses of different magnitude and frequency. We observe the response both with the on-chip electrodes and with fluorescent voltage reporters (FIG. 2A, 2B). From these experiments, we create a map between metabolic state and susceptibility to electrical stimulation. Spatially distributed biofilm metabolism may lead to electrical heterogeneity that is beneficial for information processing, just as heterogeneities in neural networks allow them to more efficiently process incoming signals[58].

3.3 Writing, Reading, and Computing on Abstract Information with Biofilms

Our third goal provides new approaches for electrically writing and reading back information from biofilms, and using these information exchanges for computations within the biofilm. In the abstract, consider that each bacterium is a metabolic factory with an almost certainly large number of possible chemical states. For instance, the number and type of expressed genes result in a combinatorially large statespace, not to mention the physical arrangement and state of all of the cell's proteins, metabolites, lipids, and nucleic acids. Despite their genetic similarity, individual cells in a community of bacteria will have many differences between them at any given moment. These unique states represent the collective and distributed memory of the bacteria.

So, it is natural to ask how many states we can identify in communities of bacteria. Similarly, we induce the biofilm to change its state(s) in ways that can be later retrieved. Finally, we create programmable computations among the spatially distributed community of cells.

Sub-Aim 3.A. Electrically Writing and Reading Information from Biofilms:

We know that electrical stimulation of biofilms can have long-term effects on the structure and behavior of the biofilm and individual bacteria cells (see FIG. 12A, 12B, 12C, 12D), but we do not yet have a quantitative understanding of these effects. Thus, as part of the research we evaluate the speed, density, precision, and retention time of information written into biofilms via localized electrical stimulation.

Individual bacterial cells are on the order of 1 μm, suggesting that writing hundreds of thousands of bits of data across a 25 $mm^2$ biofilm seems plausible as a short term goal, even if that assigns (on average) less than one bit per cell and is thus quite far from fundamental limits. Our microelectrode grid is likely to have 5-10 μm pitch, which may imply that any stimulus could affect dozens of cells, although the exact effects will depend on the intensity and shape of the induced current, which can be varied with the stimulation intensity, frequency, and waveform. To read back the encoded information, we can use the sensor array to detect local changes in conductivity and dielectric properties, which may change after stimulus due to changes in membrane permittivity. Recognizing that electrical stimulation can affect ion channels and enzyme activity, we can also look for local changes in pH and oscillation phase during metabolic cycles.

Sub-Aim 3.B. Computing with Biofilms:

The electrical and metabolic coupling between cells within a biofilm, and the coupling of oscillations between neighboring biofilms, provides an opportunity to explore the use of biofilms as a novel substrate for computing. We propose two directions for computing using biofilms.

Figure 10:
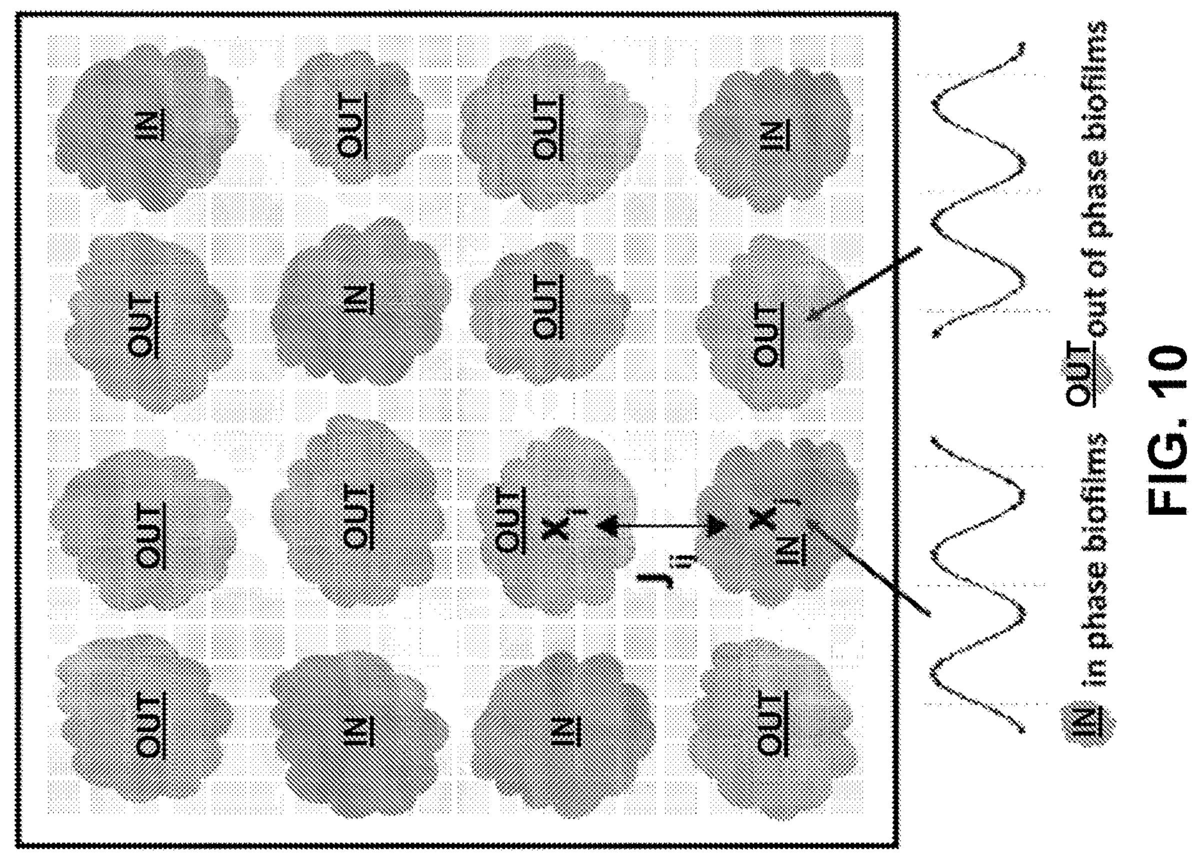
FIG. 10 provides an example setup of an Ising model using an array of coupled biofilms. In phase biofilms and out of phase biofilms are indicated by different shading.

1. Using Biofilms to Compute Solutions of the Ising and XY Models. A wide range of physical phenomena, including magnetism in 2D materials[59] and the absorption of atoms and molecules on 2D surfaces[60], can be described by classical, 2D lattice models, such as the Ising and the more general XY model. All such models are NP-hard problems whose solutions have long posed a challenge to statistical physicists[61]. The Ising model describes a 2D lattice of interacting sites or elements that can assume discrete configurations, such as up or down spins[60]. Neighboring elements are coupled through an interaction term, $J_{ij}$, where i and j denote elements of the latice. Each element may also be influenced by an external (e.g., electromagnetic) field, $h_i$. The goal is to identify the configurations that minimize the total energy, H:

$$H = -\sum_{\langle i,j \rangle} J_{ij} x_i x_j - \sum_i h_i x_i, \quad \text{(Eq. 1)}$$

where $x_i \in \{-1, 1\}$ denotes the configuration of element i. If the biofilms are associated with Ising model elements and their oscillations are associated with the configurations of those elements, we observe that the coupling of oscillations between the biofilms can be exploited to map an Ising problem onto a biofilm array. Given an N×N Ising model, we can create corresponding arrays of biofilms on the surface of our CMOS sensor chip as illustrated in FIG. 10, where $x_i=1$ correspond to an in-phase oscillation, and $x_i=-1$ corresponds to an out-of-phase oscillation. We can then let the biofilms naturally explore the set of phases that minimizes competition and optimizes the usage of global nutrient resources.

When steady-state is reached, we can read the phases of the biofilms using the CMOS sensors. This readout corresponds to the desired solution of the original Ising model. We experimentally characterize the upper bound for N, which will depend on the size of the CMOS chip and the minimum size of the biofilms required to sustain oscillations. Previous experiments give us confidence that arrays of 5×5 or larger can be designed, placing our biofilm arrays within range of solving statistically interesting, yet computationally expensive problems.

Given the unchartered territory of our proposed ambitious experiments, we plan to adapt our plans depending on the observed results. We entertain the following two scenarios. In the first scenario, the coupled oscillations between neighbors within an array behave similarly to the two biofilm case; i.e., each biofilm is either in phase or out of phase. This outcome is perfect for the Ising model. In the second scenario, the biofilms in the array instead assume arbitrary relative phases in order to further minimize their total energy. This generalization of the Ising model is referred to as the XY model in the statistical mechanics literature[62]. In the XY model, each element can assume an arbitrary phase which is accounted for by generalizing each element's configuration into a 2D vector:

$$\vec{x}_i = [\cos(\theta_i), \sin(\theta_i)],$$

(2D vector)

The coupling term in the Hamiltonian may then be re-expressed as:

$$-\sum_{i \neq j} J_{ij} \vec{x}_i \cdot \vec{x}_j = -\sum_{i \neq j} J_{ij} \cos(\theta_i - \theta_j).$$

(Coupling term in the Hamiltonian)

The XY model is of particular interest to physicists because its behavior can dramatically differ with the strength and range of the interactions among its elements. We plan to explore the stability and bifurcation dynamics of these models as a function of the initial conditions, such as the size of the biofilms, distance between neighbors, array geometry, and initial levels of glutamate and other nutrients.

2. Using Biofilms as Analog Solvers of Distributed Dynamical Systems.

As described in Section 2, the spatial propagation of electrical signals along the biofilm leads to a distributed negative feedback system with time lag. This lag arises from the slow propagation of stress markers from the inside of the biofilm to its periphery. Depending on the parameters of the biofilm and its environment, this negative feedback can lead to oscillations. If y(t) denote the electrical activity at time t at the periphery of a single biofilm then the dynamics of this activity can be described using the following non-linear dynamical equation:

$$\frac{dy}{dt} = f(y(t-\tau)) - \delta y, \quad \text{(Eq. 2)}$$

where f(·) is a function that models the stress production rate, T is the time delay parameter, δ is the linear degradation rate[63]. Typical forms for f(·) are modeled based on the Mackey-Glass function.

Given the interesting non-linear dynamical behavior of biofilms, we propose the use of the biofilms array as an analog solver for special classes of distributed dynamical systems, where the dynamical behavior of each component in the system is governed by the form of Eq. 2. In our experiments, we plan to start with the simple case of a single biofilm. Given the mathematical expression of a dynamical system, we plan to create a mirror setup with biofilms such that the parameters of the setup lead to the same mathematical expression as the given system. Using the global nutrient level and the CMOS electrodes, we set the initial conditions for the biofilms. We let the system dynamics evolve naturally and then measure the electrical activity at the periphery. These experiments leverage the dynamics of the biofilm to physically solve general dynamical systems with the mathematical form of Eq. 2. In subsequent experiments, we plan to set up multiple biofilms on the CMOS array, and leverage the coupling through the environment to explore solving distributed dynamic systems[64]. We evaluate the system bifurcations and chaotic behavior as a function of environmental parameters and initial conditions. Preliminary results begin in Example 1 below.

In providing examples, the present invention, in one of its broadest embodiments, provides a CMOS (complementary metal-oxide semiconductor) chip comprising: an array of pixels, each pixel comprising a circuit operative to measure from and/or to apply an electrical charge and/or impedance to at least a portion of a live biofilm disposed on the array; the living biofilm disposed on the array, wherein a portion of the biofilm is in discrete electrical communication with each pixel; and a circuit in electrical communication with the array, said circuit operative to provide at least one signal for each pixel.

In some embodiments, the CMOS chip can be configured as any semiconductor chip. In some embodiments, the chip can be configured wherein each pixel comprises at least one circuit operative to perform a function selected from stimulate, heat, impedance image, measure pH, ion imaging/ measurement, temperature measurement, stimulation, measure an amperometry, measure a voltage, measure a resistance, and measure an impedance tomography, of a portion of a biofilm.

According to some aspects, the (CMOS) chip can further comprise a reference electrode and a hydrogel disposed over the biofilm.

In some embodiments, the (CMOS) chip can be configured wherein the biofilm includes at least two biofilms, each of the at least two biofilms in communication with another of the at least two biofilms, wherein the communication comprises a signaling and/or a coupling between biofilms. According to some aspects, the biofilm can comprise a genetically modified cell, a combination of cells, and/or a genetically modified strain of bacteria.

In some embodiments, the (CMOS) can further comprise (or be in further electrical communication with) a processor, memory, programming instructions, and/or display operative to read, store, and display at least one measurement, charge, and/or impedance from the array.

In some embodiments, the (CMOS) chip can be configured wherein the chip is operative to apply an electrical stimulation to a pixel including the biofilm disposed on the pixel, the electrical stimulation comprising at least a bit of information provided in a current/voltage stimulation, and said biofilm is operative to store the bit for a period of time. In this example, the bit of information can be read from the biofilm by applying at least an impedance measurement, a resistance measurement, an amperometry measurement, a current/voltage stimulation, or a combination thereof to the pixel; and wherein the biofilm is capable of changing at least one bit by a cell-to-cell and/or a biofilm-to-biofilm interaction. The change can be a computation using the living biofilm as a processor or computer.

In some embodiments, the chip is configured as an imaging chip capable of imaging the biofilm including computed tomography and/or impedance imaging of the biofilm, and wherein each pixel represents an imaging pixel.

According to some aspects, a method for measuring at least one aspect of a biofilm is disclosed herein, the method comprising the steps of:

(1) obtaining a CMOS (complementary metal-oxide semiconductor) chip comprising:
  - an array of pixels, each pixel comprising a circuit operative to measure from and/or to apply an electrical charge and/or impedance to at least a portion of a biofilm;
  - a biofilm disposed on the array, a portion of the biofilm in electrical communication with each pixel; and
  - a circuit in electrical communication with the array, said circuit operative to provide at least one signal for each pixel;

(2) applying a current and/or voltage to a biofilm directly disposed on a pixel, whereby the current and/or voltage is in electrical communication with at least a portion of the biofilm and provides a signal indicative of a condition of at least the portion; and (3) transmitting the signal via an electrical conductor from the pixel to an additional circuitry operative to move the signal from the chip.

The method disclosed above can, in some embodiments, further comprise circuitry in communication with the chip, said circuitry in communication with the chip operative to provide the signal to a processor, memory, field-programmable gate array, DDR3 (RAM/SDRAM), a USB 3.0 output, an analog to digital convertor (ADC), or a combination thereof.

According to some aspects, the method can be performed wherein the (2) applying a current and/or voltage to a pixel is operative to store at least a bit of information in the biofilm. In this example, the at least a bit of information in the biofilm is capable of being read back by a repeating of step (2) and step (3) in any order. The method can be repeated in steps (2) and (3) to different pixels, whereby a plurality of bits of information is applied to discrete areas of the biofilm.

In some embodiments, the method disclosed above changes patterns of a cellular gene expression, intracellular and/or extracellular electrical responses, and/or communication between/among at least one biofilm.

In some embodiments, the biofilm comprises cells/microbes of fungal, bacterial, and/or eukaryotic origin, optionally wherein the cells are derived from *Staphylococcus aureus, Escherichia coli, Streptococcus pneumoniae, Pseudomonas aeruginosa, Bacillus subtilis*, skin (epidermal/dermal) cells, or the archaeal species *H. volcanii*, transfected cells, recombinant cells, genetically engineered cells, normal eukaryotic cells, immune cells such as macrophages, eosinophils, or a combination thereof. According to some aspects, the biofilm includes viruses, culture medium, pharmaceutical agents, prions, oligonucleotides, antibodies, additives, or a combination thereof.

In some embodiments, the technology disclosed herein provides a method for computing within a living biofilm, the method comprising the steps of:

(1) obtaining a CMOS (complementary metal-oxide semiconductor) chip comprising:
  - an array of pixels, each pixel comprising a circuit operative to measure from and/or to apply an electrical charge and/or impedance to at least a portion of a biofilm;
  - a biofilm disposed on the array, a portion of the biofilm in electrical communication with each pixel; and
  - a circuit in electrical communication with the array, said circuit operative to provide at least one signal for each pixel;

(2) applying a current and/or voltage to a biofilm directly disposed on a pixel, whereby the current and/or voltage is in electrical communication with at least a portion of the biofilm and stores a signal indicative of a bit of information in the at least the portion of the biofilm;

(3) repeating step (2) such that a plurality of different bits of information are stored in discrete pixels of the biofilm; and (4) waiting a period of time for an interaction between pixels of the biofilm; whereby said interaction is a computation within the living biofilm.

In some embodiments, the method for computing includes an interaction within the biofilm that is a function.

In some embodiments, the plurality of different bits of information is representative of a problem selected from a 2D lattice model, Ising model, an analog model, and an XY model; and wherein the period of time is sufficient for the living biofilm to change at least one of the bits of information.

The method(s) of computing within a living biofilm, according to some aspects, can further comprise the step of:

(5) repeatedly applying a current and/or voltage to a biofilm directly disposed on a pixel, while changing the position of the pixel, whereby a change in at least one bit caused by the biofilm is detected and such change is representative of a computation performed within the biofilm.

In some embodiments, a screening method for therapeutic agents or a method for evaluating the efficacy or toxicity of a therapeutic agent candidate substance acting on cells or biofilms comprising the methods disclosed above is provided, for example, by flowing or applying various agents and/or additives to the biofilm.

In some embodiments, a method of culturing cells, or tissues, comprising the methods disclosed herein is provided, with the proviso that the methods can be performed with or without including a test condition.

In some embodiments, a quantitative screening method for therapeutic agents or a method for evaluating the efficacy or toxicity of a therapeutic agent candidate substance acting on cells or tissues comprising the methods disclosed above.

In some embodiments, a method of culturing cells, or tissues, comprising the methods disclosed herein is provided, with the proviso that the methods can be performed with or without the a condition.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in The Merck Manual of Diagnosis and Therapy;[65] The Encyclopedia of Molecular Cell Biology and Molecular Medicine;[66] Molecular Biology and Biotechnology: a Comprehensive Desk Reference;[67] Immunology;[68] Janeway's Immunobiology;[69] Lewin's Genes XI;[70] Molecular Cloning: A Laboratory Manual.;[71] Basic Methods in Molecular Biology;[72] Laboratory Methods in Enzymology;[73] Current Protocols in Molecular Biology (CPMB);[74] Current Protocols in Protein Science (CPPS);[75] and Current Protocols in Immunology (CPI).[76]

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

The devices and methods described herein can be implemented including or in any suitable computing system. The computing system can be implemented as or can include a computer device that includes a combination of hardware, software, and firmware that allows the computing device to run an applications layer or otherwise perform various processing tasks. Computing devices can include without limitation personal computers, workstations, servers, laptop computers, tablet computers, mobile devices, wireless devices, smartphones, wearable devices, embedded devices, microprocessor-based devices, microcontroller-based devices, programmable consumer electronics, mini-computers, main frame computers, and the like and combinations thereof.

Processing tasks can be carried out by one or more processors. Various types of processing technology can be used including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, scripts, drivers, objects, components, data structures, and the like that perform particular tasks or operate on data.

Figure 15A:
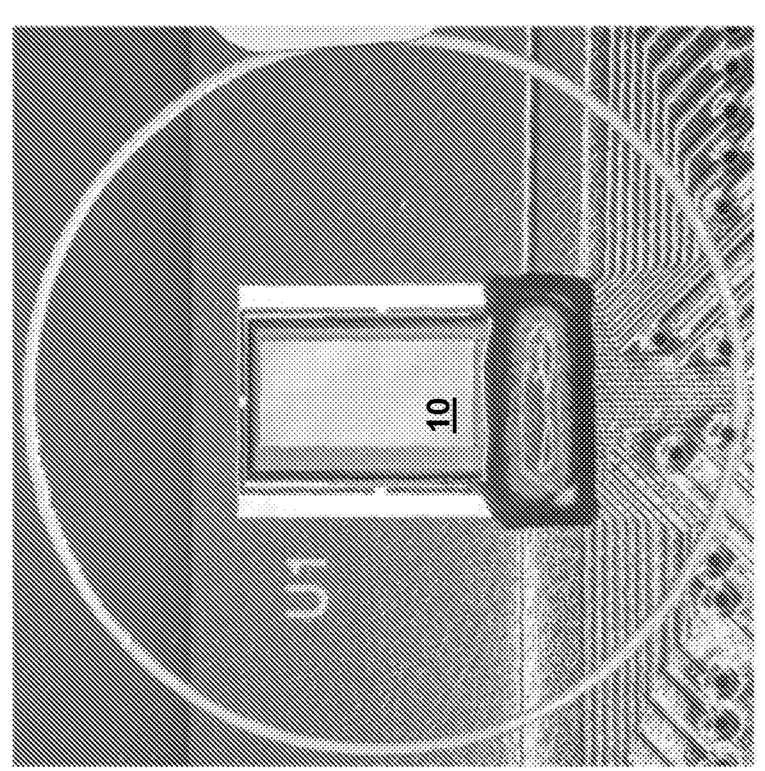
FIG. 15 provides an enlarged image of array chip 10 (FIG. 15A) e.g., compare FIG. 13A, left.
FIG. 15B depicts example circuits/logic surrounding the chip and the 131,072 pixels. Optional added processor 40 and/or memory 50 can be in communication with ADC(s) and/or FPGA.
FIG. 15C provides an example schematic of each 10×10-micron pixel. Example circuitry for biofilm impedance imaging is provided in FIG. 15D. Example circuitry for pH (imaging/measurement) is provided in FIG. 15E. Example circuitry for biofilm temperature (imaging/measurement) is provided in FIG. 15F. Example circuitry for biofilm heating (imaging/measurement) is provided in FIG. 15G. Example circuitry for biofilm impedance tomography (imaging/measurement) is provided in FIG. 15H. Example circuitry for biofilm stimulation (imaging/measurement) is provided in FIG. 15I. Example circuitry for biofilm amperometry (imaging/measurement) is provided in FIG. 15J. In these examples of FIG. 15, each of the 131,072 pixels can be configured for at least impedance, pH, temperature, amperometry, or bipolar stimulation, and heating, while the technology contemplates other interfaces including read/write and computations.
Figure 15B:
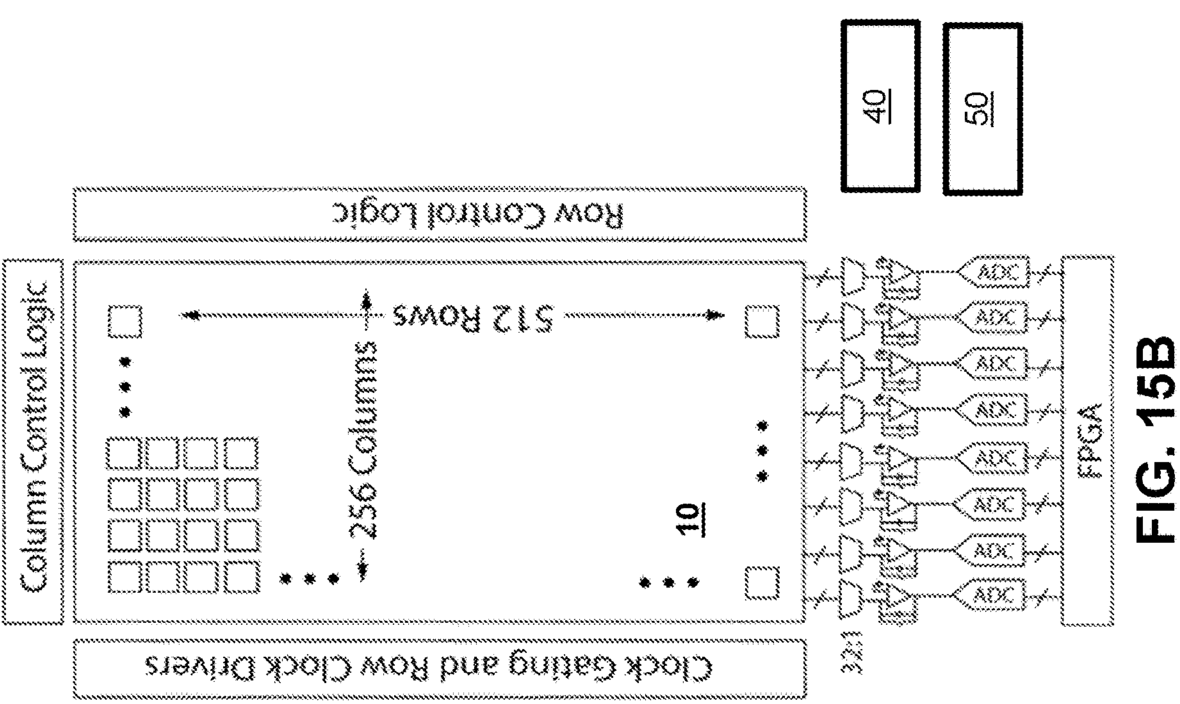
Figure 15C:
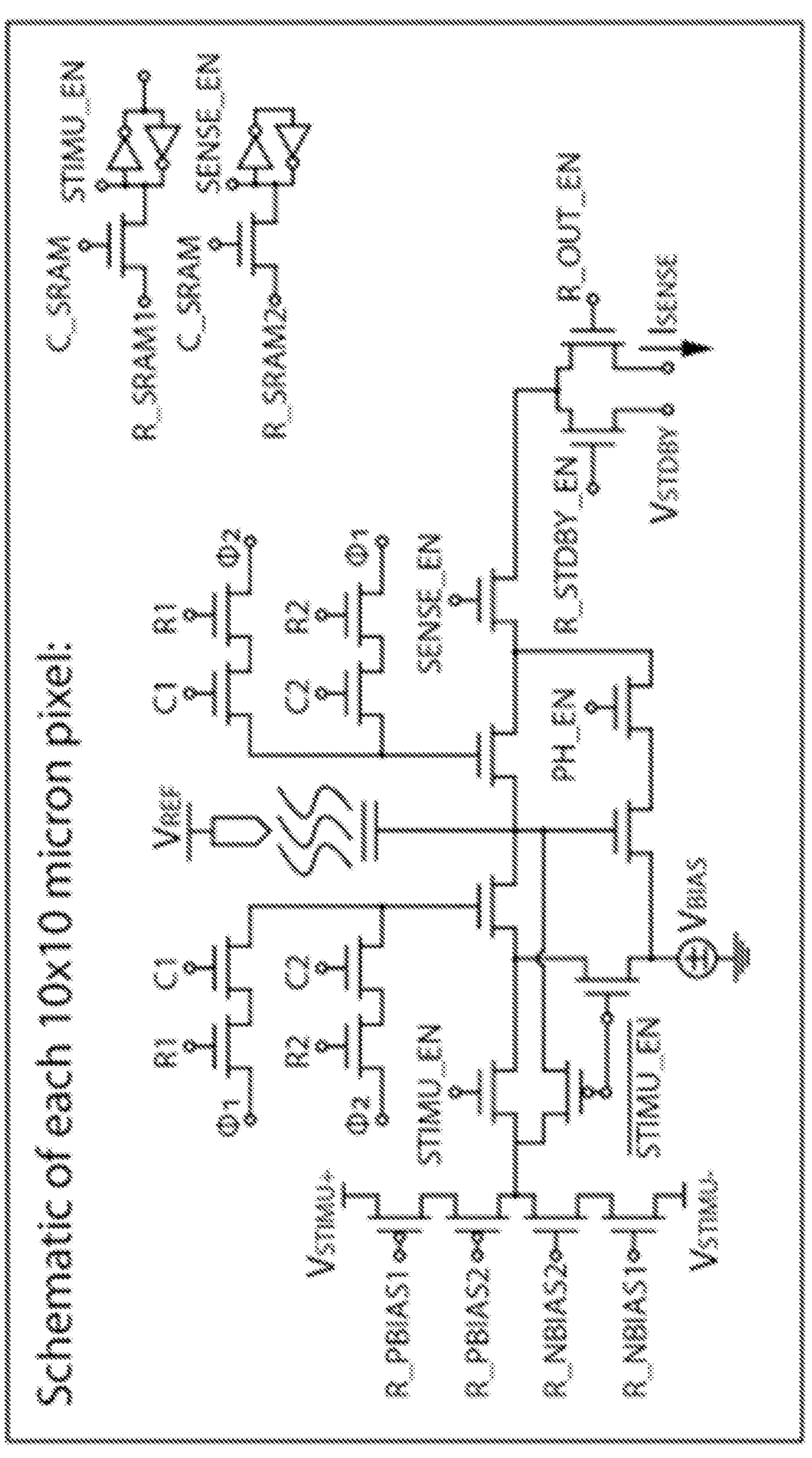
Figures 15D, 15E, 15F, 15G:
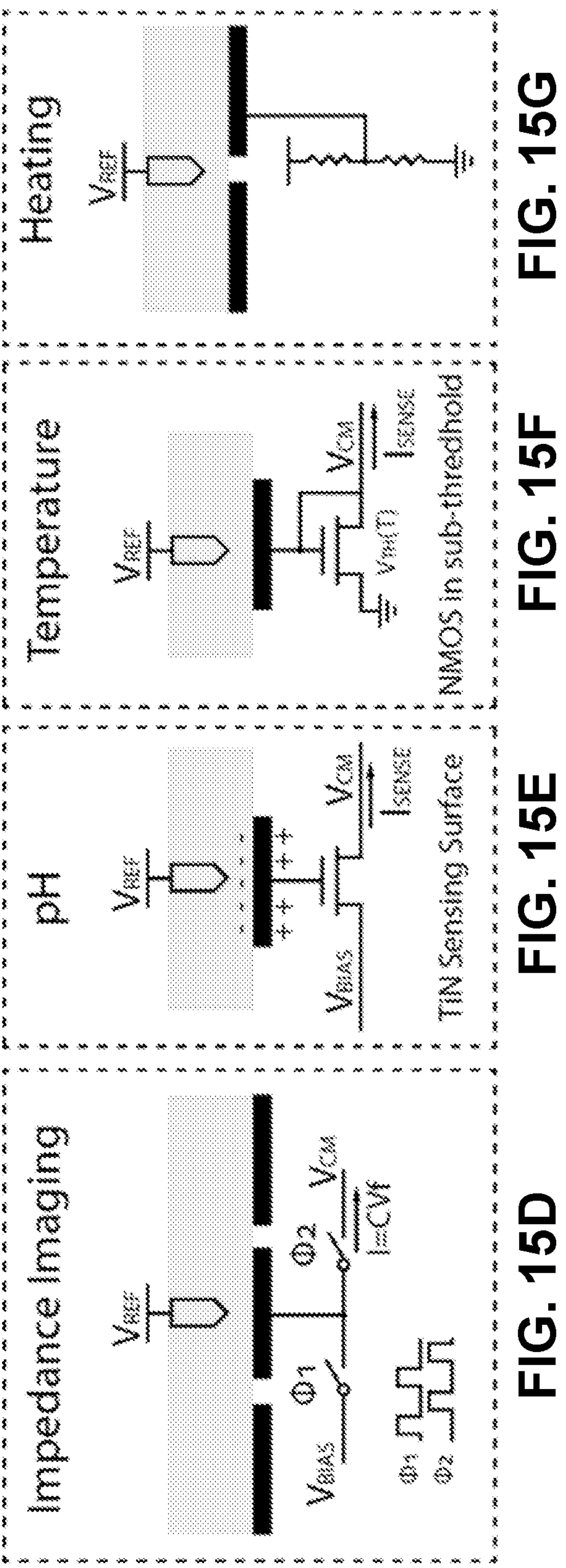
Figures 15H, 15I, 15J:
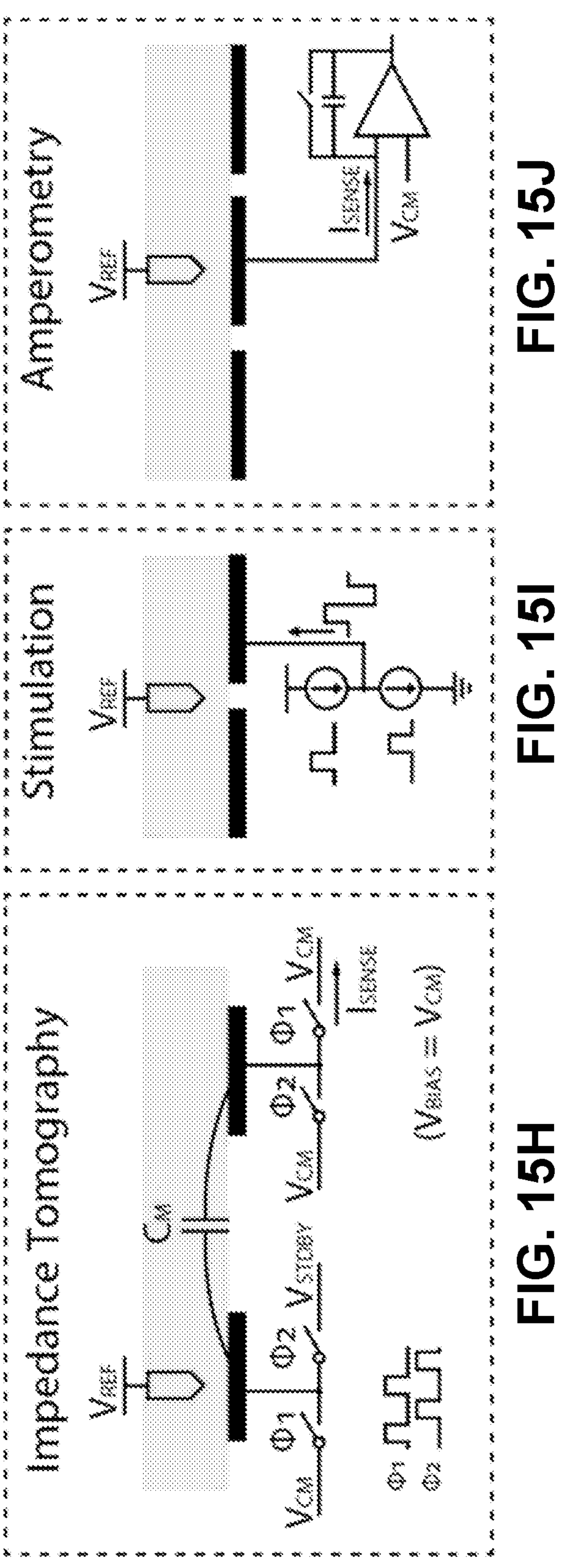

Processors can include one or more logic devices, such as small-scale integrated circuits, programmable logic arrays, programmable logic devices, masked-programmed gate arrays, field programmable gate arrays (FPGAs, FIG. 15B), application specific integrated circuits (ASICs), and complex programmable logic devices (CPLDs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells.

The computing device includes memory or storage, which can be accessed by a system bus or in any other manner. Memory can store control logic, instructions, and/or data. Memory can include transitory memory, such as cache memory, random access memory (RAM), static random-access memory (SRAM), main memory, dynamic random-access memory (DRAM), block random access memory (BRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), one-time programmable non-volatile memory (OTPNVM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the systems and methods described herein. Physical media can include floppy discs, optical discs, CDs, mini-CDs, DVDs, HD-DVDs, Blu-ray discs, hard drives, tape drives, flash memory, or memory chips. Any other type of tangible, non-transitory storage that can provide instructions and/or data to a processor can be used in the systems and methods described herein.

The computing device can include one or more input/output interfaces for connecting input and output devices to various other components of the computing device. Input and output devices can include, without limitation, keyboards, mice, joysticks, microphones, cameras, webcams, displays, touchscreens, monitors, scanners, speakers, and printers. Interfaces can include universal serial bus (USB) ports, serial ports, parallel ports, game ports, and the like.

The computing device can access a network over a network connection that provides the computing device with telecommunications capabilities Network connection enables the computing device to communicate and interact with any combination of remote devices, remote networks, and remote entities via a communications link. The communications link can be any type of communication link including without limitation a wired or wireless link. For example, the network connection can allow the computing device to communicate with remote devices over a network which can be a wired and/or a wireless network, and which can include any combination of intranet, local area networks (LANs), enterprise-wide networks, medium area networks, wide area networks (WANS), virtual private networks (VPNs), the Internet, cellular networks, and the like. Control logic and/or data can be transmitted to and from the computing device via the network connection. The network connection can include a modem, a network interface (such as an Ethernet card), a communication port, a PCMCIA slot and card, or the like to enable transmission to and receipt of data via the communications link. A transceiver can include one or more devices that both transmit and receive signals, whether sharing common circuitry, housing, or a circuit boards, or whether distributed over separated circuitry, housings, or circuit boards, and can include a transmitter-receiver.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network. The computer system can include architecture distributed over one or more networks, such as, for example, a cloud computing architecture. Cloud computing includes without limitation distributed network architectures for providing, for example, software as a service (SaaS).

Any of the devices and/or methods disclosed herein can be configured as implantable (i.e., implantable within a mammal) devices or methods. In this example, a portion of the device/method can be exterior to the mammal. Any of the devices and/or methods can include WiFi and can transmit data either to/from a living mammal.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention and are not intended to limit the invention.

Example 1 Presentation of Preliminary Results (Sec. 3.4)

In this section we present preliminary results which show some of our experience measuring electrical signaling within biofilms using fluorescent dyes and stimulating biofilms with microelectrodes. We also demonstrate a custom CMOS chip design which supports pH sensing and radio frequency dielectric imaging (without stimulation), and which can electrically image living colonies of bacteria.

Figure 11B:
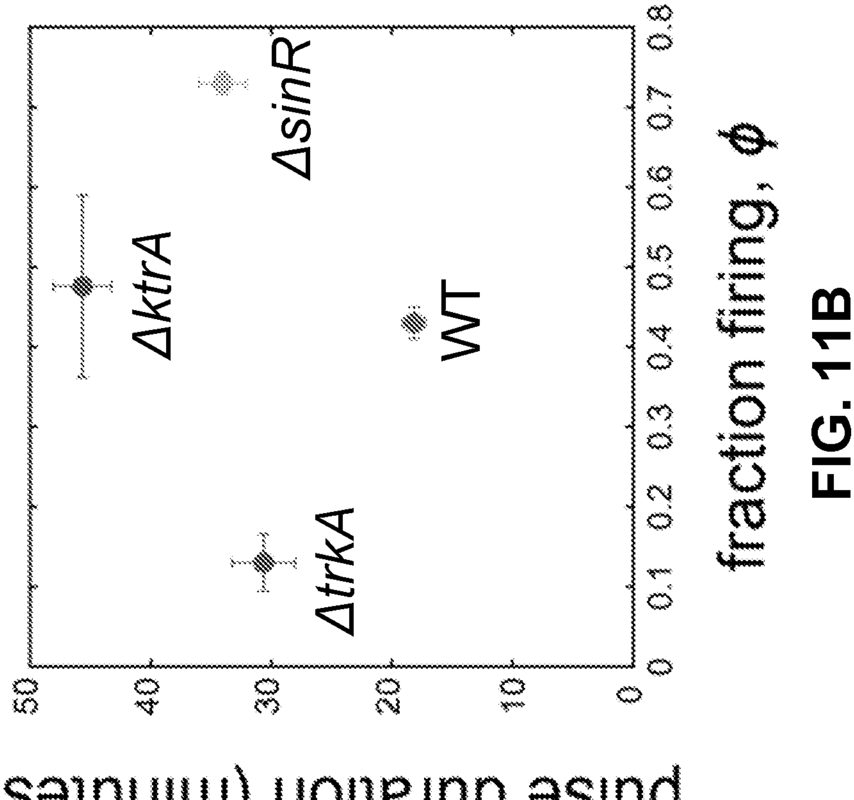
In FIG. 11B, the fraction of electrically active cells and the average pulse time for different *B. subtilis* strains shows an ability to independently manipulate these parameters of signaling genetically.
Figure 11A:
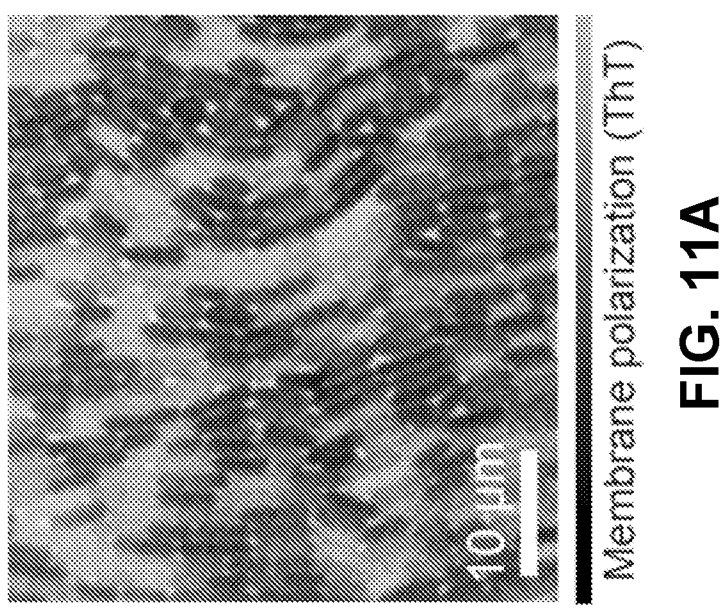
In FIG. 11A, a still image of single cells within a biofilm during signaling (lighter grey shows polarization) shows in this example that only a fraction of cells hyperpolarizes.

Imaging of Electrical Signaling in Biofilms:

We have demonstrated the ability to use fluorescent dyes to image electrical signaling with biofilms, and we have also genetically modified bacteria to affect the signal propagation. Biofilm electrical signaling is heterogeneous at the single-cell-level: some cells carry the signal, and some do not (FIG. 11A). We believe this heterogeneity represents a compromise between the population-level benefit of signaling (more interior cells stay alive) and the individual-level cost (cells that signal must reduce growth). At the single-cell-level, we characterize biofilm signaling with two parameters: the fraction of cells that exhibit a voltage pulse on each signaling wave and the electrical pulse duration (FIG. 11B). By genetically mutating potassium channels, potassium pumps, and transcription factors that regulated ion channel expression, we can independently modulate the two parameters of electrical signaling within biofilms, as illustrated in the plot of FIG. 11B. As a result of their different signaling parameters, biofilms formed from these strains have different efficiencies at propagating signals within and between each other[9,18]

Figure 12B:
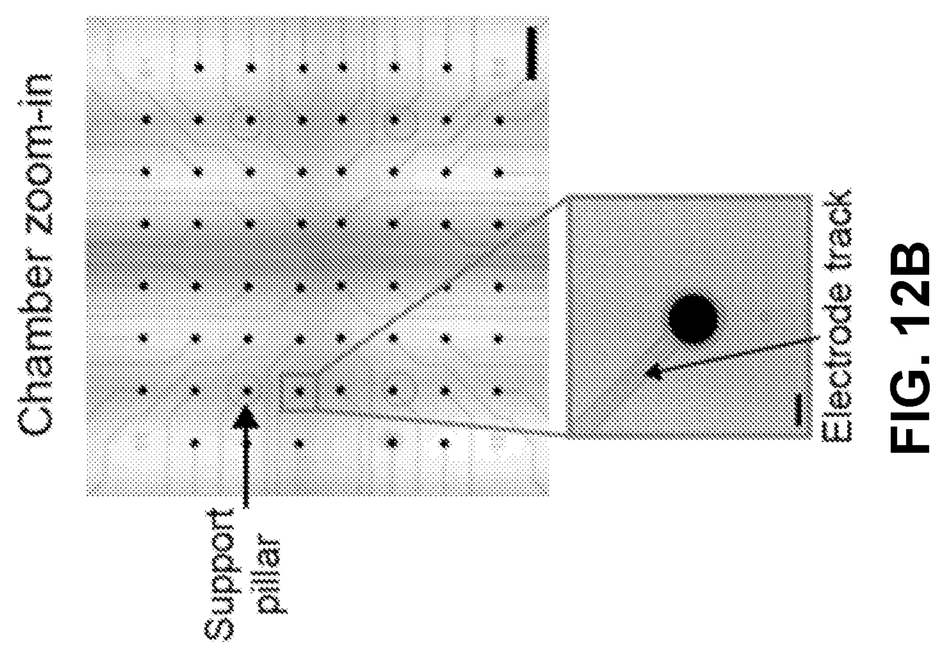
FIG. 12 provides preliminary electrical stimulation results.
In FIG. 12A is shown a photo of the preliminary electrical device, which is a microfluidic system bonded to a commercial microelectrode array chip. A microscope image in FIG. 12B shows 59 available electrodes with 200 μm spacing.
FIG. 12C shows a fluorescence image of biofilm cells with membrane potential dye signal in lighter grey before stimulation.
FIG. 12D shows an image of the same biofilm cells after stimulation showing a local electrical response.
Figure 12A:
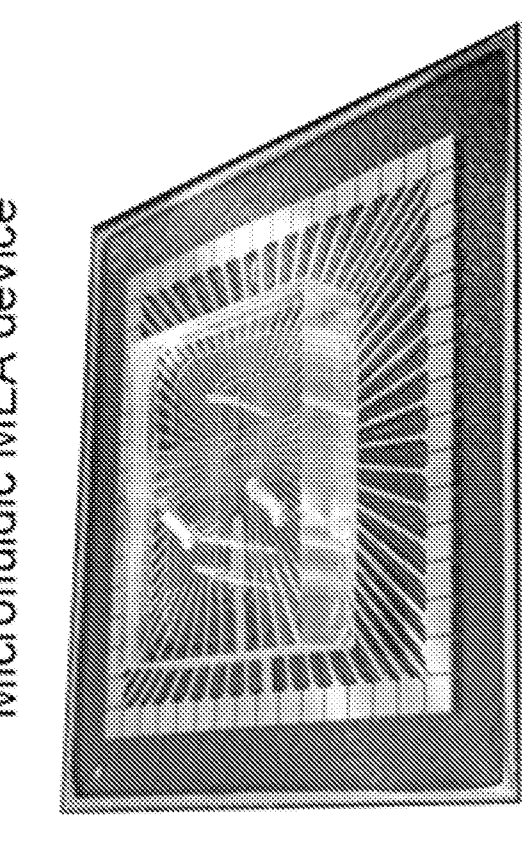
Figures 12C, 12D:
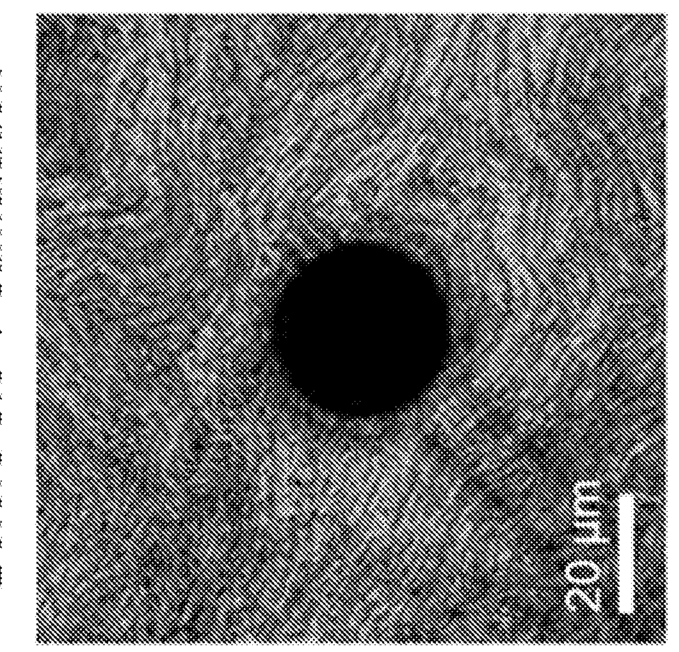

We have previously worked with a system for electrically interfacing with bacterial biofilms. This device consisted of a microfluidic system for biofilm growth mounted on a commercial microelectrode array system[19] (FIG. 12A). In this system, biofilms are integrated with an array of 59 electrodes of 30 μm diameter (FIG. 12B). By combining this system with fluorescent membrane potential measurements, we have shown the ability to electrically stimulate biofilms by applying 1-4-volt pulses to individual electrodes. In the minutes following one of these seconds-long pulses, cells in the vicinity of the electrode undergo a depolarization/hyperpolarization response and then maintain a more polarized electrical state than their immediate neighbors (FIG. 12C, 12D). This demonstrates a preliminary ability to influence biofilm electrical activity. Two major drawbacks of our earlier system are that it contains only 59 electrodes and that these electrodes are 200 μm apart. The semiconductor system will contain more than 100,000 electrodes. This will enable a vast spatiotemporal repertoire of biofilm stimulation patterns to measure and engineer this microbial information exchange process.

Integrated Sensor Design:

We recently designed a multimodal CMOS sensor array for long-term cell culture monitoring which measures radio-frequency electrochemical impedance, pH, and visible light. (However, this chip has no stimulation or biopotential modes.)

Figure 13A:
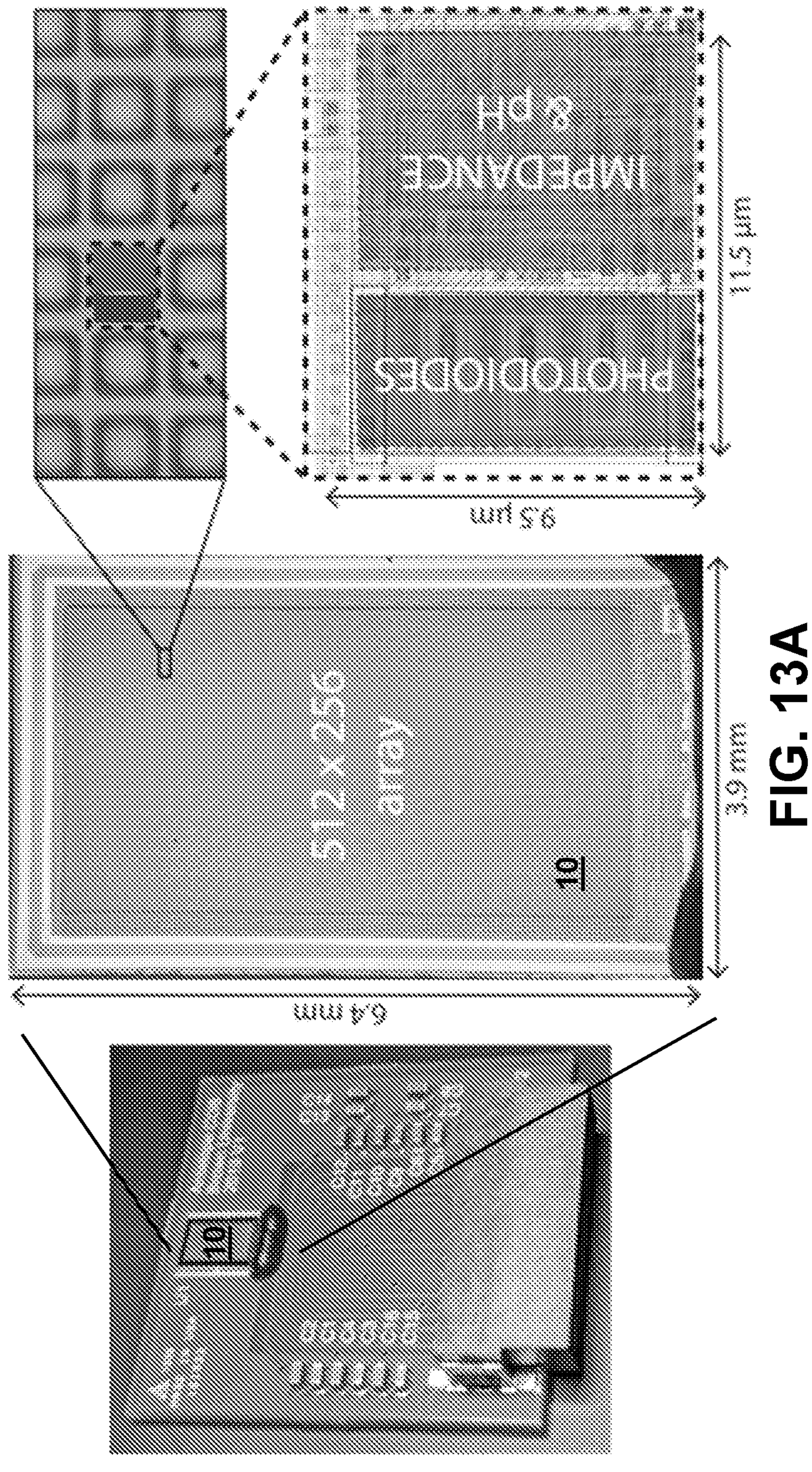
FIG. 13 shows images (with enlargements of the array) of a custom CMOS sensor array. In the example of FIG. 13A the 131,072 pixels (center, in array chip 10) can each measure local impedance, pH, and optical intensity (right).
FIG. 13B provides simplified example circuit schematics. The array chip 10 supports code division readout of many pixels concurrently, along with the example circuitry depicted.
Figure 13B:
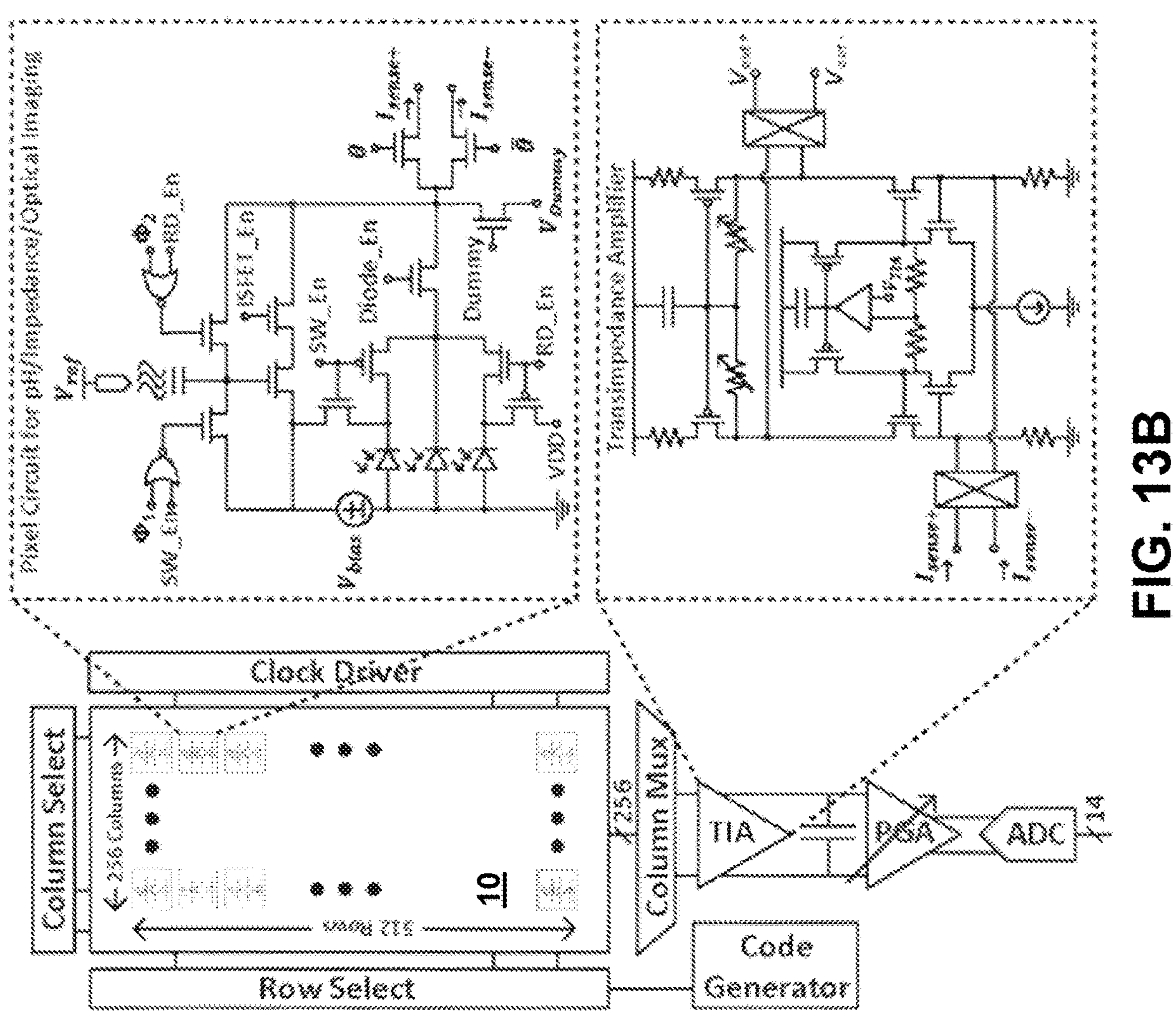

The active sensing area has 131,072 pixels arranged in a 512×256 array (FIG. 13A, 13B). Each 11.5 μm×9.5 μm pixel contains an electrode that can be used for impedance or pH measurements, as well as a multi-cathode photodiode. The sensor current is steered differentially onto a shared output column with a high-bandwidth differential current buffer to implement code-division multiplexed readout. Differential chopping is used to suppress 1/f noise and offsets. The output voltage is low-pass filtered, amplified, and then digitized by an external ADC at 500 kS/s. Inactive pixels can optionally be routed to a dummy column in order to reduce pixel-to-pixel parasitic coupling.

The array supports impedance measurements at frequencies up to 100 MHz. In comparison to traditional kHz EIS, radio frequency operation greatly reduces Debye screening, producing measurements sensitive to the dielectric environment farther from the electrode surface. Taking repeated measurements from a single test pixel at 1 millisecond intervals, we observe an effective noise floor of 0.7 aFrms (7×10−19 Farads).

The circuit is implemented in a 180 nm 1P6M CMOS process, with its active sensing area occupying 14.3 $mm^2$ of the 25 $mm^2$ chip (FIG. 13A). The chip is wirebonded to a small printed circuit board, which is connected to a custom data acquisition board. The bondwires are encapsulated with epoxy. A plastic fluid chamber is mounted around the chip with silicone adhesive, and we chemically etch away the aluminum top metal, exposing the electrodes' underlying titanium nitride diffusion barrier, a highly stable material which is used for both impedance[46] and pH[48] sensing.

Figures 14A, 14B:
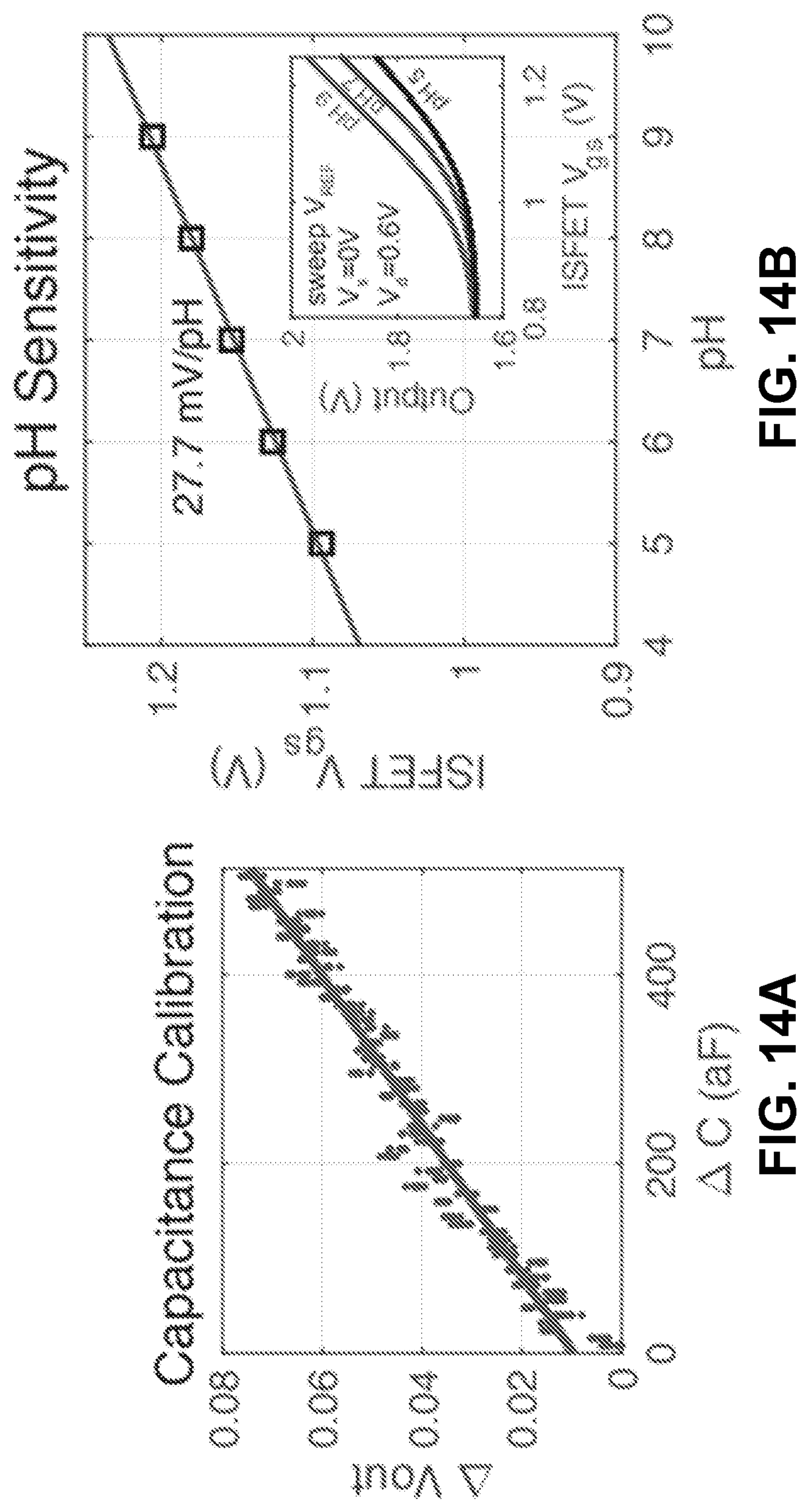
In FIG. 14A the dielectric measurements have a sub-attofarad noise floor.
FIG. 14B provides a plot of pH sensitivity. A 100 MHz dielectric contrast imaging of live bacteria colonies is shown in FIG. 14 C (left, optical image of bacteria after growth; right, false-color image of the dielectric sensor array data).

FIG. 14B shows the response of the TIN ISFETs[48], measured in 0.1M potassium phosphate buffer with an Ag/AgCl reference electrode. With Vgs=1.2 V, the sensitivity is 27.7 mV/pH.

Figure 14C:
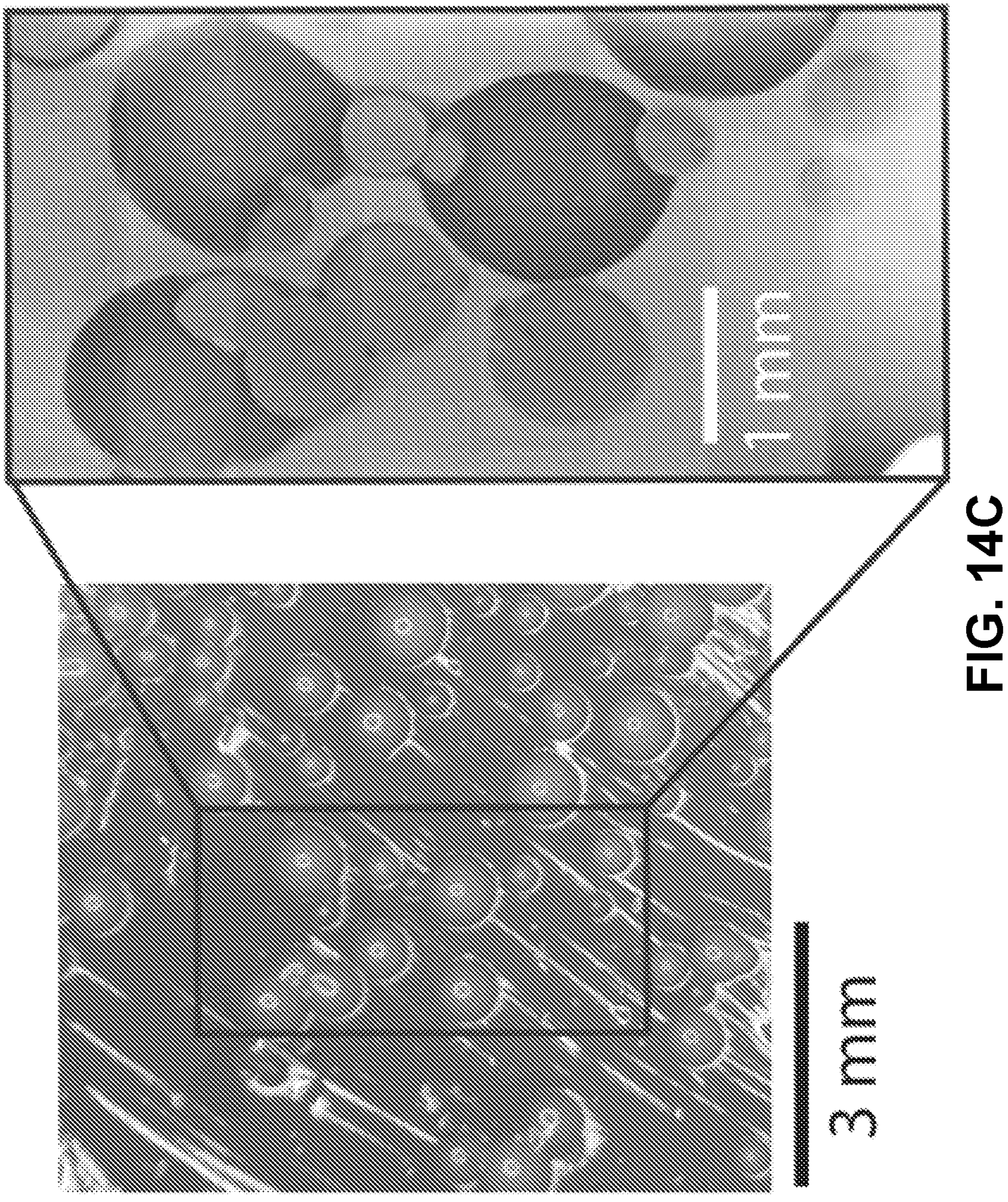
FIG. 14 provides signal to noise, sensitivity, and data structure illustrations.

We cultured samples from a skin swab on nutrient LB agar for 12 hours at 37° C., and the resulting colonies (likely *S. epidermidis*) were placed in contact with the sensor array. FIG. 14C shows a 100 MHz CDM impedance image of these live bacteria. The high contrast of this label-free non-optical image highlights the continued opportunities for lowcost and high performance active semiconductor-supported cell culture platforms.

Example 2 A 13.1 MM², 512×256 Multimodal CMOS Array for Spatiochemical Imaging of Bacterial Biofilms Biotechnology applications are increasingly turning to CMOS integrated biosensor arrays for massive parallelism and increased throughput in biomolecular diagnostics[77,78]. Yet many opportunities still remain to take advantage of the spatially-resolved nature of dense semiconductor platforms to open up new imaging dimensions[79,80,40] which complement traditional microscopy. To better understand the emergence of spatial organization in living systems, we require techniques that dynamically probe the spatial structure of assemblies of millions of cells or more. Optical microscopy is the dominant technique, but large field-of-view microscopes have an inherent tradeoff with resolving fine features. Confocal microscopes can image cellular-scale 3D structures, but their bright illumination can impart severe phototoxicity, and observing large areas can be prohibitively slow.

Here we present an integrated CMOS sensor array with 131,072 pixels, which is designed to electrochemically image and interface with bacterial biofilms. The architecture of the multimodal CMOS sensor array is shown in FIG. 15A to FIG. 15J. As illustrated, each pixel in the 512×256 array can be configured to measure impedance, pH, temperature, or electrochemical current, or perform bipolar voltage/current stimulation. In addition to its large active area and highly reconfigurable pixels, this is the first sensor in its class to support array-scale microscale electrical capacitance tomography through coordinated excitation and measurement from multiple pixels. Pixels are configured with row-wise and column-wise control signals, and each pixel has local SRAM to select between sensing and stimulation mode. Extensive circuit sharing is used to constrain each pixel to 10 μm×10 μm.

Figures 16A, 16B:
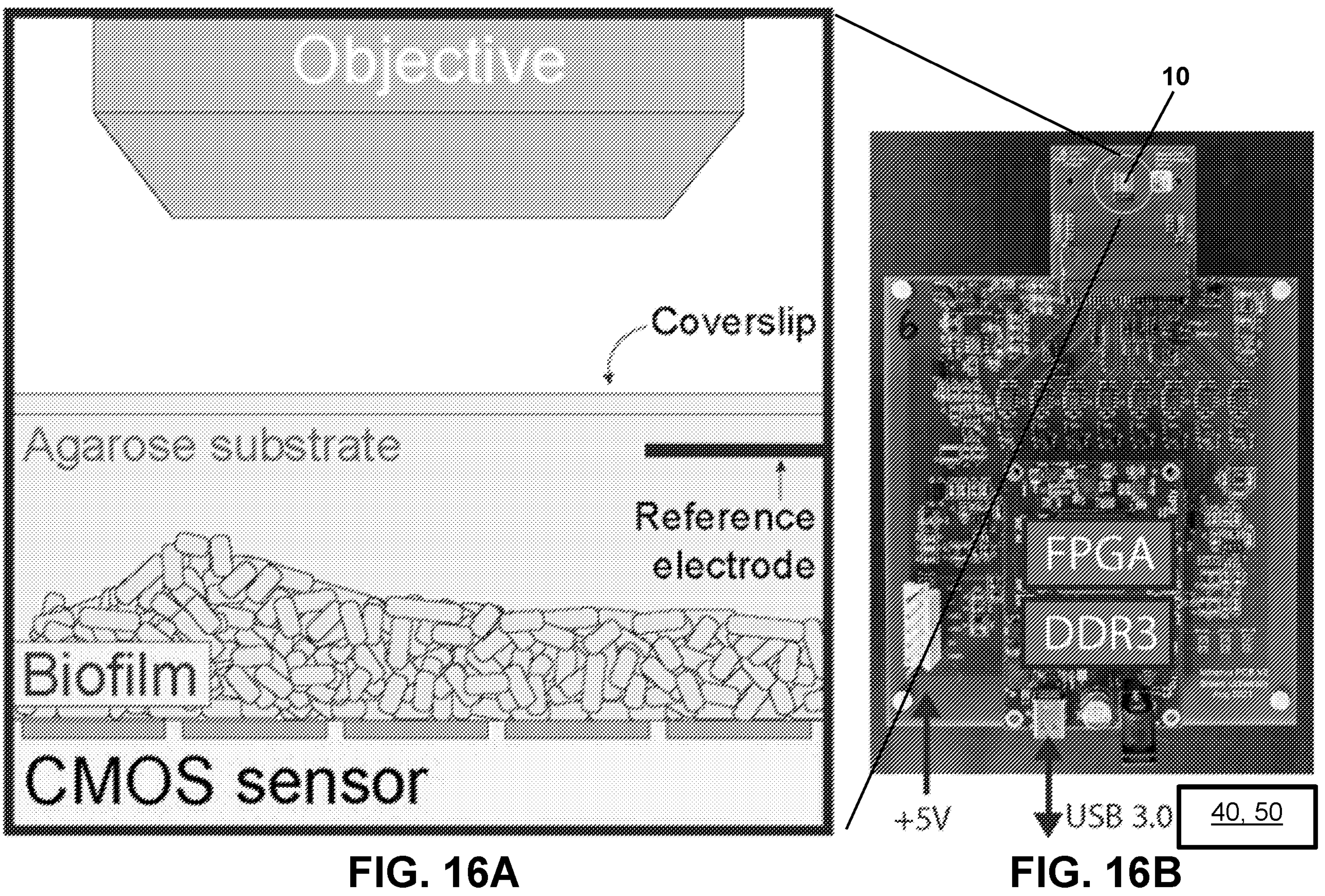
FIG. 16B shows a zoomed-out image of array chip 10 and supporting chips/circuitry (FIG. 16A is enlarged view).

The integrated sensing array is fabricated in 180 nm CMOS, occupying a total area of 25 $mm^2$, including the example of 13.1 $mm^2$ active sensing area. The chip is wirebonded to a small printed circuit board, and the bondwires are encapsulated with epoxy. The top aluminum layer from the CMOS foundry is chemically etched from the pixels, leaving behind the titanium nitride (TiN) diffusion barrier as the sensing electrode surface[80]. Columns are directed into 8 parallel readout signal paths which include a pair of integrators followed by buffers to drive 8 external 500 kS/s 18 bit ADCs. Correlated double sampling and chopping are applied to suppress offsets and 1/f noise. The sensor module is connected to a custom data acquisition board hosting an FPGA (e.g., FIG. 15B, FIG. 16B) and USB 3.0 interface. In FIG. 16B, the USB 3.0 interface can be in communication with processor 40 and/or additional memory 50. It is contemplated that the processor and/or memory can include software to perform detailed operations. System control and acquisition is managed through a Python environment. When active, the sensor consumes 58.8 mW, and full sensor frames take approximately 16 seconds to acquire. Impedance and capacitance sensing are established methods to detect cell adhesion and proliferation. In traditional non-integrated systems, impedance data is limited to a small number of scalar measurements, which limits the information available about spatial heterogeneity or morphology of the cell culture. Here, spatially resolved impedance measurements are assembled using a pair of non-overlapping clocks to rapidly charge and discharge each pixel's electrode, while the transferred interfacial charge is integrated. The switched-capacitor circuits operate at radio frequency (up to 100 MHz) which reduces Debye screening and allows observation of features farther from the surface. The result is a high-resolution image of the dielectric properties of cells and other molecules near the surface of the sensor. Each pixel contains an N-channel ion sensitive field effect transistor (ISFET), which uses the same electrode as the impedance sensing mode.

The measured pH sensitivity referred to the ISFET TiN gate is 27.2 mV/pH. Temperature fluctuations can have a significant impact on biofilm development, and the N channel ISFET can also be reconfigured as a temperature sensor, by diode-connecting its transistor and biasing it in subthreshold. Between 20° C. and 40° C. its sensitivity is approximately 0.2 nA/° C. per pixel, and held at a constant temperature of 25° C. for three hours the overall chip's measured temperature fluctuation was ±0.17° C. For interfacing with electrically excitable cell cultures, arbitrary patterns of bipolar voltage or current stimulation are supported by writing the stimulation state to each pixel's SRAM. Current or voltage stimulation are achieved by configuring the pullup and pulldown transistors either as switches or as cascode current sources. This function can be used for electrically stimulating cell cultures as well as electroplating alternative electrode materials. In addition, closing both stimulation switches can generate resistive heating for spatially-programmable thermal stimulation.

Figures 16C, 16D:
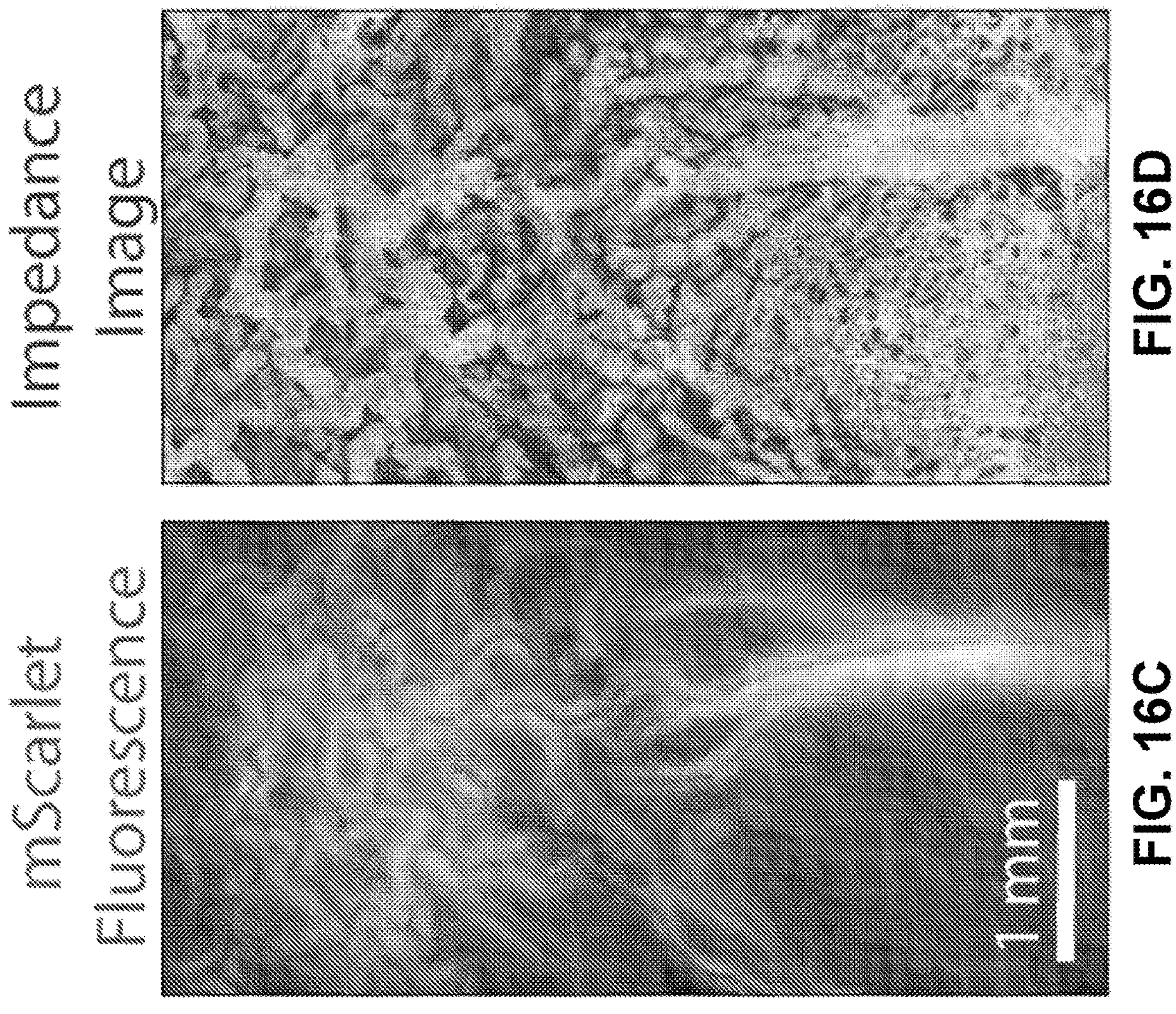
In FIG. 16C in FIG. 16D the mScarlet Fluorescence image (FIG. 16C, optical) is compared with the acquired Impedance Image (FIG. 16D). The complex structure within the biofilm correlates well between the sensor's impedance images (FIG. 16D) and optical fluorescence imaging (FIG. 16C).
Figures 17A, 17B:
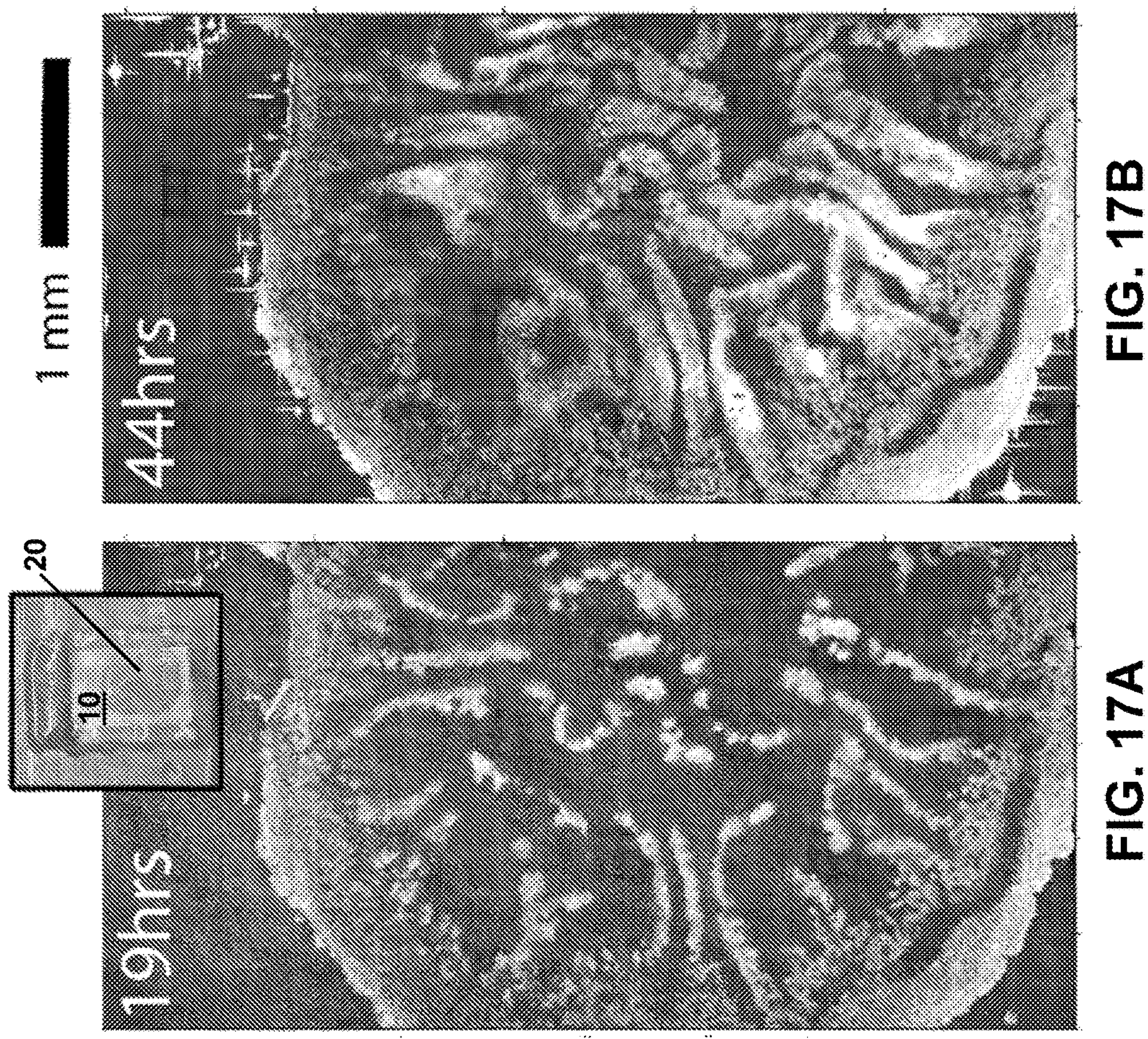
FIG. 17 provides impedance images illustrating how strains of *B. subtilis* which overexpress extracellular matrix polymers develop large wrinkles and complex morphology, which can be tracked over time with impedance imaging. Biofilm 20 is illustrated on an array chip 10 and imaging at 19 hours is provided in FIG. 17A, while imaging at 44 hours illustrates tracking over time in FIG. 17B (scale bar at top=1 mm).
Figures 18A, 18B:
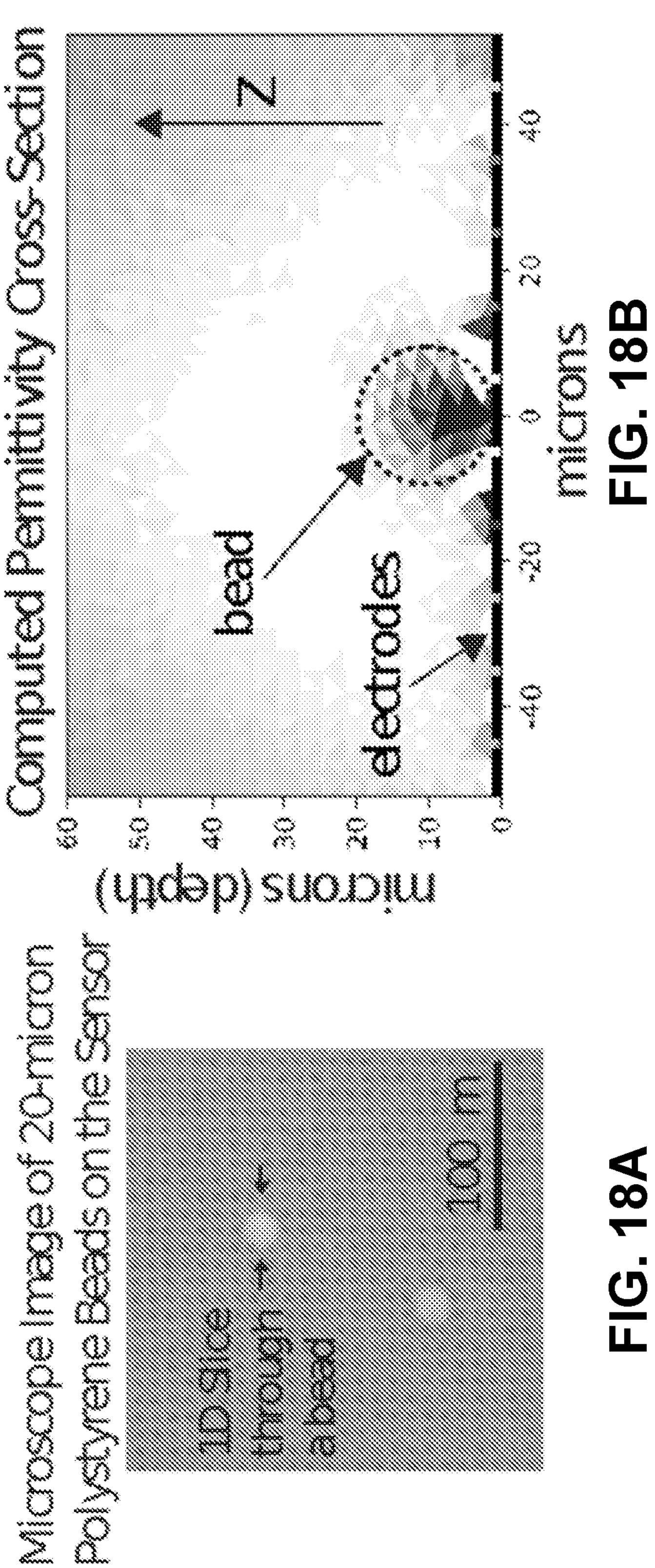
In FIG. 18A, a microscope image of 20-micron polystyrene beads on the sensor is provided to illustrate a 1D slice through a bead and how computed permittivity cross-section can be plotted (FIG. 18B) in microns (X-axis) vs. microns (depth, Y-axis).
Figures 18C, 18D:
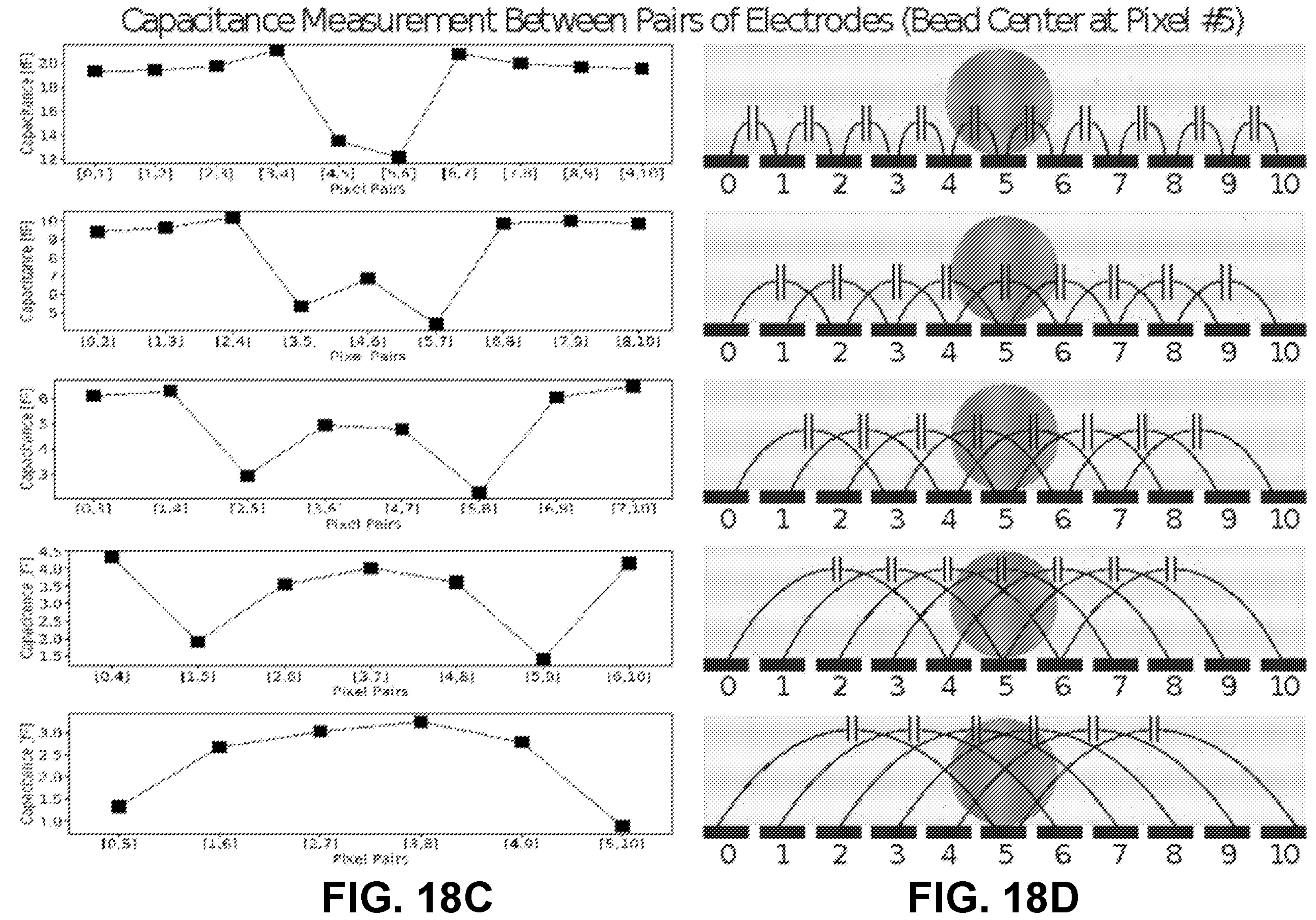
FIG. 18C and FIG. 18D show how capacitance measurement between pairs of electrodes (e.g., bead center at pixel #5) is used for capacitance tomography measurements.

We can apply this new sensor to produce state-of-the-art non-optical microscale maps of emergent structure within bacterial biofilms. Biofilms are communities of microbes that develop 2D and 3D morphology to coordinate their behaviors in response to environmental constraints and threats. There is great medical interest in combating biofilm infections, and biologists have made analogies between biofilm growth and embryonic development, highlighting the importance of biofilms as a transition to multicellularity[81]. FIG. 16A to FIG. 16D shows a *Bacillus subtilis* biofilm (NCIB3610) on the CMOS chip, and an impedance image from the sensor (FIG. 16D). This strain expresses a red fluorescent protein (mScarlet), allowing simultaneous optical observation (Olympus MVX10 microscope). There are strong correlations between the fluorescence and impedance images, and in fact many secondary structures are more clearly resolved in the impedance data. The new sensor can acquire temporally-resolved as well as spatially-resolved electrochemical images. In later stages of their development, biofilms can develop wrinkled 3D morphologies. In FIG. 17A and FIG. 17B, we show two impedance snapshots of microscale wrinkles emerging over time in a mutant strain of *B. subtilis* that overexpresses extracellular matrix (ΔsinR)[81]. High-impedance regions (white bands in FIGS. 17A and 17B) represent biofilm wrinkles that are in closer contact with the CMOS sensor, reducing the local dielectric constant. After 25 hours, the wrinkles have grown substantially. Biofilms often exist at 2D interfaces, but they have important 3D microstructure. In addition to producing 2D impedance images, the CMOS sensor incorporates depth sensitivity via computation of 3D permittivity distributions using electrical capacitance tomography. By rectifying and integrating the AC current from one pixel while switching a second pixel with opposite clock phases, the sensor can produce parasitic-insensitive measurements of the mutual capacitance between arbitrary pairs of pixels. The distanceCM between two pixels affects the out-of-plane depth of the resulting AC electric field. Measurements from multiple overlapping pairs of pixels can then be computationally combined to produce an inverse estimate of the 3D permittivity distribution within a sample. The useful reconstruction depth extends tens of microns above the sensor, which is appropriate for imaging biofilm thickness profiles and permittivity maps. FIGS. 18A, 18B, 18C, and 18D show an experimental reconstruction of the dielectric permittivity of a 20 micron polystyrene bead on the sensor.

Figures 19A, 19B:
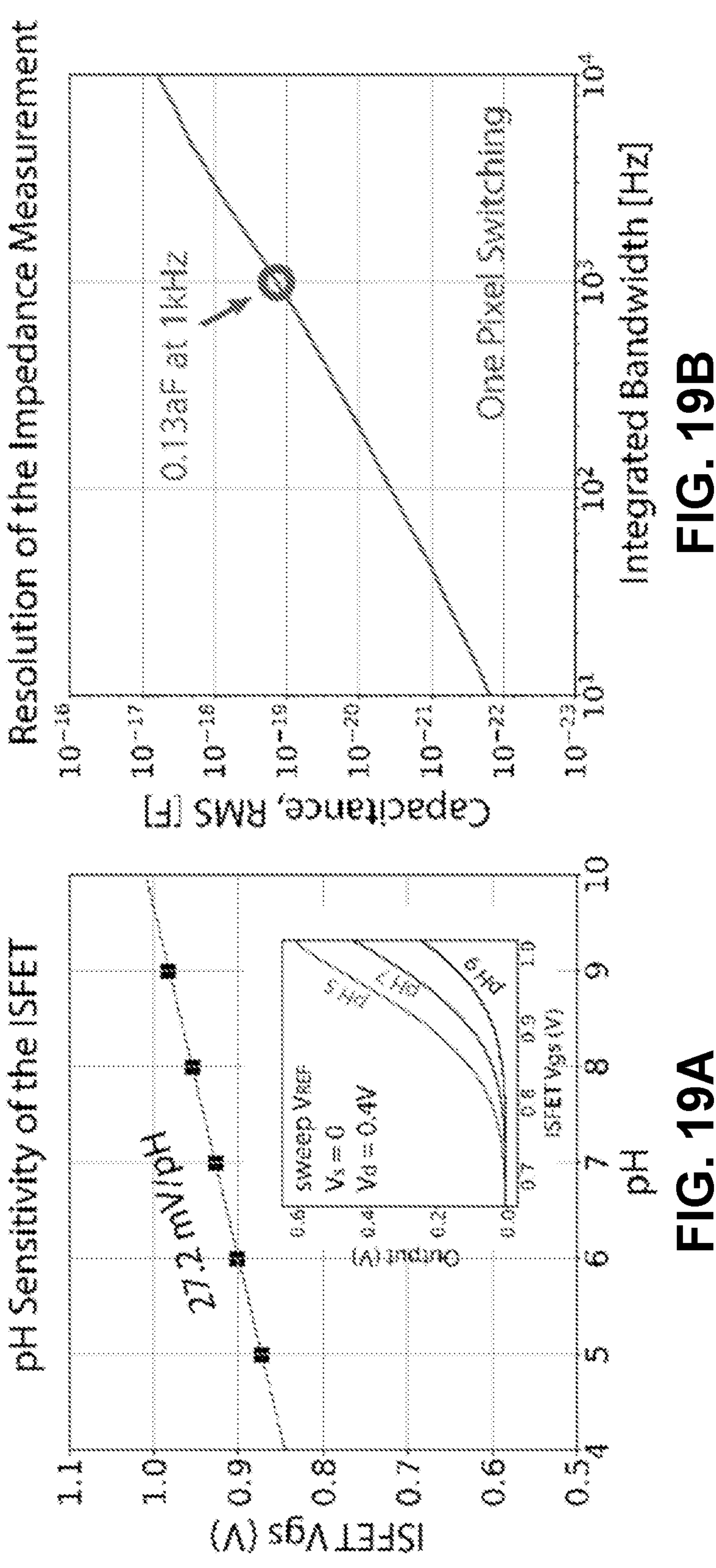
In FIG. 19A the pH sensitivity of the ISFETs is 27.2 mV/pH.
In FIG. 19B, the impedance resolution is 0.13 attofarads (rms) for a 1 ms integration period, which would correspond to an acquisition time of 16 seconds per frame. Temperature Sensor Response is illustrated in FIG. 19C, and at 25° C., the overall chip temperature measured variation (FIG. 19D) less than +0.2° C., over three hours.
Figures 19C, 19D:
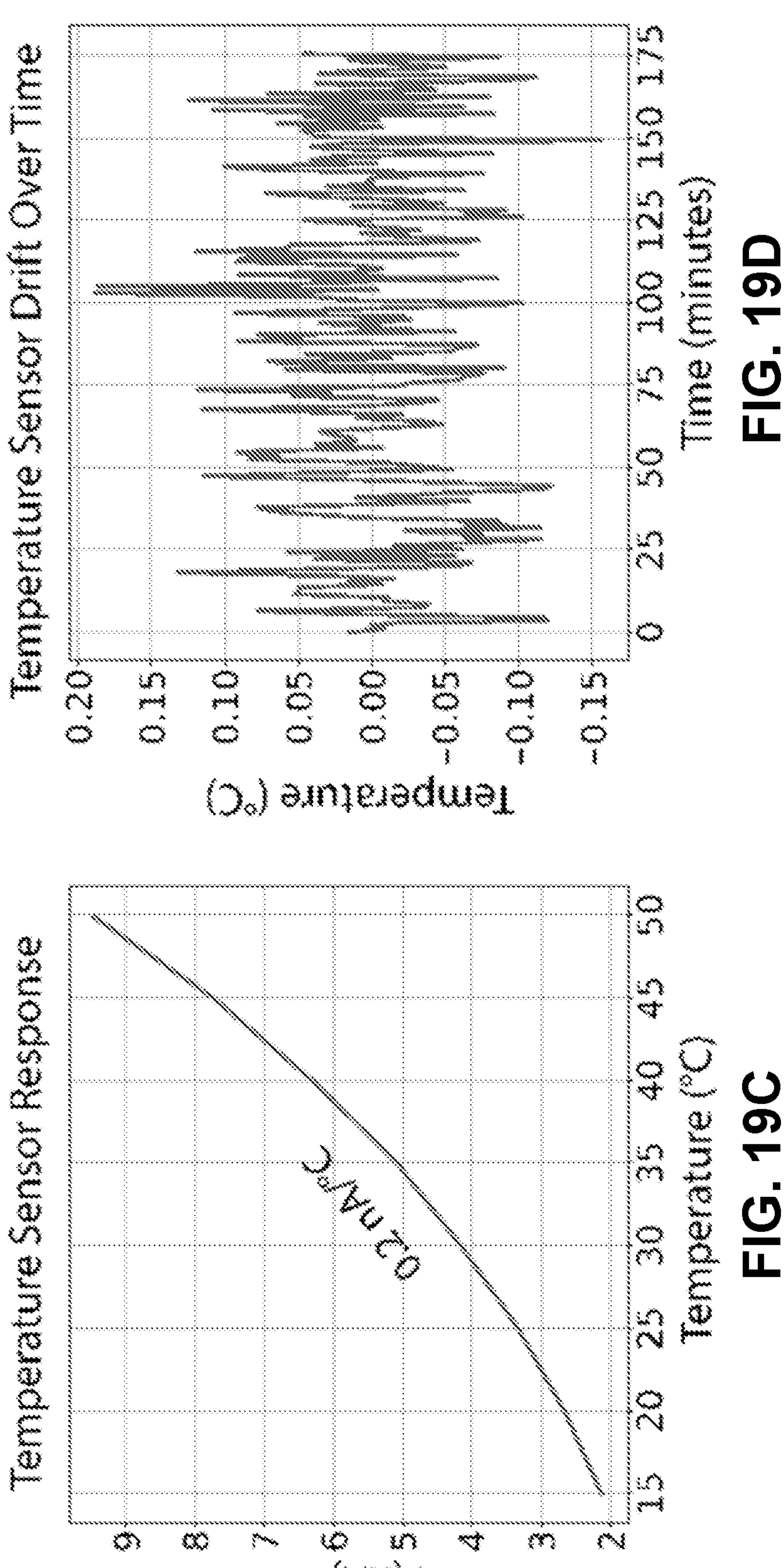
FIG. 19 provides sensitivity, resolution, response, and drift examples.

FIG. 19 provides sensitivity, resolution, response, and drift examples. In FIG. 19A the pH sensitivity of the ISFETs is 27.2 mV/pH. In FIG. 19B, the impedance resolution is 0.13 attofarads (rms) for a 1 ms integration period, which would correspond to an acquisition time of 16 seconds per frame. Temperature Sensor Response is illustrated in FIG. 19C, and at 25° C., the overall chip temperature measured variation (FIG. 19D) less than ±0.2° C., over three hours. FIG. 20 provides a summary table of some experimental demonstrations of the presently disclosed work.

Using a new CMOS electrochemical imaging array, we have presented high-resolution, non-optical images which reveal biofilm structure at spatial resolution competitive with widefield fluorescence imaging. The sensor rapidly captures label-free, non-optical images over a large field of view. Expanded spatially-resolved sensing and stimulation modalities will enable insights into large-scale structural development within bacterial colonies, opening up new directions for the study of microbial communities.

REFERENCES

[1] Hall-Stoodley L, Costerton J W, Stoodley P (February 2004). "Bacterial biofilms: from the natural environment to infectious diseases". Nature Reviews. Microbiology. 2 (2): 95-108.

[2] Momeni B (June 2018). "Division of Labor: How Microbes Split Their Responsibility". Current Biology. 28 (12): R697-R699.

[3] D Lee Dong-yeon, Arthur Prindle, Jintao Liu, and G ürol M S üel. Snapshot: electrochemical communication in biofilms. *Cell,* 170(1): 214-214, 2017.

[4] Nikhil S. Malvankar, Madeline Vargas, Kelly P. Nevin, Ashley E. Franks, Ching Leang, Byoung-Chan Kim, Kengo Inoue, T ünde Mester, Sean F. Covalla, Jessica P. Johnson, Vincent M. Rotello, Mark T. Tuominen, and Derek R. Lovley. Tunable metallic-like conductivity in microbial nanowire networks. *Nature Nanotechnology,* 6:573-579, 2011.

[5] Jonathan P. Remis, J. William Costerton, and Manfred Auer. Biofilms: structures that may facilitate cell-cell interactions. *The ISME Journal,* 4(2118):1085-1087, 2010.

[6] Raimo Hartmann, Praveen K. Singh, Philip Pearce, Rachel Mok, Boya Song, Francisco D'iaz-Pascual, J örn Dunkel, and Knut Drescher. Emergence of three-dimensional order and structure in growing biofilms. *Nature Physics,* 15:251-256, 2019.

[7] Luanne Hall-Stoodley, J. William Costerton, and Paul Stoodley. Bacterial biofilms: from the natural environment to infectious diseases. *Nature Reviews Microbiology,* 2(2118):95-108, 2004.

[8] Arthur Prindle, Jintao Liu, Munehiro Asally, San Ly, Jordi Garcia-Ojalvo, and G ürol M S üel. Ion channels enable electrical communication in bacterial communities. Nature, 527(7576):59-63, 2015.

[9] Joseph W Larkin, Xiaoling Zhai, Kaito Kikuchi, Samuel E Redford, Arthur Prindle, Jintao Liu, Sacha Greenfield, Aleksandra M Walczak, Jordi Garcia-Ojalvo, Andrew Mugler, and G ürol M S üel. Signal percolation within a bacterial community. Cell systems, 7(2):137-145, 2018.

[10] J William Costerton, G G Geesey, and K-J Cheng. How bacteria stick. Scientific American, 238(1):86-95, 1978.

[11] Dennis Claessen, Daniel E Rozen, Oscar P Kuipers, Lotte Søgaard-Andersen, and Gilles P Van Wezel. Bacterial solutions to multicellularity: a tale of biofilms, filaments and fruiting bodies. Nature Reviews Microbiology, 12(2): 115-124, 2014.

[12] Hans-Curt Flemming and Stefan Wuertz. Bacteria and archaea on earth and their abundance in biofilms. Nature Reviews Microbiology, 17(4):247-260, 2019.

[13] Thien-Fah C Mah and George A O'Toole. Mechanisms of biofilm resistance to antimicrobial agents. Trends in microbiology, 9(1):34-39, 2001.

[14] Yung-Hua Li and Xiaolin Tian. Quorum sensing and bacterial social interactions in biofilms. Sensors, 12(3): 2519-2538, 2012.

[15] Jintao Liu, Arthur Prindle, Jacqueline Humphries, Marc çl Gabalda-Sagarra, Munehiro Asally, D Lee Dong-yeon, San Ly, Jordi Garcia-Ojalvo, and G ürol M S üel. Metabolic co-dependence gives rise to collective oscillations within biofilms. Nature, 523(7562):550-554, 2015.

[16] Berend Tolner, Trees Ubbink-Kok, Bert Poolman, and Wil N Konings. Characterization of the proton/glutamate symport protein of *Bacillus subtilis* and its functional expression in *Escherichia coli*. Journal of bacteriology, 177(10):2863-2869, 1995.

[17] Chien-Jung Lo, Mark C. Leake, Teuta Pilizota, and Richard M. Berry. Nonequivalence of membrane voltage and ion-gradient as driving forcesfor the bacterial flagellar motor at low load. Biophysical Journal, 93:294-302, 2007.

[18] Jintao Liu, Rosa Martinez-Corral, Arthur Prindle, D Lee Dong-yeon, Joseph Larkin, Marc çl Gabalda-Sagarra, Jordi Garcia-Ojalvo, and G ürol M S üel. Coupling between distant biofilms and emergence of nutrient time-sharing. Science, 356(6338):638-642, 2017.

[19] Marie Engelene J Obien, Kosmas Deligkaris, Torsten Bullmann, Douglas J Bakkum, and Urs Frey. Revealing neuronal function through microelectrode array recordings. Frontiers in neuroscience, 8:423, 2015.

[20] January M üller, Marco Ballini, Paolo Livi, Yihui Chen, Milos Radivojevic, Amir Shadmani, Vijay Viswam, Ian L Jones, Michele Fiscella, Roland Diggelmann, et al. High-resolution cmos mea platform to study neurons at subcellular, cellular, and network levels. Lab on a Chip, 15(13):2767-2780, 2015.

[21] Carolina Mora Lopez, Alexandru *Andrei*, Srinjoy Mitra, Marleen Welkenhuysen, Wolfgang Eberle, Carmen Bartic, Robert Puers, Refet Firat Yazicioglu, and Georges GE Gielen. An implantable 455-active-electrode 52-channel cmos neural probe. IEEE Journal of Solid-State Circuits, 49(1):248-261, 2013.

[22] Bj örn Eversmann, Martin Jenkner, Franz Hofmann, Christian Paulus, Ralf Brederlow, Birgit Holzapfl, Peter Fromherz, Matthias Merz, Markus Brenner, Matthias Schreiter, Reinhard Gabl, Kurt Plehnert, Michael Steinhauser, Gerald Eckstein, Doris Schmitt-Landsiedel, and Roland Thewes. A 128×128 cmos biosensor array for extracellular recording of neural activity. IEEE Journal of Solid-State Circuits, 38(12):2306-2317, 2003.

[23] Reid R Harrison and Cameron Charles. A low-power low-noise cmos amplifier for neural recording applications. IEEE Journal of solid-state circuits, 38(6):958-965, 2003.

[24] Y-K Song, David A Borton, Sunmee Park, William R Patterson, Christopher W Bull, Farah Laiwalla, John Mislow, John D Simeral, John P Donoghue, and Arto V Nurmikko. Active microelectronic neurosensor arrays for implantable brain communication interfaces. IEEE Transactions on Neural Systems and Rehabilitation Engineering, 17(4):339-345, 2009.

[25] David Tsai, Daniel Sawyer, Adrian Bradd, Rafael Yuste, and Kenneth L Shepard. A very large-scale microelectrode array for cellular-resolution electrophysiology. Nature communications, 8(1):1-11, 2017.

[26] Jeffrey Abbott, Tianyang Ye, Ling Qin, Marsela Jorgolli, Rona S Gertner, Donhee Ham, and Hongkun Park. Cmos nanoelectrode array for all-electrical intracellular electrophysiological imaging. Nature nanotechnology, 12(5): 460, 2017.

[27] Marco Ballini, Jan M üller, Paolo Livi, Yihui Chen, Urs Frey, Alexander Stettler, Amir Shadmani, Vijay Viswam, Ian Lloyd Jones, David J äckel, et al. A 1024-channel cmos microelectrode array with 26,400 electrodes for recording and stimulation of electrogenic cells in vitro. IEEE journal of solid-state circuits, 49(11):2705-2719, 2014.

[28] Elon Musk et al. An integrated brain-machine interface platform with thousands of channels. *Journal of medical Internet research,* 21(10):e16194, 2019.

[29] Rikky Muller, Simone Gambini, and Jan M Rabaey. A 0.013 $mm^2$, 5μw, dc-coupled neural signal acquisition ic with 0.5 v supply. IEEE Journal of Solid-State Circuits, 47(1):232-243, 2011.

[30] Flavio Heer, Sadik Hafizovic, Wendy Franks, Axel Blau, Christiane Ziegler, and Andreas Hierlemann. Cmos microelectrode array for bidirectional interaction with neuronal networks. IEEE Journal of Solid-State Circuits, 41(7):1620-1629, 2006.

[31] Arun Manickam, Rituraj Singh, Nicholas Wood, Bingling Li, Andrew Ellington, and Arjang Hassibi. A fully-electronic charge-based dna sequencing cmos biochip. In 2012 Symposium on VLSI Circuits (VLSIC), pages 126-127. IEEE, 2012.

[32] James Bustillo, Keith Fife, Barry Merriman, and Jonathan Rothberg. Development of the ion torrent cmos chip for dna sequencing. In 2013 IEEE International Electron Devices Meeting, pages 8-1. IEEE, 2013.

[33] Miten Jain, Hugh E Olsen, Benedict Paten, and Mark Akeson. The oxford nanopore minion: delivery of nanopore sequencing to the genomics community. Genome biology, 17(1):239, 2016.

[34] Carl W Fuller, Shiv Kumar, Mintu Porel, Minchen Chien, Arek Bibillo, P Benjamin Stranges, Michael Dorwart, Chuanjuan Tao, Zengmin Li, Wenjing Guo, et al. Real-time single-molecule electronic dna sequencing by synthesis using polymer-tagged nucleotides on a nanopore array. Proceedings of the National Academy of Sciences, 113(19):5233-5238, 2016.

[35] Jacob K Rosenstein, Meni Wanunu, Christopher A Merchant, Marija Drndic, and Kenneth L Shepard. Integrated nanopore sensing platform with sub-microsecond temporal resolution. Nature methods, 9(5):487, 2012.

[36] Mario M Modena, Ketki Chawla, Patrick M Misun, and Andreas Hierlemann. Smart Cell Culture Systems: Integration of Sensors and Actuators into Microphysiological Systems. ACS Chemical Biology, 13(7):1767-1784, 2018.

[37] Doohwan Jung, Jong Seok Park, Gregory V Junek, Sandra I. Grijalva, Sagar R Kumashi, Adam Wang, Sensen Li, Hee Cheol Cho, and Hua Wang. A 21952-Pixel Multi-Modal CMOS Cellular Sensor Array with 1568-Pixel Parallel Recording and 4-Point Impedance Sensing. 2019 Symposium on VLSI Circuits, pages C62-C63, 2019.

[38] B. P. Senevirathna, S. Lu, M. P. Dandin, J. Basile, E. Smela, and P. A. Abshire. Real-time measurements of cell proliferation using a lab-on-cmos capacitance sensor array. IEEE Transactions on Biomedical Circuits and Systems, 12(3):510-520, June 2018.

[39] Daniel L Bellin, Hassan Sakhtah, Jacob K Rosenstein, Peter M Levine, Jordan Thimot, Kevin Emmett, Lars E P Dietrich, and Kenneth L Shepard. Integrated circuit-based electrochemical sensor for spatially resolved detection of redox-active metabolites in biofilms. Nature communications, 5:3256, jan 2014.

[40] F. Widdershoven, A. Cossettini, C. Laborde, A. Bandiziol, P. P. van Swinderen, S. G. Lemay, and L. Selmi. A cmos pixelated nanocapacitor biosensor platform for high-frequency impedance spectroscopy and imaging. IEEE Transactions on Biomedical Circuits and Systems, 12(6): 1369-1382 Dec. 2018.

[41] X. Huang, H. Yu, X. Liu, Y. Jiang, M. Yan, and D. Wu. A dual-mode large-arrayed cmos isfet sensor for accurate and high-throughput ph sensing in biomedical diagnosis. IEEE Transactions on Biomedical Engineering, 62(9): 2224-2233 Sep. 2015.

[42] Allen J Bard, Larry R Faulkner, Johna Leddy, and Cynthia G Zoski. Electrochemical methods: fundamentals and applications, volume 2. wiley New York, 1980.

[43] E. Barsoukov and J. R. Macdonald. Impedance Spectroscopy; Theory, Experiment, and Applications. Wiley Interscience Publications, 2005. 2nd ed.

[44] Liju Yang and Rashid Bashir. Electrical/electrochemical impedance for rapid detection of foodborne pathogenic bacteria. Biotechnology advances, 26(2):135-150, 2008.

[45] Sergio Verdu. Multiuser Detection. Cambridge University Press, 1998.

[46] Kangping Hu, Eamonn Kennedy, and Jacob K Rosenstein. High frequency dielectric spectroscopy array with code division multiplexing for biological imaging. In 2019 IEEE Biomedical Circuits and Systems Conference (BioCAS), pages 1-4. IEEE, 2019.

[47] H. Ouh and M. L. Johnston. Code-division multiplex encoding analog front end for current-mode sensor arrays. IEEE Solid-State Circuits Letters, 1(5):118-121, May 2018.

[48] Kangping Hu, Xiaoyu Lian, Shanshan Dai, and Jacob K Rosenstein. Low noise cmos isfets using in-pixel chopping. In 2019 IEEE Biomedical Circuits and Systems Conference (BioCAS), pages 1-4. IEEE, 2019.

[49] S. Wakida, S. Mochiziuki, R. Makabe, A. Kawahara, M. Yamane, S. Takasuka, and K. Higashi. pH-sensitive ISFETs based on titanium nitride and their application to battery monitor. In TRANSDUCERS '91:1991 International Conference on Solid-State Sensors and Actuators. Digest of Technical Papers, pages 222-224, June 1991.

[50] Suzan Meijs, Morten Fjorback, Carina Jensen, Søren Sørensen, Kristian Rechendorff, and Nico JM Rijkhoff. Electrochemical properties of titanium nitride nerve stimulation electrodes: an in vitro and in vivo study. Frontiers in neuroscience, 9:268, 2015.

[51] Clifford Wolf. Picorv32-a size-optimized risc-v cpu, 2019.

[52] Hera Vlamakis, Claudio Aguilar, Richard Losick, and Roberto Kolter. Control of cell fate by the formation of an architecturally complex bacterial community. Genes & development, 22(7):945-953, 2008.

[53] Siddarth Srinivasan, loana D Vladescu, Stephan A Koehler, Xiaoling Wang, Madhav Mani, and Shmuel M Rubinstein. Matrix production and sporulation in *Bacillus subtilis* biofilms localize to propagating wave fronts. Biophysical journal, 114(6):1490-1498, 2018.

[54] Roberto R Grau, Paula de Ö na, Maritta Kunert, Cecilia Lë nini, Ramses Gallegos-Monterrosa, Eisha Mhatre, Dar'io Vileta, Ver'onica Donato, Theresa H ölscher, Wilhelm Boland, Oscar P Kuipers, and Akos T Kovacs. A duo of potassium-responsive histidine kinases govern the multicellular destiny of *Bacillus subtilis*. MBio, 6(4):e00581-15, 2015.

[55] Douglas J. Bakkum, Urs Frey, Milos Radivojevic, Thomas L. Russell, Jan M üller, Michele Fiscella, Hirokazu Takahashi, and Andreas Hierlemann. Tracking axonal action potential propagation on a high-density microelectrode array across hundreds of sites. Nature Communications, 4(2118), 2013.

[56] Jintao Liu, Arthur Prindle, Jacqueline Humphries, Marc çl Gabalda-Sagarra, Munehiro Asally, Dongyeon D. Lee, San Ly, Jordi Garcia-Ojalvo, and G ürol M S üel. Metabolic co-dependence gives rise to collective oscillations within biofilms. Nature, 523(7562):550-554, 2015.

[57] Julien Dervaux, Juan Carmelo Magniez, and Albert Libchaber. On growth and form of *Bacillus subtilis* biofilms. Interface Focus, 4(6):20130051, 2014.

[58] Johannes Lengler, Florian Jug, and Angelika Steger. Reliable neuronal systems: The importance of heterogeneity. PLOS ONE, 8(12):e80694, 2013.

[59] M. Gibertini, M. Koperski, A. F. Morpurgo, and K. S. Novoselov. Magnetic 2D materials and heterostructures. Nature Nanotechnology, 14(5):408-419, May 2019.

[60] D. Chandler, D. L. Chandler, and D. Wu. Introduction to Modern Statistical Mechanics. Oxford University Press, 1987.

[61] A. Lucas. Ising formulations of many NP problems. Front. Phys., 12:5, 2014.

[62] J. M. Kosterlitz. The critical properties of the two-dimensional xy model. Journal of Physics C: Solid State Physics, 7(6), 1974.

[63] R. Martinez-Corrala, G. M. Suel J. Liub, c, and J. Garcia-Ojalvo. Bistable emergence of oscillations in growing *Bacillus subtilis* biofilm. Proceedings National Academy of Sciences, 115(36), 2018.

[64] J. Cortes and F. Bullo. Coordination and Geometric Optimization via Distributed Dynamical Systems. SIAM J. Control Optim., 44(5):1543-1574, 2005.

[65] The Merck Manual of Diagnosis and Therapy, (2011). 19$^{th}$ Edition, published by Merck Sharp & Dohme Corp., (ISBN 978-O-911910-19-3).

[66] The Encyclopedia of Molecular Cell Biology and Molecular Medicine, Robert S. Porter et al. (eds.), published by Blackwell Science Ltd., 1999-2012 (ISBN 9783527600908).

[67] Molecular Biology and Biotechnology: a Comprehensive Desk Reference, (1995). Robert A. Meyers (ed.), published by VCH Publishers, Inc. (ISBN 1-56081-569-8).

[68] Immunology, (2006). Werner Luttmann, published by Elsevier.

[69] Janeway's Immunobiology, (2014). Kenneth Murphy, Allan Mowat, Casey Weaver (eds.), Taylor & Francis Limited, (ISBN 0815345305, 9780815345305).

[70] Lewin's Genes XI, (2014). published by Jones & Bartlett Publishers (ISBN-1449659055).

[71] Michael Richard Green and Joseph Sambrook, (2012). Molecular Cloning: A Laboratory Manual, 4th ed., Cold Spring Harbor Laboratory Press, Cold Spring Harbor, N.Y., USA (ISBN 1936113414).

[72] Davis et al., (2012). Basic Methods in Molecular Biology, Elsevier Science Publishing, Inc., New York, USA (ISBN 044460149X).

[73] Laboratory Methods in Enzymology: DNA, (2013). Jon Lorsch (ed.) Elsevier (ISBN 0124199542).

[74] Current Protocols in Molecular Biology (CPMB), (2014). Frederick M. Ausubel (ed.), John Wiley and Sons (ISBN 047150338X, 9780471503385).

[75] Current Protocols in Protein Science (CPPS), (2005). John E. Coligan (ed.), John Wiley and Sons, Inc.

[76] Current Protocols in Immunology (CPI) (2003). John E. Coligan, ADA M Kruisbeek, David H Margulies, Ethan M Shevach, Warren Strobe, (eds.) John Wiley and Sons, Inc. (ISBN 0471142735, 9780471142737).

[77] J. M. Rothberg et al., Nature, 2011, DOI: 10.1038/nature10242

[78] X. Huang et al., TBioCAS, 2015, DOI: 10.1109/TBME.2015.2419233.

[79] J. S. Park et al., TBioCAS, 2018, DOI: 10.1109/TBCAS.2017.2759220

[80] K. Hu et al., SSCL, 2021, DOI: 10.1109/LSSC.2021.3056515.

[81] H. Vlamakis et al., Nature Reviews Microbiology, 2013, DOI: 10.1038/nrmicro2

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

What is claimed is:

1. A CMOS (complementary metal-oxide semiconductor) chip comprising:

an array of pixels, each pixel comprising a circuit operative to measure from and/or to apply an electrical charge and/or impedance to at least a portion of a living biofilm disposed on the array;

the living biofilm disposed on the array, wherein the portion of the living biofilm is in discrete electrical communication with each pixel; and a circuit in electrical communication with the array, said circuit operative to provide at least one signal for each pixel.

2. The CMOS chip of claim 1, wherein each pixel comprises at least one circuit operative to perform a function selected from stimulate, heat, impedance image, measure pH, ion imaging/measurement, temperature measurement, stimulation, measure an amperometry, measure a voltage, measure a resistance, and measure an impedance tomography, of the portion of the biofilm.

3. The CMOS chip of claim 1, further comprising a reference electrode and a hydrogel disposed over the living biofilm.

4. The CMOS chip of claim 1, wherein the living biofilm is configured with at least two biofilms, each of the at least two biofilms in communication with another of the at least two biofilms, wherein the communication comprises a signaling and/or a coupling between biofilms.

5. The CMOS chip of claim 1, wherein the living biofilm comprises a genetically modified strain of bacteria.

6. The CMOS chip of claim 1, further comprising a processor, memory, programming instructions, and/or display operative to read, store, and display at least one measurement, charge, and/or impedance from the array.

7. The CMOS chip of claim 1, wherein the chip is operative to apply an electrical stimulation to a pixel including the living biofilm disposed on the pixel, the electrical stimulation comprising at least a bit of information provided in a current/voltage stimulation, and said living biofilm is operative to store the bit for a period of time.

8. The CMOS chip of claim 1, wherein a bit of information can be read from the living biofilm by applying at least an impedance measurement, a resistance measurement, an amperometry measurement, a current/voltage stimulation, or a combination thereof to the pixel; and wherein the living biofilm is capable of changing at least one bit by a cell-to-cell and/or a biofilm-to-biofilm interaction.

9. The CMOS chip of claim 1, wherein the chip is configured as an imaging chip capable of imaging the living biofilm including computed tomography and/or impedance imaging of the living biofilm, and wherein each pixel represents an imaging pixel.

10. A method for measuring at least one aspect of a biofilm, the method comprising the steps of:

(1) obtaining a CMOS (complementary metal-oxide semiconductor) chip comprising:

an array of pixels, each pixel comprising a circuit operative to measure from and/or to apply an electrical charge and/or impedance to at least a portion of the biofilm;

the biofilm disposed on the array, the portion of the biofilm in electrical communication with each pixel; and a circuit in electrical communication with the array, said circuit operative to provide at least one signal for each pixel;

(2) applying a current and/or voltage to the biofilm directly disposed on a pixel, whereby the current and/or voltage is in electrical communication with at least the portion of the biofilm and provides a signal indicative of a condition of the at least the portion of the biofilm; and (3) transmitting the signal via an electrical conductor from the pixel to an additional circuitry operative to move the signal from the chip.

11. The method of claim 10, further comprising circuitry in communication with the chip, said circuitry in communication with the chip operative to provide the signal to a processor, memory, field-programmable gate array, DDR3 (RAM/SDRAM), a USB 3.0 output, an analog to digital convertor (ADC), or a combination thereof.

12. The method of claim 10, wherein the (2) applying a current and/or voltage to a pixel is operative to store at least a bit of information in the biofilm.

13. The method of claim 10, wherein at least a bit of information in the biofilm is capable of being read back by a repeating of step (2) and step (3) in any order.

14. The method of claim 10, wherein the method is repeated in steps (2) and (3) to different pixels, whereby a plurality of bits of information is applied to discrete areas of the biofilm.

15. The method of claim 10, wherein the method changes patterns of a cellular gene expression, intracellular and/or extracellular electrical responses, and/or communication between/among at least one biofilm.

16. The method of claim 10, wherein the biofilm comprises cells/microbes of fungal, bacterial, and/or eukaryotic origin, optionally wherein the cells are derived from *Staphylococcus aureus, Escherichia coli, Streptococcus pneumoniae, Pseudomonas aeruginosa, Bacillus subtilis*, skin (epidermal/dermal) cells, or the archaeal species *H. volcanii*, transfected cells, recombinant cells, genetically engineered cells, normal eukaryotic cells, immune cells such as macrophages, eosinophils, or a combination thereof.

17. The method of claim 10, wherein the biofilm includes viruses, culture medium, pharmaceutical agents, prions, oligonucleotides, antibodies, additives, or a combination thereof.

18. A method for computing within a biofilm, the method comprising the steps of:

(1) obtaining a CMOS (complementary metal-oxide semiconductor) chip comprising:

an array of pixels, each pixel comprising a circuit operative to measure from and/or to apply an electrical charge and/or impedance to at least a portion of the biofilm;

the biofilm disposed on the array, the portion of the biofilm in electrical communication with each pixel; and a circuit in electrical communication with the array, said circuit operative to provide at least one signal for each pixel;

(2) applying a current and/or voltage to the biofilm directly disposed on a pixel, whereby the current and/or voltage is in electrical communication with the at least the portion of the biofilm and stores a signal indicative of a bit of information in the at least the portion of the biofilm;

(3) repeating step (2) such that a plurality of different bits of information are stored in discrete pixels of the biofilm; and (4) waiting a period of time for an interaction between pixels of the biofilm; whereby said interaction is a computation within the biofilm.

19. The method of claim 18, wherein the plurality of different bits of information is representative of a problem selected from a 2D lattice model, Ising model, an analog model, and an XY model; and wherein the period of time is sufficient for the biofilm to change at least one of the bits of information.

20. The method of claim 18, further comprising the step:

(5) repeatedly applying a current and/or voltage to the biofilm directly disposed on a pixel, while changing the position of the pixel, whereby a change in at least one bit caused by the biofilm is detected and such change is representative of a computation performed within the biofilm.

* * * * *